(12) United States Patent
Neumann

(10) Patent No.: US 12,254,982 B2
(45) Date of Patent: Mar. 18, 2025

(54) METHODS AND SYSTEMS FOR ACHIEVING VIBRANT CONSTITUTION BASED ON USER INPUTS

(71) Applicant: Kenneth Neumann, Lakewood, CO (US)

(72) Inventor: Kenneth Neumann, Lakewood, CO (US)

(73) Assignee: KPN Innovations LLC, Lakewood, CO (US)

( * ) Notice: Subject to any disclaimer, the term of this patent is extended or adjusted under 35 U.S.C. 154(b) by 990 days.

(21) Appl. No.: 16/502,835

(22) Filed: Jul. 3, 2019

(65) Prior Publication Data
US 2021/0005317 A1 Jan. 7, 2021

(51) Int. Cl.
*G16H 50/20* (2018.01)
*G06N 20/00* (2019.01)
*G16H 20/60* (2018.01)
*G16H 50/70* (2018.01)

(52) U.S. Cl.
CPC ............ *G16H 50/20* (2018.01); *G06N 20/00* (2019.01); *G16H 20/60* (2018.01); *G16H 50/70* (2018.01)

(58) Field of Classification Search
CPC ........ G16H 50/20; G16H 20/60; G16H 50/70; G16H 40/67; G16H 50/00; G06N 20/00; G06N 5/022; Y02A 90/10
See application file for complete search history.

(56) References Cited

U.S. PATENT DOCUMENTS

| | | | |
|---|---|---|---|
| 5,954,640 A * | 9/1999 | Szabo | G16H 10/60 600/300 |
| 7,974,924 B2 * | 7/2011 | Holla | H04L 9/14 705/51 |
| 8,764,447 B2 | 4/2014 | Fieldberg | |
| 9,011,153 B2 | 4/2015 | Bennett et al. | |
| 2004/0139043 A1 * | 7/2004 | Lei | G06F 21/6227 |
| 2006/0045909 A1 | 3/2006 | Friesen et al. | |
| 2006/0112050 A1 * | 5/2006 | Miikkulainen | G16H 50/20 706/46 |
| 2006/0287890 A1 * | 12/2006 | Stead | G16H 10/20 705/3 |
| 2007/0116036 A1 * | 5/2007 | Moore | H04L 67/00 370/462 |

(Continued)

OTHER PUBLICATIONS

PCT/US20/39101, International Search Report, Mar. 9, 2020.
(Continued)

*Primary Examiner* — Kris E Mackes
*Assistant Examiner* — Cecile H Vo
(74) *Attorney, Agent, or Firm* — Caldwell Intellectual Property Law

(57) ABSTRACT

A system for achieving vibrant constitution based on user inputs. The system includes at least a server designed and configured to receive training data. The system includes a diagnostic engine operating on the at least a server designed and configured to record at least a biological extraction from a user and generate a diagnostic output. The system includes a plan generator module operating on the at least a server designed and configured to generate a comprehensive instruction set. The system includes an alimentary instruction set generator module designed and configured to receive at least a user input and generate at least an alimentary instruction set.

12 Claims, 21 Drawing Sheets

(56) References Cited

U.S. PATENT DOCUMENTS

| | | | | |
|---|---|---|---|---|
| 2007/0168461 A1* | 7/2007 | Moore | ............... | G16H 10/60 |
| | | | | 709/217 |
| 2007/0260481 A1 | 11/2007 | Marshall | | |
| 2009/0275002 A1 | 11/2009 | Hoggle | | |
| 2011/0225114 A1 | 9/2011 | Gotthardt | | |
| 2012/0046878 A1 | 2/2012 | Khan et al. | | |
| 2012/0183932 A1* | 7/2012 | Chang | ............... | G09B 5/125 |
| | | | | 434/127 |
| 2013/0224694 A1 | 8/2013 | Moore | | |
| 2014/0287384 A1* | 9/2014 | Boyes | ............... | G09B 5/02 |
| | | | | 434/127 |
| 2015/0269865 A1 | 9/2015 | Volach | | |
| 2017/0316352 A1 | 11/2017 | Abujbara | | |
| 2018/0004790 A1* | 1/2018 | Bhatt | ............... | G09B 19/0092 |
| 2018/0075199 A1 | 3/2018 | Meyerson et al. | | |
| 2018/0082139 A1 | 3/2018 | Li et al. | | |
| 2018/0233223 A1 | 8/2018 | Solari | | |
| 2019/0005201 A1 | 1/2019 | Fleming et al. | | |
| 2020/0380888 A1* | 12/2020 | Neumann | ............... | G09B 19/0092 |
| 2022/0406215 A1* | 12/2022 | Quinn | ............... | G09B 19/0092 |

OTHER PUBLICATIONS

My diet clinic; Nutrigenomi; http://mydietclinic.com/services/nutrigenomix-testing/#.XP_9bchKg2w (Copyright 2012, saved from the internet on Aug. 16, 2019).

Baze; True change comes from within; https://www.baze.com/ (saved from the internet on Aug. 16, 2019).

Select the right plan for your goal; https://www.insidetracker.com/store (Copyright 2009-2019, saved from the internet on Aug. 16, 2019).

* cited by examiner

METHODS AND SYSTEMS FOR ACHIEVING VIBRANT CONSTITUTION BASED ON USER INPUTS

FIELD OF THE INVENTION

The present invention generally relates to the field of artificial intelligence. In particular, the present invention is directed to methods and systems for achieving vibrant constitution based on user inputs.

BACKGROUND

Generating accurate instruction sets is challenging. This is in part hampered by the vast amount of data and text to be analyzed. Current solutions fail to create accurate and customized instruction sets.

SUMMARY OF THE DISCLOSURE

A system for achieving vibrant constitution based on user inputs. The system includes at least a server, wherein the at least a server is designed and configured to receive training data. The system includes a diagnostic engine operating on the at least a server wherein the diagnostic engine is configured to record at least a biological extraction from a user; and generate a diagnostic output based on the at least a biological extraction and training data. The system includes a plan generator module operating on the at least a server designed and configured to generate a comprehensive instruction set associated with the user as a function of the diagnostic output. The system includes an alimentary instruction set generator module operating on the at least a server, the alimentary instruction set generator module designed and configured to receive at least a user input; and generate at least an alimentary instruction set as a function of the comprehensive instruction set and the at least a user input.

A method of achieving vibrant constitution based on user inputs. The method includes receiving by at least a server training data. The method includes recording at least a biological extraction from a user. The method includes generating a diagnostic output based on the at least a biological extraction and training data. The method includes generating a comprehensive instruction set associated with the user as a function of the diagnostic output. The method includes receiving at least a user input. The method includes generating at least an alimentary instruction set as a function of the comprehensive instruction set and the at least a user input.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed towards methods and systems for achieving vibrant constitution based on user inputs. In an embodiment, a user input may include an alimentary allocation standard. Information contained within alimentary allocation standard may be utilized to generate an alimentary instruction set including a supplement instruction set and a nutrition instruction set. In an embodiment, supplement instruction set and nutrition instruction set may be optimized to deliver optimal ingredients and aid a user in achieving a vibrant constitution as a function of alimentary allocation standard.

Figure 1:
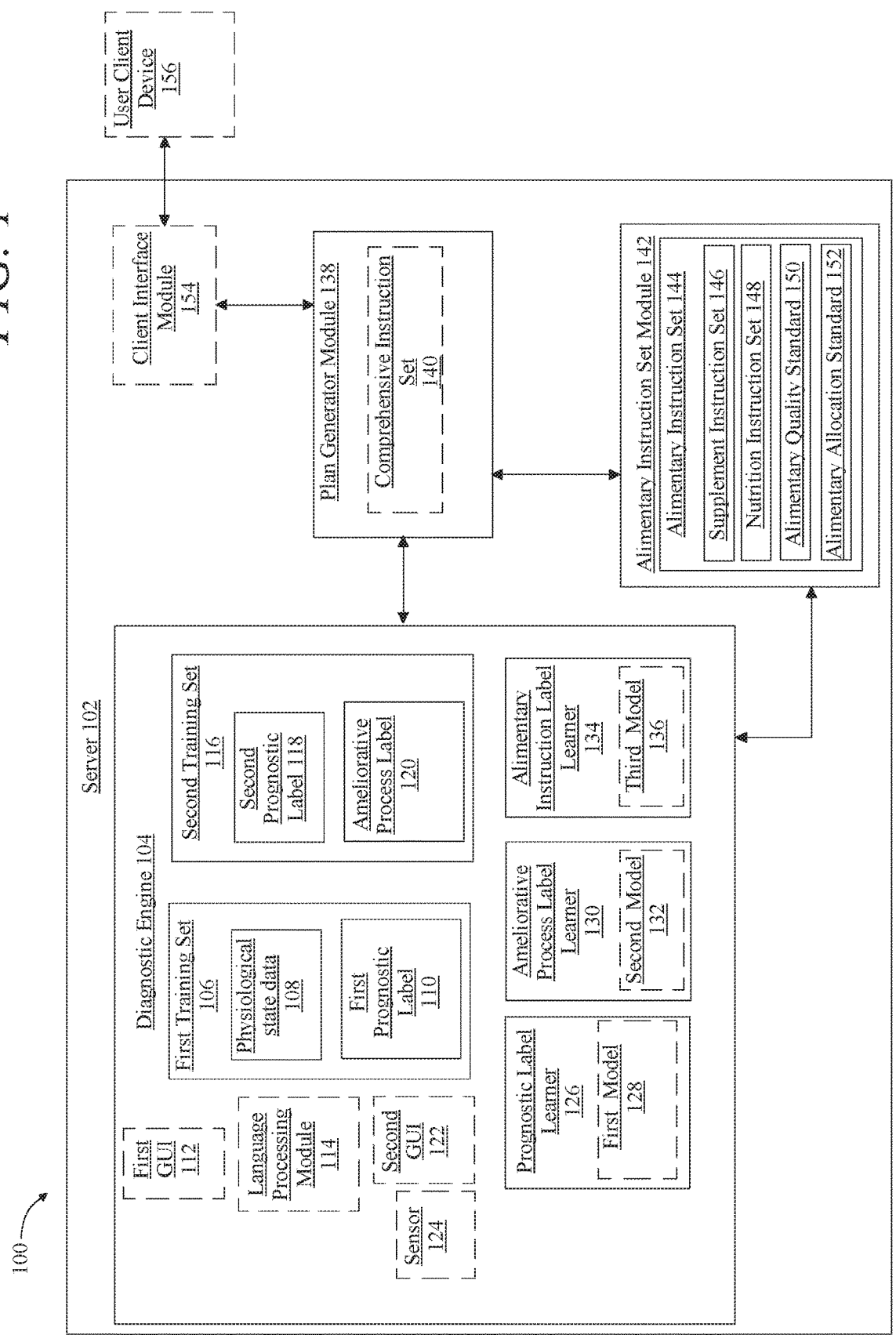
FIG. 1 is a block diagram illustrating an exemplary embodiment of a system for achieving vibrant constitution based on user inputs.

Turning now to FIG. 1, a system 100 for achieving vibrant constitution based on user inputs is illustrated. System 100 includes at least a server 102. At least a server 102 may include any computing device as described herein, including without limitation a microcontroller, microprocessor, digital signal processor (DSP) and/or system on a chip (SoC) as described herein. At least a server 102 may be housed with, may be incorporated in, or may incorporate one or more sensors of at least a sensor. Computing device may include, be included in, and/or communicate with a mobile device such as a mobile telephone or smartphone. At least a server 102 may include a single computing device operating independently, or may include two or more computing device operating in concert, in parallel, sequentially or the like; two or more computing devices may be included together in a single computing device or in two or more computing devices. At least a server 102 with one or more additional devices as described below in further detail via a network interface device. Network interface device may be utilized for connecting a at least a server 102 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 102 may include but is not limited to, for example, a at least a server 102 or cluster of computing devices in a first location and a second computing device or cluster of computing devices in a second location. At least a server 102 may include one or more computing devices dedicated to data storage, security, distribution of traffic for load balancing, and the like. At least a server 102 may distribute one or more computing tasks as described below across a plurality of computing devices of computing device, which may operate in parallel, in series, redundantly, or in any other manner used for distribution of tasks or memory between computing devices. At least a server 102 may be implemented using a "shared nothing" architecture in which data is cached at the worker, in an embodiment, this may enable scalability of system 100 and/or computing device.

Still referring to FIG. 1, system 100 includes a diagnostic engine 104 operating on the at least a server 102, wherein the diagnostic engine 104 configured to receive a first training set including a plurality of first data entries, each first data entry of the plurality of first data entries including at least an element of physiological state data and at least a correlated first prognostic label; receive a second training set including a plurality of second data entries, each second data entry of the plurality of second data entries including at least a second prognostic label and at least a correlated ameliorative process label; receive at least a biological extraction from a user; and generate a diagnostic output based on the at least a biological extraction, the diagnostic output including at least a prognostic label and at least an ameliorative process label using the first training set, the second training set, and the at least a biological extraction. At least a server 102, diagnostic engine 104, and/or one or more modules operating thereon may be designed and/or configured to perform any method, method step, or sequence of method steps in any embodiment described in this disclosure, in any order and with any degree of repetition. For instance, at least a server 102 and/or diagnostic engine 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a server 102 and/or diagnostic engine 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing to refer to FIG. 1, diagnostic engine 104 may be designed and configured to receive training data. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

Still referring to FIG. 1, diagnostic engine 104 may be configured to receive a first training set 106 including a plurality of first data entries, each first data entry of the first training set 106 including at least an element of physiological state data 108 and at least a correlated first prognostic label 110. At least an element of physiological state data 108 may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. Physiological state data 108 may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data 108 may include, without limitation, immune function data such as Interleukine-6 (IL-6), TNF-alpha, systemic inflammatory cytokines, and the like.

Continuing to refer to FIG. 1, physiological state data 108 may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data 108 may include measures of glucose metabolism such as fasting glucose levels and/or hemoglobin A1-C(HbA1c) levels. Physiological state data 108 may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data 108 may include measures of estimated glomerular filtration rate (eGFR). Physiological state data 108 may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data 108 may include anti-nuclear antibody levels. Physiological state data 108 may include aluminum levels. Physiological state data 108 may include arsenic levels. Physiological state data 108 may include levels of fibrinogen, plasma cystatin C, and/or brain natriuretic peptide.

Continuing to refer to FIG. 1, physiological state data 108 may include measures of lung function such as forced expiratory volume, one second (FEV-1) which measures how much air can be exhaled in one second following a deep inhalation, forced vital capacity (FVC), which measures the volume of air that may be contained in the lungs. Physiological state data 108 may include a measurement blood pressure, including without limitation systolic and diastolic blood pressure. Physiological state data 108 may include a measure of waist circumference. Physiological state data 108 may include body mass index (BMI). Physiological state data 108 may include one or more measures of bone mass and/or density such as dual-energy x-ray absorptiometry. Physiological state data 108 may include one or more measures of muscle mass. Physiological state data 108 may include one or more measures of physical capability such as without limitation measures of grip strength, evaluations of standing balance, evaluations of gait speed, pegboard tests, timed up and go tests, and/or chair rising tests.

Still viewing FIG. 1, physiological state data 108 may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data 204 may include one or more measures of psychological function or state, such as without limitation clinical interviews, assessments of intellectual functioning and/or intelligence quotient (IQ) tests, personality assessments, and/or behavioral assessments. Physiological state data 204 may include one or more psychological self-assessments, which may include any self-administered and/ or automatedly computer-administered assessments, whether administered within system 100 and/or via a third-party service or platform.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing modules as described in this disclosure.

With continued reference to FIG. 1, physiological state data 108 may include one or more evaluations of sensory ability, including measures of audition, vision, olfaction, gustation, vestibular function and pain. Physiological state data 108 may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data 108 may include proteomic data, which as used herein, is data describing all proteins produced and/or modified by an organism, colony of organisms, or system of organisms, and/or a subset thereof. Physiological state data 108 may include data concerning a microbiome of a person, which as used herein, includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data 108 of a person, and/or on prognostic labels and/or ameliorative processes as described in further detail below. Physiological state data 108 may include any physiological state data 108, as described above, describing any multicellular organism living in or on a person including any parasitic and/or symbiotic organisms living in or on the persons; non-limiting examples may include mites, nematodes, flatworms, or the like.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Examples of physiological state data 108 described in this disclosure are presented for illustrative purposes only and are not meant to be exhaustive. Persons skilled in the art, upon reviewing the entirety of this disclosure, will be aware of various additional examples of physiological state data 108 that may be used consistently with descriptions of systems and methods as provided in this disclosure.

Continuing to refer to FIG. 1, each element of first training set 106 includes at least a first prognostic label 110. A prognostic label, as described herein, is an element of data identifying and/or describing a current, incipient, or probable future medical condition affecting a person; medical condition may include a particular disease, one or more symptoms associated with a syndrome, a syndrome, and/or any other measure of current or future health and/or heathy aging. At least a prognostic label may be associated with a physical and/or somatic condition, a mental condition such as a mental illness, neurosis, or the like, or any other condition affecting human health that may be associated with one or more elements of physiological state data 108 as described in further detail below. Conditions associated with prognostic labels may include, without limitation one or more diseases, defined for purposes herein as conditions that negatively affect structure and/or function of part or all of an organism. Conditions associated with prognostic labels may include, without limitation, acute or chronic infections, including without limitation infections by bacteria, archaea, viruses, viroids, prions, single-celled eukaryotic organisms such as amoeba, paramecia, trypanosomes, plasmodia, *Leishmania*, and/or fungi, and/or multicellular parasites such as nematodes, arthropods, fungi, or the like. Prognostic labels may be associated with one or more immune disorders, including without limitation immunodeficiencies and/or auto-immune conditions. Prognostic labels may be associated with one or more metabolic disorders. Prognostic labels may be associated with one or more endocrinal disorders. Prognostic labels may be associated with one or more cardiovascular disorders. Prognostic labels may be associated with one or more respiratory disorders. Prognostic labels may be associated with one or more disorders affecting connective tissue. Prognostic labels may be associated with one or more digestive disorders. Prognostic labels may be associated with one or more neurological disorders such as neuromuscular disorders, dementia, or the like. Prognostic labels may be associated with one or more disorders of the excretory system, including without limitation nephrological disorders. Prognostic labels may be associated with one or more liver disorders. Prognostic labels may be associated with one or more disorders of the bones such as osteoporosis. Prognostic labels may be associated with one or more disorders affecting joints, such as osteoarthritis, gout, and/or rheumatoid arthritis. Prognostic labels be associated with one or more cancers, including without limitation carcinomas, lymphomas, leukemias, germ cell tumor cancers, blastomas, and/or sarcomas. Prognostic labels may include descriptors of latent, dormant, and/or apparent disorders, diseases, and/or conditions. Prognostic labels may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with prognostic labels as described in this disclosure.

Still referring to FIG. 1, at least a prognostic label may be stored in any suitable data and/or data type. For instance, and without limitation, at least a prognostic label may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a prognostic label may take; persons skilled in the art, upon reviewing the entirety of this disclosure, will be aware of various forms which may be suitable for use as at least a prognostic label consistently with this disclosure.

With continued reference to FIG. 1, in each first data element of first training set 106, at least a first prognostic label 110 of the data element is correlated with at least an element of physiological state data 108 of the data element. In an embodiment, an element of physiological data is correlated with a prognostic label where the element of physiological data is located in the same data element and/or portion of data element as the prognostic label; for example, and without limitation, an element of physiological data is correlated with a prognostic element where both element of physiological data and prognostic element are contained within the same first data element of the first training set 106. As a further example, an element of physiological data is correlated with a prognostic element where both share a category label as described in further detail below, where each is within a certain distance of the other within an ordered collection of data in data element, or the like. Still further, an element of physiological data may be correlated with a prognostic label where the element of physiological data and the prognostic label share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between physiological data and prognostic labels that may exist in first training set 106 and/or first data element consistently with this disclosure.

In an embodiment, and still referring to FIG. 1, diagnostic engine 104 may be designed and configured to associate at least an element of physiological state data 108 with at least a category from a list of significant categories of physiological state data 108. Significant categories of physiological state data 108 may include labels and/or descriptors describing types of physiological state data 108 that are identified as being of high relevance in identifying prognostic labels. As a non-limiting example, one or more categories may identify significant categories of physiological state data 108 based on degree of diagnostic relevance to one or more impactful conditions and/or within one or more medical or public health fields. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. As an additional example, hemoglobin levels may be useful for identifying elevated testosterone, poor oxygen deliverability, thiamin deficiency, insulin resistance, anemia, liver disease, hypothyroidism, arginine deficiency, protein deficiency, inflammation, and/or nutrient deficiencies. In a further non-limiting example, hematocrit may be useful for identifying dehydration, elevated testosterone, poor oxygen deliverability, thiamin deficiency, insulin resistance, anemia, liver disease, hypothyroidism, arginine deficiency, protein deficiency, inflammation, and/or nutrient deficiencies. Similarly, measures of lipid levels in blood, such as total cholesterol, HDL, LDL, VLDL, triglycerides, LDL-C and/or HDL-C may be recognized as useful in identifying conditions such as poor thyroid function, insulin resistance, blood glucose dysregulation, magnesium deficiency, dehydration, kidney disease, familial hypercholesterolemia, liver dysfunction, oxidative stress, inflammation, malabsorption, anemia, alcohol abuse, diabetes, hypercholesterolemia, coronary artery disease, atherosclerosis, or the like. Persons skilled in the art, upon reviewing the entirety of this disclosure, will be aware of various additional categories of physiological data that may be used consistently with this disclosure.

Still referring to FIG. 1, diagnostic engine 104 may receive the list of significant categories according to any suitable process; for instance, and without limitation, diagnostic engine 104 may receive the list of significant categories from at least an expert. In an embodiment, diagnostic engine 104 and/or a user device connected to diagnostic engine 104 may provide a graphical user interface, which may include without limitation a form or other graphical element having data entry fields, wherein one or more experts, including without limitation clinical and/or scientific experts, may enter information describing one or more categories of physiological data that the experts consider to be significant or useful for detection of conditions; fields in graphical user interface may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to prognostic labels, where experts may enter data describing prognostic labels and/or categories of prognostic labels the experts consider related to entered categories of physiological data; for instance, such fields may include drop-down lists or other pre-populated data entry fields listing currently recorded prognostic labels, and which may be comprehensive, permitting each expert to select a prognostic label and/or a plurality of prognostic labels the expert believes to be predicted and/or associated with each category of physiological data selected by the expert. Fields for entry of prognostic labels and/or categories of prognostic labels may include free-form data entry fields such as text entry fields; as described above, examiners may enter data not presented in pre-populated data fields in the free-form data entry fields. Alternatively or additionally, fields for entry of prognostic labels may enable an expert to select and/or enter information describing or linked to a category of prognostic label that the expert considers significant, where significance may indicate likely impact on longevity, mortality, quality of life, or the like as described in further detail below. Graphical user interface may provide an expert with a field in which to indicate a reference to a document describing significant categories of physiological data, relationships of such categories to prognostic labels, and/or significant categories of prognostic labels. Any data described above may alternatively or additionally be received from experts similarly organized in paper form, which may be captured and entered into data in a similar way, or in a textual form such as a portable document file (PDF) with examiner entries, or the like Still referring to FIG. 1, diagnostic engine 104 may receive the list of significant categories according to any suitable process; for instance, and without limitation, diagnostic engine 104 may receive the list of significant categories from at least an expert. In an embodiment, diagnostic engine 104 and/or a user device connected to diagnostic engine 104 may provide a graphical user interface 112, which may include without limitation a form or other graphical element having data entry fields, wherein one or more experts, including without limitation clinical and/or scientific experts, may enter information describing one or more categories of physiological data that the experts consider to be significant or useful for detection of conditions; fields in graphical user interface may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface 112 or the like may include fields corresponding to prognostic labels, where experts may enter data describing prognostic labels and/or categories of prognostic labels the experts consider related to entered categories of physiological data; for instance, such fields may include drop-down lists or other pre-populated data entry fields listing currently recorded prognostic labels, and which may be comprehensive, permitting each expert to select a prognostic label and/or a plurality of prognostic labels the expert believes to be predicted and/or associated with each category of physiological data selected by the expert. Fields for entry of prognostic labels and/or categories of prognostic labels may include free-form data entry fields such as text entry fields; as described above, examiners may enter data not presented in pre-populated data fields in the free-form data entry fields. Alternatively or additionally, fields for entry of prognostic labels may enable an expert to select and/or enter information describing or linked to a category of prognostic label that the expert considers significant, where significance may indicate likely impact on longevity, mortality, quality of life, or the like as described in further detail below. Graphical user interface 112 may provide an expert with a field in which to indicate a reference to a document describing significant categories of physiological data, relationships of such categories to prognostic labels, and/or significant categories of prognostic labels. Any data described above may alternatively or additionally be received from experts similarly organized in paper form, which may be captured and entered into data in a similar way, or in a textual form such as a portable document file (PDF) with examiner entries, or the like With continued reference to FIG. 1, data information describing significant categories of physiological data, relationships of such categories to prognostic labels, and/or significant categories of prognostic labels may alternatively or additionally be extracted from one or more documents using a language processing module 114. Language processing module 114 may include any hardware and/or software module. Language processing module 114 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 114 may compare extracted words to categories of physiological data recorded at diagnostic engine 104, one or more prognostic labels recorded at diagnostic engine 104, and/or one or more categories of prognostic labels recorded at diagnostic engine 104; such data for comparison may be entered on diagnostic engine 104 as described above using expert data inputs or the like. In an embodiment, one or more categories may be enumerated, to find total count of mentions in such documents. Alternatively or additionally, language processing module 114 may operate to produce a language processing model. Language processing model may include a program automatically generated by diagnostic engine 104 and/or language processing module 114 to produce associations between one or more words extracted from at least a document and detect associations, including without limitation mathematical associations, between such words, and/or associations of extracted words with categories of physiological data, relationships of such categories to prognostic labels, and/or categories of prognostic labels. Associations between language elements, where language elements include for purposes herein extracted words, categories of physiological data, relationships of such categories to prognostic labels, and/or categories of prognostic labels may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of physiological data, a given relationship of such categories to prognostic labels, and/or a given category of prognostic labels; positive or negative indication may include an indication that a given document is or is not indicating a category of physiological data, relationship of such category to prognostic labels, and/or category of prognostic labels is or is not significant. For instance, and without limitation, a negative indication may be determined from a phrase such as "telomere length was not found to be an accurate predictor of overall longevity," whereas a positive indication may be determined from a phrase such as "telomere length was found to be an accurate predictor of dementia," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at diagnostic engine 104, or the like.

Still referring to FIG. 1, language processing module 114 and/or diagnostic engine 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM), HMMs as used herein, are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 114 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 114 may use a corpus of documents to generate associations between language elements in a language processing module 114, and diagnostic engine 104 may then use such associations to analyze words extracted from one or more documents and determine that the one or more documents indicate significance of a category of physiological data, a given relationship of such categories to prognostic labels, and/or a given category of prognostic labels. In an embodiment, diagnostic engine 104 may perform this analysis using a selected set of significant documents, such as documents identified by one or more experts as representing good science, good clinical analysis, or the like; experts may identify or enter such documents via graphical user interface as described above in reference to FIG. 9, or may communicate identities of significant documents according to any other suitable method of electronic communication, or by providing such identity to other persons who may enter such identifications into diagnostic engine 104. Documents may be entered into diagnostic engine 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine 104 may automatically obtain the document using such an identifier, for instance by submitting a request to a database or compendium of documents such as JSTOR as provided by Ithaka Harbors, Inc. of New York.

Continuing to refer to FIG. 1, whether an entry indicating significance of a category of physiological data, a given relationship of such categories to prognostic labels, and/or a given category of prognostic labels is entered via graphical user interface, alternative submission means, and/or extracted from a document or body of documents as described above, an entry or entries may be aggregated to indicate an overall degree of significance. For instance, each category of physiological data, relationship of such categories to prognostic labels, and/or category of prognostic labels may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of physiological data, relationships of such categories to prognostic labels, and/or categories of prognostic labels may be ranked according significance scores, for instance by ranking categories of physiological data, relationships of such categories to prognostic labels, and/or categories of prognostic labels higher according to higher significance scores and lower according to lower significance scores. Categories of physiological data, relationships of such categories to prognostic labels, and/or categories of prognostic labels may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of physiological test or sample collection as described above may indicate that for that type of physiological test or sample collection a first category of physiological data, relationship of such category to prognostic labels, and/or category of prognostic labels is significant with regard to that test, while a second category of physiological data, relationship of such category to prognostic labels, and/or category of prognostic labels is not significant; such indications may be used to perform a significance score for each category of physiological data, relationship of such category to prognostic labels, and/or category of prognostic labels is or is not significant per type of physiological sample, which then may be subjected to ranking, comparison to thresholds and/or elimination as described above.

Still referring to FIG. 1, diagnostic engine 104 may detect further significant categories of physiological data, relationships of such categories to prognostic labels, and/or categories of prognostic labels using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 1, in an embodiment, diagnostic engine 104 may be configured, for instance as part of receiving the first training set 106, to associate at least correlated first prognostic label 110 with at least a category from a list of significant categories of prognostic labels. Significant categories of prognostic labels may be acquired, determined, and/or ranked as described above. As a non-limiting example, prognostic labels may be organized according to relevance to and/or association with a list of significant conditions. A list of significant conditions may include, without limitation, conditions having generally acknowledged impact on longevity and/or quality of life; this may be determined, as a non-limiting example, by a product of relative frequency of a condition within the population with years of life and/or years of able-bodied existence lost, on average, as a result of the condition. A list of conditions may be modified for a given person to reflect a family history of the person; for instance, a person with a significant family history of a particular condition or set of conditions, or a genetic profile having a similarly significant association therewith, may have a higher probability of developing such conditions than a typical person from the general population, and as a result diagnostic engine 104 may modify list of significant categories to reflect this difference.

Still referring to FIG. 1, diagnostic engine 104 is designed and configured to receive a second training set 116 including a plurality of second data entries. Each second data entry of the second training set 116 includes at least a second prognostic label 118; at least a second prognostic label 118 may include any label suitable for use as at least a first prognostic label 110 as described above. Each second data entry of the second training set 116 includes at least an ameliorative process label 120 correlated with the at least a second prognostic label 118, where correlation may include any correlation suitable for correlation of at least a first prognostic label 110 to at least an element of physiological data as described above. As used herein, an ameliorative process label 120 is an identifier, which may include any form of identifier suitable for use as a prognostic label as described above, identifying a process that tends to improve a physical condition of a user, where a physical condition of a user may include, without limitation, any physical condition identifiable using a prognostic label. Ameliorative processes may include, without limitation, exercise programs, including amount, intensity, and/or types of exercise recommended. Ameliorative processes may include, without limitation, dietary or nutritional recommendations based on data including nutritional content, digestibility, or the like. Ameliorative processes may include one or more medical procedures. Ameliorative processes may include one or more physical, psychological, or other therapies. Ameliorative processes may include one or more medications. Persons skilled in the art, upon reviewing the entirety of this disclosure, will be aware of various processes that may be used as ameliorative processes consistently with this disclosure.

Continuing to refer to FIG. 1, in an embodiment diagnostic engine 104 may be configured, for instance as part of receiving second training set 116, to associate the at least second prognostic label 118 with at least a category from a list of significant categories of prognostic labels. This may be performed as described above for use of lists of significant categories with regard to at least a first prognostic label 110. Significance may be determined, and/or association with at least a category, may be performed for prognostic labels in first training set 106 according to a first process as described above and for prognostic labels in second training set 116 according to a second process as described above.

Still referring to FIG. 1, diagnostic engine 104 may be configured, for instance as part of receiving second training set 116, to associate at least a correlated ameliorative process label 120 with at least a category from a list of significant categories of ameliorative process labels 120. In an embodiment, diagnostic engine 104 and/or a user device connected to diagnostic engine 104 may provide a second graphical user interface 122 which may include without limitation a form or other graphical element having data entry fields, wherein one or more experts, including without limitation clinical and/or scientific experts, may enter information describing one or more categories of prognostic labels that the experts consider to be significant as described above; fields in graphical user interface may provide options describing previously identified categories, which may include a comprehensive or near-comprehensive list of types of prognostic labels, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to ameliorative labels, where experts may enter data describing ameliorative labels and/or categories of ameliorative labels the experts consider related to entered categories of prognostic labels; for instance, such fields may include drop-down lists or other pre-populated data entry fields listing currently recorded ameliorative labels, and which may be comprehensive, permitting each expert to select an ameliorative label and/or a plurality of ameliorative labels the expert believes to be predicted and/or associated with each category of prognostic labels selected by the expert. Fields for entry of ameliorative labels and/or categories of ameliorative labels may include free-form data entry fields such as text entry fields; as described above, examiners may enter data not presented in pre-populated data fields in the free-form data entry fields. Alternatively or additionally, fields for entry of ameliorative labels may enable an expert to select and/or enter information describing or linked to a category of ameliorative label that the expert considers significant, where significance may indicate likely impact on longevity, mortality, quality of life, or the like as described in further detail below. Graphical user interface may provide an expert with a field in which to indicate a reference to a document describing significant categories of prognostic labels, relationships of such categories to ameliorative labels, and/or significant categories of ameliorative labels. Such information may alternatively be entered according to any other suitable means for entry of expert data as described above. Data concerning significant categories of prognostic labels, relationships of such categories to ameliorative labels, and/or significant categories of ameliorative labels may be entered using analysis of documents using language processing module 114 or the like as described above.

In an embodiment, and still referring to FIG. 1, diagnostic engine 104 may extract at least a second data entry from one or more documents; extraction may be performed using any language processing method as described above. Diagnostic engine 104 may be configured, for instance as part of receiving second training set 116, to receive at least a document describing at least a medical history and extract at least a second data entry of plurality of second data entries from the at least a document. A medical history document may include, for instance, a document received from an expert and/or medical practitioner describing treatment of a patient; document may be anonymized by removal of one or more patient-identifying features from document. A medical history document may include a case study, such as a case study published in a medical journal or written up by an expert. A medical history document may contain data describing and/or described by a prognostic label; for instance, the medical history document may list a diagnosis that a medical practitioner made concerning the patient, a finding that the patient is at risk for a given condition and/or evinces some precursor state for the condition, or the like. A medical history document may contain data describing and/or described by an ameliorative process label 120; for instance, the medical history document may list a therapy, recommendation, or other ameliorative process that a medical practitioner described or recommended to a patient. A medical history document may describe an outcome; for instance, medical history document may describe an improvement in a condition describing or described by a prognostic label, and/or may describe that the condition did not improve. Prognostic labels, ameliorative process labels 120, and/or efficacy of ameliorative process labels 120 may be extracted from and/or determined from one or more medical history documents using any processes for language processing as described above; for instance, language processing module 114 may perform such processes. As a non-limiting example, positive and/or negative indications regarding ameliorative processes identified in medical history documents may be determined in a manner described above for determination of positive and/or negative indications regarding categories of physiological data, relationships of such categories to prognostic labels, and/or categories of prognostic labels.

With continued reference to FIG. 1, diagnostic engine 104 may be configured, for instance as part of receiving second training set 116, to receiving at least a second data entry of the plurality of second data entries from at least an expert. This may be performed, without limitation using second graphical user interface as described above.

Continuing to refer to FIG. 1, diagnostic engine 104 may be configured to record at least a biological extraction. At least a biological extraction may include any element and/or elements of data suitable for use as at least an element of physiological state data as described above. At least a biological extraction may include a physically extracted sample, which as used herein, includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction may include at least a genetic sample. At least a genetic sample may include a complete genome of a person or any portion thereof. At least a genetic sample may include a DNA sample and/or an RNA sample. At least a biological extraction may include an epigenetic sample, a proteomic sample, a tissue sample, a biopsy, and/or any other physically extracted sample. At least a biological extraction may include an endocrinal sample. As a further non-limiting example, the at least a biological extraction may include a signal from at least a sensor configured to detect physiological data of a user and recording the at least a biological extraction as a function of the signal. At least a sensor 124 may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor 124 may include any electromagnetic sensor, including without limitation electroencephalographic sensors, magnetoencephalographic sensors, electrocardiographic sensors, electromyographic sensors, or the like. At least a sensor 124 may include a temperature sensor. At least a sensor 124 may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor 124 may detect any hematological parameter including blood oxygen level, pulse rate, heart rate, pulse rhythm, blood sugar, and/or blood pressure. At least a sensor 108 may be configured to detect internal and/or external biomarkers and/or readings. At least a sensor 124 may be a part of system 100 or may be a separate device in communication with system 100.

Still referring to FIG. 1, at least a biological extraction may include any data suitable for use as physiological state data as described above, including without limitation any result of any medical test, physiological assessment, cognitive assessment, psychological assessment, or the like. System 100 may receive at least a biological extraction from one or more other devices after performance; system 100 may alternatively or additionally perform one or more assessments and/or tests to obtain at least a biological extraction, and/or one or more portions thereof, on system 100. For instance, at least biological extraction may include or more entries by a user in a form or similar graphical user interface object; one or more entries may include, without limitation, user responses to questions on a psychological, behavioral, personality, or cognitive test. For instance, at least a server 102 may present to user a set of assessment questions designed or intended to evaluate a current state of mind of the user, a current psychological state of the user, a personality trait of the user, or the like; at least a server 102 may provide user-entered responses to such questions directly as at least a biological extraction and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, at least a biological extraction may include assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor.

Still referring to FIG. 1, at least a biological extraction may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure. At least a physiological sample may be added to biological extraction database 200.

With continued reference to FIG. 1, system 100 may include a prognostic label learner 126 operating on the diagnostic engine 104, the prognostic label learner 126 designed and configured to generate the at least a prognostic output as a function of the first training set 106 and the at least a biological extraction. Prognostic label learner 126 may include any hardware and/or software module. Prognostic label learner 126 is designed and configured to generate outputs using machine learning processes. A machine learning process is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

Still referring to FIG. 1, prognostic label learner 126 may be designed and configured to generate at least a prognostic output by creating at least a first machine-learning model 128 relating physiological state data 108 to prognostic labels using the first training set 106 and generating the at least a prognostic output using the first machine-learning model 128; at least a first machine-learning model 128 may include one or more models that determine a mathematical relationship between physiological state data 108 and prognostic labels. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

With continued reference to FIG. 1, machine-learning algorithms may generate prognostic output as a function of a classification of at least a prognostic label. Classification as used herein includes pairing or grouping prognostic labels as a function of a shared commonality. Classification may include for example, groupings, pairings, and/or trends between physiological data and current prognostic label, future prognostic label, and the like. In an embodiment, machine-learning algorithms may examine relationships between a future propensity of a user to develop a condition based on current user physiological data. Machine-learning algorithms may include any and all algorithms as performed by any modules, described herein for prognostic label learner 126. For example, machine-learning algorithms may relate fasting blood glucose readings of a user to user's future propensity to develop diabetes. Machine-learning algorithms may examine precursor condition and future propensity to develop a subsequent disorder. For example, machine-learning algorithms may examine a user diagnosed with chicken pox and user's future propensity to subsequently develop shingles. In yet another non-limiting example, machine-learning algorithms may examine infection with human papillomavirus (HPV) and subsequent cancer diagnosis. Machine-learning algorithms may examine a user's propensity to have recurring attacks of a disease or condition, for example a user with elevated uric acid levels and repeated attacks of gout. Machine-learning algorithms may examine user's genetic predisposition to develop a certain condition or disease. For example, machine-learning algorithms may examine presence of hereditary nonpolyposis colorectal cancer (HNPCC) commonly known as lynch syndrome, and subsequent diagnosis of colorectal cancer. In yet another non-limiting example, machine-learning algorithms may examine presence of abnormal squamous cells and/or abnormal glandular cells in the cervix and subsequent development of cervical cancer. Machine-learning algorithms may examine progression of disease state, for example progression of human immunodeficiency virus (HIV) is marked by decline of CD4+T-Cells, with a count below 200 leading to a diagnosis of acquired immunodeficiency syndrome (AIDS). In yet another non-limiting example, progression of diabetes may be marked by increases of hemoglobin A1C levels with a level of 6.5% indicating a diagnosis of diabetes. Machine-learning algorithms may examine progression of disease by certain age groups. For example, progression of Multiple Sclerosis in users between the age of 20-30 as compared to progression of Multiple Sclerosis in users between the age of 70-80. Machine-learning algorithms may be examining progression of aging such as measurements of telomere length and/or oxidative stress levels and chance mortality risk. Machine-learning algorithms may examine development of co-morbid conditions when a disease or conditions is already present. For example, machine-learning algorithms may examine a user diagnosed with depression and subsequent diagnosis of a co-morbid condition such as migraines, generalized anxiety disorder, antisocial personality disorder, agoraphobia, obsessive-compulsive disorder, drug dependence alcohol dependence, and/or panic disorder. Machine-learning algorithms may examine a user's lifetime chance of developing a certain disease or condition, such as a user's lifetime risk of heart disease, Alzheimer's disease, diabetes and the like. Machine-learning algorithms may be grouped and implemented according to any of the methodologies as described below in reference to FIG. 19.

Continuing to refer to FIG. 1, machine-learning algorithm used to generate first machine-learning model 128 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, prognostic label learner 126 may generate prognostic output using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using first training set 106; the trained network may then be used to apply detected relationships between elements of physiological state data 108 and prognostic labels.

With continued reference to FIG. 1, machine-learning algorithms may include unsupervised processes; unsupervised processes may, as a non-limiting example, be executed by an unsupervised learning module executing on diagnostic engine 104 and/or on another computing device in communication with diagnostic engine 104, which may include any hardware or software module as described in more detail below in reference to FIG. 7. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, prognostic label learner 126 and/or diagnostic engine 104 may perform an unsupervised machine learning process on first training set 106, which may cluster data of first training set 106 according to detected relationships between elements of the first training set 106, including without limitation correlations of elements of physiological state data 108 to each other and correlations of prognostic labels to each other; such relations may then be combined with supervised machine learning results to add new criteria for prognostic label learner 126 to apply in relating physiological state data 108 to prognostic labels. As a non-limiting, illustrative example, an unsupervised process may determine that a first element of physiological data acquired in a blood test correlates closely with a second element of physiological data, where the first element has been linked via supervised learning processes to a given prognostic label, but the second has not; for instance, the second element may not have been defined as an input for the supervised learning process, or may pertain to a domain outside of a domain limitation for the supervised learning process. Continuing the example a close correlation between first element of physiological state data 108 and second element of physiological state data 108 may indicate that the second element is also a good predictor for the prognostic label; second element may be included in a new supervised process to derive a relationship or may be used as a synonym or proxy for the first physiological element by prognostic label learner 126.

Still referring to FIG. 1, diagnostic engine 104 and/or prognostic label learner 126 may detect further significant categories of physiological data, relationships of such categories to prognostic labels, and/or categories of prognostic labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to system 100, prognostic label learner 126 and/or diagnostic engine 104 may continuously or iteratively perform unsupervised machine-learning processes to detect relationships between different elements of the added and/or overall data; in an embodiment, this may enable system 100 to use detected relationships to discover new correlations between known biomarkers, prognostic labels, and/or ameliorative labels and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular prognostic labels and/or suitable ameliorative labels. Use of unsupervised learning may greatly enhance the accuracy and detail with which system may detect prognostic labels and/or ameliorative labels.

With continued reference to FIG. 1, unsupervised processes may be subjected to domain limitations. For instance, and without limitation, an unsupervised process may be performed regarding a comprehensive set of data regarding one person, such as a comprehensive medical history, set of test results, and/or physiological data such as genomic, proteomic, and/or other data concerning that persons. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of physiological data, a group of people having a shared value for an element and/or category of prognostic label, and/or a group of people having a shared value and/or category of ameliorative label; as illustrative examples, cohort could include all people having a certain level or range of levels of blood triglycerides, all people diagnosed with type II diabetes, all people who regularly run between 10 and 15 miles per week, or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 1, prognostic label learner 126 may alternatively or additionally be designed and configured to generate at least a prognostic output by executing a lazy learning process as a function of the first training set 106 and the at least a biological extraction; lazy learning processes may be performed by a lazy learning module executing on diagnostic engine 104 and/or on another computing device in communication with diagnostic engine 104, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at a prognostic label associated with biological extraction, using first training set 106. As a non-limiting example, an initial heuristic may include a ranking of prognostic labels according to relation to a test type of at least a biological extraction, one or more categories of physiological data identified in test type of at least a biological extraction, and/or one or more values detected in at least a biological extraction; ranking may include, without limitation, ranking according to significance scores of associations between elements of physiological data and prognostic labels, for instance as calculated as described above. Heuristic may include selecting some number of highest-ranking associations and/or prognostic labels. Prognostic label learner 126 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate prognostic outputs as described in this disclosure, including without limitation lazy learning applications of machine-learning algorithms as described in further detail below.

Continuing to refer to FIG. 1, prognostic label learner 126 may generate a plurality of prognostic labels having different implications for a particular person. For instance, where the at least a physiological sample includes a result of a dexterity test, a low score may be consistent with amyotrophic lateral sclerosis, Parkinson's disease, multiple sclerosis, and/or any number of less sever disorders or tendencies associated with lower levels of dexterity. In such a situation, prognostic label learner 126 and/or diagnostic engine 104 may perform additional processes to resolve ambiguity. Processes may include presenting multiple possible results to a medical practitioner, informing the medical practitioner that one or more follow-up tests and/or physiological samples are needed to further determine a more definite prognostic label. Alternatively or additionally, processes may include additional machine learning steps; for instance, where reference to a model generated using supervised learning on a limited domain has produced multiple mutually exclusive results and/or multiple results that are unlikely all to be correct, or multiple different supervised machine learning models in different domains may have identified mutually exclusive results and/or multiple results that are unlikely all to be correct. In such a situation, prognostic label learner 126 and/or diagnostic engine 104 may operate a further algorithm to determine which of the multiple outputs is most likely to be correct; algorithm may include use of an additional supervised and/or unsupervised model. Alternatively or additionally, prognostic label learner 126 may perform one or more lazy learning processes using a more comprehensive set of user data to identify a more probably correct result of the multiple results. Results may be presented and/or retained with rankings, for instance to advise a medical professional of the relative probabilities of various prognostic labels being correct; alternatively or additionally, prognostic labels associated with a probability of correctness below a given threshold and/or prognostic labels contradicting results of the additional process, may be eliminated. As a non-limiting example, an endocrinal test may determine that a given person has high levels of dopamine, indicating that a poor pegboard performance is almost certainly not being caused by Parkinson's disease, which may lead to Parkinson's being eliminated from a list of prognostic labels associated with poor pegboard performance, for that person. Similarly, a genetic test may eliminate Huntington's disease, or another disease definitively linked to a given genetic profile, as a cause. Persons skilled in the art, upon reviewing the entirety of this disclosure, will be aware of various ways in which additional processing may be used to determine relative likelihoods of prognostic labels on a list of multiple prognostic labels, and/or to eliminate some labels from such a list. Prognostic output 712 may be provided to user output device as described in further detail below.

Still referring to FIG. 1, diagnostic engine 104 includes an ameliorative process label learner 130 operating on the diagnostic engine 104, the ameliorative process label learner 130 designed and configured to generate the at least an ameliorative output as a function of the second training set 116 and the at least a prognostic output. Ameliorative process label learner 130 may include any hardware or software module suitable for use as a prognostic label learner 126 as described above. Ameliorative process label learner 130 is a machine-learning module as described above; ameliorative process label learner 130 may perform any machine-learning process or combination of processes suitable for use by a prognostic label learner 126 as described above. For instance, and without limitation, and ameliorative process label learner 130 may be configured to create a second machine-learning model 132 relating prognostic labels to ameliorative labels using the second training set 116 and generate the at least an ameliorative output using the second machine-learning model 132; second machine-learning model 132 may be generated according to any process, process steps, or combination of processes and/or process steps suitable for creation of first machine learning model. In an embodiment, ameliorative process label learner 130 may use data from first training set 106 as well as data from second training set 116; for instance, ameliorative process label learner 130 may use lazy learning and/or model generation to determine relationships between elements of physiological data, in combination with or instead of prognostic labels, and ameliorative labels. Where ameliorative process label learner 130 determines relationships between elements of physiological data and ameliorative labels directly, this may determine relationships between prognostic labels and ameliorative labels as well owing to the existence of relationships determined by prognostic label learner 126.

With continued reference to FIG. 1, diagnostic engine 104 may include an alimentary instruction label learner 134 operating on the diagnostic engine 104, the alimentary instruction label learner 134 designed and configured to generate at least an alimentary data output as a function of the second training set 116 and the at least a prognostic output. Alimentary instruction label learner 134 may include any hardware or software module suitable for use as a prognostic label learner 126 as described above. Alimentary instruction label learner 134 may include a machine-learning module as described above; alimentary instruction label learner 134 may perform any machine-learning process or combination of processes suitable for use by a prognostic label learner 126 as described above. For instance, and without limitation, and alimentary instruction label learner 134 may be configured to create a third machine-learning model 136 relating prognostic labels to alimentary labels using the second training set 132 and generate the at least an alimentary data output using the third machine-learning model 136; third machine-learning model 136 may be generated according to any process, process steps, or combination of processes and/or process steps suitable for creation of first machine learning model. In an embodiment, alimentary instruction label learner 134 may use data from first training set 106 as well as data from second training set 116; for instance, alimentary instruction label learner 134 may use lazy learning and/or model generation to determine relationships between elements of physiological data, in combination with or instead of prognostic labels, and alimentary labels, which may include, without limitation, a subset of ameliorative labels corresponding to alimentary processes. Where alimentary instruction label learner 134 determines relationships between elements of physiological data and alimentary labels directly, this may determine relationships between prognostic labels and alimentary labels as well owing to the existence of relationships determined by prognostic label learner 126.

With continued reference to FIG. 1, system 100 includes a plan generator module 138 operating on the at least a server 102. Plan generator module 138 may include any suitable hardware or hardware module. In an embodiment, plan generator module 138 is designed and configured to generate a comprehensive instruction set associated with the user as a function of the diagnostic output. In an embodiment, comprehensive instruction set 140 is a data structure containing instructions to be provided to the user to explain the user's current prognostic status, as reflected by one or more prognostic outputs and provide the user with a plan based on the at least an ameliorative output, to achieve that. In an embodiment, comprehensive instruction set 140 may be generated based on at least an informed advisor output. Comprehensive instruction set 140 may include but is not limited to a program, strategy, summary, recommendation, or any other type of interactive platform that may be configured to comprise information associated with the user, an applicable verified external source, and one or more outputs derived from the analyses performed on the extraction from the user. Comprehensive instruction set 140 may describe to a user a future prognostic status to aspire to. Comprehensive instruction set 140 may reflect analyses and diagnostics associated with a user.

With continued reference to FIG. 1, system 100 includes an alimentary instruction set generator module 142 operating on the at least a server 102. Alimentary instruction set module 142 may include any suitable hardware or hardware module. In an embodiment, alimentary instruction set module is designed and configured to receive at least a user input and generate as a function of the comprehensive instruction set and the at least a user input an alimentary instruction set associated with the user. In an embodiment, alimentary instruction set 144 is a data structure containing a solution and/or suggestion to nourishment requirements or constitutional or chemical deficiencies. Alimentary instruction set 144 may be generated as a function of comprehensive instruction set 140. For example, comprehensive instruction set 140 that contains a recommendation to increase iron intake based on at least a biological extraction from a user reflecting anemia, may be utilized to generate an alimentary instruction set that includes a suggestion for a user to increase consumption of organ meats and green leafy vegetables. In yet another non-limiting example, alimentary instruction set 144 may contain a component seeking to remedy a B vitamin deficiency of a user based on a comprehensive instruction set 140 showing blood levels of B vitamins below normal acceptable values. Alimentary instruction set may include suggested foods, meals, ingredients, medications, nutrients, supplements, vitamins, homeopathic remedies, and the like that a user may consider consuming. For example, a user with a diagnostic output such as hypothyroidism may be recommended to consume three brazil nuts each week and to consume a selenium supplement. In yet another non-limiting example, a user with ulcerative colitis may be recommended to consume a grain free paleo diet. In yet another non-limiting example, alimentary instruction set 144 may include a recommendation for a supplement such as ubiquinol for a user with high blood pressure or a methylated b-complex for a user with a 5,10-methylenetetrahydrofolate mutation (MTHFR).

With continued reference to FIG. 1, alimentary instruction set module 142 may generate at least an alimentary instruction set including at least a supplement instruction set 146 and at least a nutrition instruction set 148. Supplement instruction set 146 as used herein, is a data structure containing instructions and/or recommendations to a user as to one or more supplements that a user may want to consider taking. Supplements may include any products intended to supplement a user's diet. Supplements may include products consumed by a user that contain a dietary ingredient. Dietary ingredients may include any vitamin, mineral, nutrient, homeopathic, amino acid, herb, botanical, nutraceutical, enzyme, health food, medical food and the like. Supplements may contain dietary ingredients sourced from food, synthesized in a laboratory, and/or sourced in combination. Supplements may include for example, a multi-vitamin, fish oil, Vitamin D, *Lactobacillus acidophilus, Saccharomyces boulardii*, Vitamin C, Cranberry extract, pea protein powder, and the like. Supplements may be available to a user without a prescription such as for example, a berberine product sold at a health food store. Supplements may be available to a user with a prescription, such as for example subcutaneous cyanocobalamin injections available at a compounding pharmacy or an intravenous Vitamin C drop available at a functional medicine doctor's office. Nutrition instruction set 148 as used herein, is a data structure containing instructions to the user including one or more recommendations as to dietary and/or nutritional recommendations; such recommendations may include, without limitation nutritional instructions, nutritional content, digestibility, sample meal plans, foods and/or food groups to consume or avoid, dietary recommendations that may reverse a deficiency of a nutrient, ideal nutrition choices for a user and the like. Nutrition instruction set 148 may include for example a particular recommended diet for a user, preferred foods or meals for a user. For example, nutrition instruction set 148 may recommend a user follow the Swank diet for a user with multiple sclerosis or recommend the autoimmune protocol diet for a user with rheumatoid arthritis.

With continued reference to FIG. 1, alimentary instruction set module 142 may be configured to receive at least a user input. At least a user input as used herein, is any element of data received from a user including for example one or more user selections, instructions, or the like. At least a user input may be input via a user device, input and/or output components as described herein. The at least a user input may include an alimentary quality standard. Alimentary quality standard as used herein, is a user preference and/or need as to the quality of the solution and/or suggestion to nourishment or constitutional or chemical deficiencies contained within an alimentary instruction set. Alimentary quality standard may include a user's preference for a particular quality of food, meals, and/or ingredients contained within an alimentary instruction set such as a preference for organic produce, or free-range poultry or a certain grade or level of quality supplement. Alimentary quality standard may include a user's preference for locally grown or natural products, such as a preference for wild caught Alaskan salmon or non-genetically modified almonds. Alimentary quality standard may include a user's preference for a particular quality or level of supplement. For example, a user may prefer supplements and/vitamins that are pharmaceutical grade in excess of 99% purity and not containing any binders, fillers, excipients, dyes or unknown substances. A user may have a preference for supplements to be manufactured in a particular way such as for example, a supplement that has been manufactured under certified good manufacturing practices (cGMP) or that may contain a United States Pharmacopeia (USP) seal. Alimentary quality standard may include for example, a user preference to avoid a food or supplement that may contain certain ingredients such as a preference to avoid anything with monosodium glutamate (MSG) or sodium benzoate.

With continued reference to FIG. 1, at least a user input may include an alimentary allocation standard. Alimentary allocation standard as used herein, is a user input containing a total amount of resources that a user is willing to devote to an alimentary instruction set. Resources may include a budget, and/or total dollar amount that a user may devote to an alimentary instruction set for a specific period of time. For example, a user may enter a total budget amount that a user is willing to spend on himself or herself for a month's worth of food and supplements. In yet another non-limiting example, a user may enter a total nutrition budget for a week or a total supplement budget for a year. In an embodiment, a user may enter a certain percentage of alimentary allocation standard that user seeks to allocate to nutrition and a certain percentage of alimentary allocation standard that user seeks to allocate to supplements. For example, a user may seek to allocate thirty percent of alimentary allocation standard to supplements and seventy percent of alimentary allocation standard to nutrition. In an embodiment, user may allocate a certain dollar amount of total alimentary allocation standard to supplements and a certain dollar amount of total alimentary allocation standard to nutrition. In an embodiment, alimentary instruction set 144 may be optimized as a function of alimentary allocation standard to select nutrition and/or supplements that will best aid a user in achieving vibrant constitution while staying within limits of alimentary allocation standard.

With continued reference to FIG. 1, alimentary instruction set module 142 may generate at least an alimentary instruction set including at least a supplement instruction set 146 and at least a nutrition instruction set 148 as a function of the alimentary allocation standard and the comprehensive instruction set. For example, a user with a comprehensive instruction set that includes a diagnostic such as fibromyalgia may input an alimentary allocation standard containing a total budget for nutrition and supplements for a month; alimentary instruction set may then utilize comprehensive instruction set of fibromyalgia and alimentary allocation standard to generate an alimentary instruction set containing at least a nutrition instruction set 148 and a supplement instruction set 146 as a function of user's fibromyalgia and user's monthly budget. Alimentary instruction set module 142 may utilize user's alimentary allocation standard to generate a nutrition instruction set 148 and a supplement instruction set 146 appropriately. For example, a portion of user's budget may be allocated to a supplement that will aid in reducing user's neuropathic pain experienced due to fibromyalgia, and other portion of user's budget may be allocated to a dietary plan that includes a grain free diet designed to further assist in eliminating user's pain. In such an instance, certain foods may be selected and/or eliminated that will fit within user's allocated budget while still assisting user in consuming a grain free diet. For example, user may be recommended to consume a non-organic apple and simply avoid eating apple core where most of the pesticides reside as opposed to spending more money to consume an organic apple. In yet another non-limiting example, user may be instructed to purchase more expensive free range chicken as compared to conventionally grown chicken that have been fed antibiotics and kept in chicken pens, and to purchase and consume conventionally grown fruits and vegetables that are not listed on the "dirty dozen" list of conventionally grown produce that are known to contain high levels of pesticides such as strawberries, spinach, kale, nectarines, apples, grapes, peaches, cherries, pears, tomatoes, celery, and potatoes.

With continued reference to FIG. 1, alimentary instruction set generator module may generate the at least a supplement instruction set 146 as a function of the at least a nutrition instruction set 148. In an embodiment, nutrition instruction set 148 may contain nutritional and/or dietary recommendations for a user including for example, a month's worth of sample meals that a user may prepare and consume. Such information may then be utilized to generate a supplement instruction set 146 as a function of the nutrition instruction set 148. For example, a nutrition instruction set 148 may include meals designed around a user consuming a paleo diet to reduce a user's symptoms and flares from ulcerative colitis. Supplement instruction set 146 may be generated from nutrition instruction to expand upon and/or fill in the gaps where the nutrition may be lacking. In such an instance, supplement instruction set 146 may contain a recommendation for user to consume a Vitamin B Complex supplement since grains that have been eliminated on paleo diet are often a source of B vitamins for a user. In an embodiment, supplement instruction set 146 may be generated from nutrition instruction set 148 utilizing user alimentary allocation standard. For example, nutrition instruction set 148 may have a greater budget allotment when a user has an optimally functioning gut and is able to absorb nutrients and vitamins from food, whereas for example a user with a digestive disorder such as malabsorption may have a greater budget allotment to supplements such as when a user may be unable to absorb vitamins and nutrients from the diet and may need to supplement with digestive enzymes, Vitamin D, and glutamine to help repair the gut. In an embodiment, alimentary allocation standard may be allotted to nutrition instruction set 148 and supplement instruction set 146 by using a loss function, variables database and/or interchange database as described in more detail below. For example, a user with a certain alimentary allocation standard may include an instruction to consume an inexpensive supplement such as zinc that costs mere pennies each day to consume versus consuming oysters three days each week where each individual oyster may cost several dollars each.

With continued reference to FIG. 1, supplement instruction set 146 may be generated as a result of a user preference as to a nutrition instruction set 148. For example, a user may indicate an unwillingness to follow a nutrition instruction set 148 or a user may be unable to access ingredients and/or foods contained within a nutrition instruction set 148. For example, a nutrition instruction set 148 that instructs a user to consume cruciferous vegetables such as broccoli, cabbage, kale, and Brussel sprouts to aid a user with a cancer mutation gene in eliminating harmful cancer causing estrogens such as estrone (E3) may instead be generated as a supplement instruction set 146 with a recommendation for a user to consume a supplement containing indole-3-carbinol which is the main extract found in cruciferous vegetables that binds to and eliminates E3 because of user's dislike or aversion to consuming cruciferous vegetables. This may be done by consulting alimentary instruction label learner and interchange database as described below in more detail in reference to FIGS. 9-10.

With continued reference to FIG. 1, alimentary instruction set generator module may generate the at least a nutrition instruction set 148 as a function of the at least a supplement instruction set. In an embodiment, supplement instruction set 146 may inform nutrition instruction set 148 as to what foods should be consumed and/or avoided based on supplementation. For example, a supplement instruction set 146 containing a recommendation for a user to consume a Vitamin C supplement may be utilized to generate a nutrition instruction that does not contain a large amount of Vitamin C rich foods such as cantaloupe, kiwi, and *papaya* so as to not cause side effects from too large a dose of Vitamin C such as gas, diarrhea, nausea, and loose stools. In yet another non-limiting example, supplement instruction set 146 may be utilized to generate nutrition instruction set 148 as a function of supplements contained within supplement instruction set 146, which may need to be consumed with certain foods for better absorption and/or in combination with other nutrient that may be obtained from dietary sources. For example, a supplement containing a fat soluble vitamin such as Vitamin K, Vitamin E, Vitamin D, and/or Vitamin C may be utilized to generate a nutrition instruction set 148 that recommends consumption of fats in the diet such as olive oil, avocado, and coconut oil to best absorb fat soluble vitamins. In yet another non-limiting example, a nutrition instruction set 148 may be generated as a function of a supplement instruction set 146 such as when supplementation with a certain ingredient may require consumption of another ingredient. For example, a supplement instruction set 146 containing zinc may be utilized to generate a nutrition instruction set 148 that contains recommendations for consumption of copper containing foods as zinc supplementation alone causes the body to excrete copper. Similarly a supplementation instruction set containing Vitamin D may be utilized to generate a nutrition instruction set 148 that contains recommendations for consumption of Vitamin K containing foods as Vitamin K plays a crucial role in helping to absorb Vitamin D.

With continued reference to FIG. 1, nutrition instruction set 148 may be generated as a function of supplement instruction set 146 because of a user preference to obtain some nutrients through diet and others through supplementation. For example, a user may need to consume Omega 3 fish oils for eye health and may dislike Omega 3 capsules because of a fishy taste they produce in the mouth. In such an instance, supplement instruction set 146 may not contain a recommendation for Omega 3 fish oils and instead nutrition instruction set 148 may be generated to recommend adequate amounts of Omega 3 fish oils through dietary sources such as recommendation to consume mackerel, salmon, seabass, oysters, sardines, and trout. In yet another non-limiting example, a user with osteoporosis may prefer to consume calcium rich foods such as spinach, broccoli, and milk as opposed to consuming calcium supplement because of previous experiences with constipation from calcium supplements. In an embodiment, nutrition instruction set 148 may be generated from supplement instruction set 146 as a function of availability of certain products and supplements in different geographical areas. For example, a user in Honolulu, Hawaii may be unable to obtain a bromelain supplement whereby a nutrition instruction set 148 may be generated to recommend user to consume plenty of fresh pineapples that contain bromelain instead and are found in abundance in Hawaii. Similarly, a user located in Nebraska may be unable to find fresh pineapple in the winter but may be able to easily find a bromelain supplement.

With continued reference to FIG. 1, nutrition instruction set 148 may be generated as a function of supplement instruction set 146 and alimentary allocation standard. For example, alimentary instruction set module 142 may analyze differing costs between a certain ingredient obtained through supplementation and the same ingredient obtained through diet and generate a supplement instruction set 146 and a nutrition instruction set 148 as a function of the alimentary allocation standard that may still optimize a user's nutrition. For example, supplementation with Vitamin C may be relatively inexpensive as compared to dietary sources such as organic bell peppers and organic oranges while supplementation with fish oil may relatively expensive as compared to dietary sources such as canned sardines and canned salmon. In yet another non-limiting example, consuming nutrition may be optimized based on alimentary allocation standard such as by recommending consumption of non-organic produce that is not found on the "Dirty Dozen" list or consuming wild caught canned fish such as wild salmon and tuna that is less expensive than fresh caught wild salmon or wild tuna.

With continued reference to FIG. 1, alimentary instruction set generator module 142 may perform machine-learning algorithms using a loss function analysis utilizing linear regression to generate alimentary instruction set including supplement instruction set 146 and/or nutrition instruction set 148. In an embodiment, alimentary instruction set generator module 142 may compare one or more user specific inputs to a mathematical expression representing an optimal combination of user specific inputs and/or optimal alimentary instruction sets. Mathematical expression may include a linear combination of variables, weighted by coefficients representing relative importance of each variables in generating an optimal self-fulfillment action. For instance, a variable such as food quality such as importance of organic items versus nonorganic items of an alimentary instruction set may be multiplied by a first coefficient representing the importance of organic food standards, a second user input such as total cost of an alimentary instruction set may be multiplied by a second coefficient representing the importance of cost, a degree of variance from an alimentary instruction set instruction set may be represented as another parameter, which may be multiplied by another coefficient representing the importance of that variable, a degree of variance from a preference for fresh or frozen ingredients may be multiplied by an additional coefficient representing an importance of that variable, and/or a variable representing a degree of variance from one or more supplement quality standards may be provided a coefficient representing the importance of such a variance; persons skilled in the art, upon reviewing the entirety of this disclosure, will be aware of different variables that may be weighted by various coefficients. Use of a linear combination is provided only as an illustrative example; other mathematical expressions may alternatively or additionally be used, including without limitation higher-order polynomial expressions or the like.

Still viewing FIG. 1, mathematical expression may represent a loss function, where a "loss function" is an expression an output of which an optimization algorithm minimizes to generate an optimal result. As a non-limiting example, self-fulfillment learner may calculate variables of each of a plurality of alimentary instruction sets and/or user inputs, calculate an output of mathematical expression using the variables, and select an alimentary instruction set that produces an output having the lowest size, according to a given definition of "size," of the set of outputs representing each of the plurality of alimentary instruction sets; size may, for instance, included absolute value, numerical size, or the like. Selection of different loss functions may result in identification of different alimentary instruction sets as generating minimal outputs; for instance, where organic ingredients is associated in a first loss function with a large coefficient or weight, an alimentary instruction set having a small coefficient or weight for organic ingredients may minimize the first loss function, whereas a second loss function wherein organic ingredients has a smaller coefficient but degree of variance from supplement quality which has a larger coefficient may produce a minimal output for a different alimentary instruction set having a larger organic ingredients but more closely hewing to a supplement quality.

Alternatively or additionally, and still referring to FIG. 1, each alimentary instruction set may be represented by a mathematical expression having the same form as mathematical expression; alimentary instruction set module 142 may compare the former to the latter using an error function representing average difference between the two mathematical expressions. Error function may, as a non-limiting example, be calculated using the average difference between coefficients corresponding to each variable. An alimentary instruction set having a mathematical expression minimizing the error function may be selected, as representing an optimal expression of relative importance of variables to a system or user. In an embodiment, error function and loss function calculations may be combined; for instance, an alimentary instruction set resulting in a minimal aggregate expression of error function and loss function, such as a simple addition, arithmetic mean, or the like of the error function with the loss function, may be selected, corresponding to an option that minimizes total variance from optimal variables while simultaneously minimizing a degree of variance from a set of priorities corresponding to alimentary instruction set variables. Coefficients of mathematical expression and/or loss function may be scaled and/or normalized; this may permit comparison and/or error function calculation to be performed without skewing by varied absolute quantities of numbers.

Still referring to FIG. 1, mathematical expression and/or loss function may be provided by receiving one or more user commands. For instance, and without limitation, a graphical user interface may be provided to user with a set of sliders or other user inputs permitting a user to indicate relative and/or absolute importance of each variable to the user. Sliders or other inputs may be initialized prior to user entry as equal or may be set to default values based on results of any machine-learning processes or combinations thereof as described in further detail below.

With continued reference to FIG. 1, mathematical expression and/or loss function may be generated using a machine learning to produce loss function: i.e., regression. Mathematical expression and/or loss function be user-specific, using a training set composed of past user selections; may be updated continuously. Mathematical expression and/or loss function may initially be seeded using one or more user entries as above. User may enter a new command changing mathematical expression, and then subsequent user selections may be used to generate a new training set to modify the new expression.

With continued reference to FIG. 1, mathematical expression and/or loss function may be generated using machine learning using a multi-user training set. Training set may be created using data of a cohort of persons having similar demographic, religious, health, and/or lifestyle characteristics to user. This may alternatively or additionally be used to seed a mathematical expression and/or loss function for a user, which may be modified by further machine learning and/or regression using subsequent user selections of alimentary provision options.

With continued reference to FIG. 1, alimentary instruction set module 142 may generate a loss function of user specific variables and minimize the loss function. Alimentary instruction set module 142 may generate alimentary instruction set 144 utilizing loss function analysis. Loss function analysis may measure changes in predicted values versus actual values, known as loss or error. Loss function analysis may utilize gradient descent to learn the gradient or direction that a cost analysis should take in order to reduce errors. Loss function analysis algorithms may iterate to gradually converge towards a minimum where further tweaks to the parameters produce little or zero changes in the loss or convergence by optimizing weights utilized by machine learning algorithms. Loss function analysis may examine the cost of the difference between estimated values, to calculate the difference between hypothetical and real values. Alimentary instruction set module 142 may utilize variables to model relationships between past interactions between a user and system 100 and alimentary instruction sets. In an embodiment loss function analysis may utilize variables that may impact user interactions and/or alimentary instruction sets. Loss function analysis may be user specific so as to create algorithms and outputs that are customize to variables for an individual user. Variables may include any of the variables as described below in more detail in reference to FIGS. 16-20. Variables may include for example, ingredient quality as described below in more detail in reference to FIG. 18. Variable may include for example, product ingredient as described below in more detail in reference to FIG. 18. Variable may include for example, impact on alimentary allocation standard as described in more detail in reference to FIG. 18. User behaviors and user past responses may be utilized as training data to generate outputs. Variables contained within loss function analysis may be weighted and given different numerical scores. Variables may be stored and utilized to predict subsequent outputs. Outputs may seek to predict user behavior and past user interactions with system 100 and self-fulfillment instruction sets.

With continued reference to FIG. 1, system 100 may include a client-interface module 154. Client-interface module 154 may include any suitable hardware or software module. Client-interface module 154 may designed and configured to transmit comprehensive instruction set 140 to at least a user client device 156 associated with the user. A user client device 156 may include, without limitation, a display in communication with diagnostic engine 104; display may include any display as described herein. A user client device 156 may include an addition computing device, such as a mobile device, laptop, desktop computer, or the like; as a non-limiting example, the user client device 156 may be a computer and/or workstation operated by a medical professional. Output may be displayed on at least a user client device 156 using an output graphical user interface; output graphical user interface may display an alimentary instruction set 144.

Figure 2:
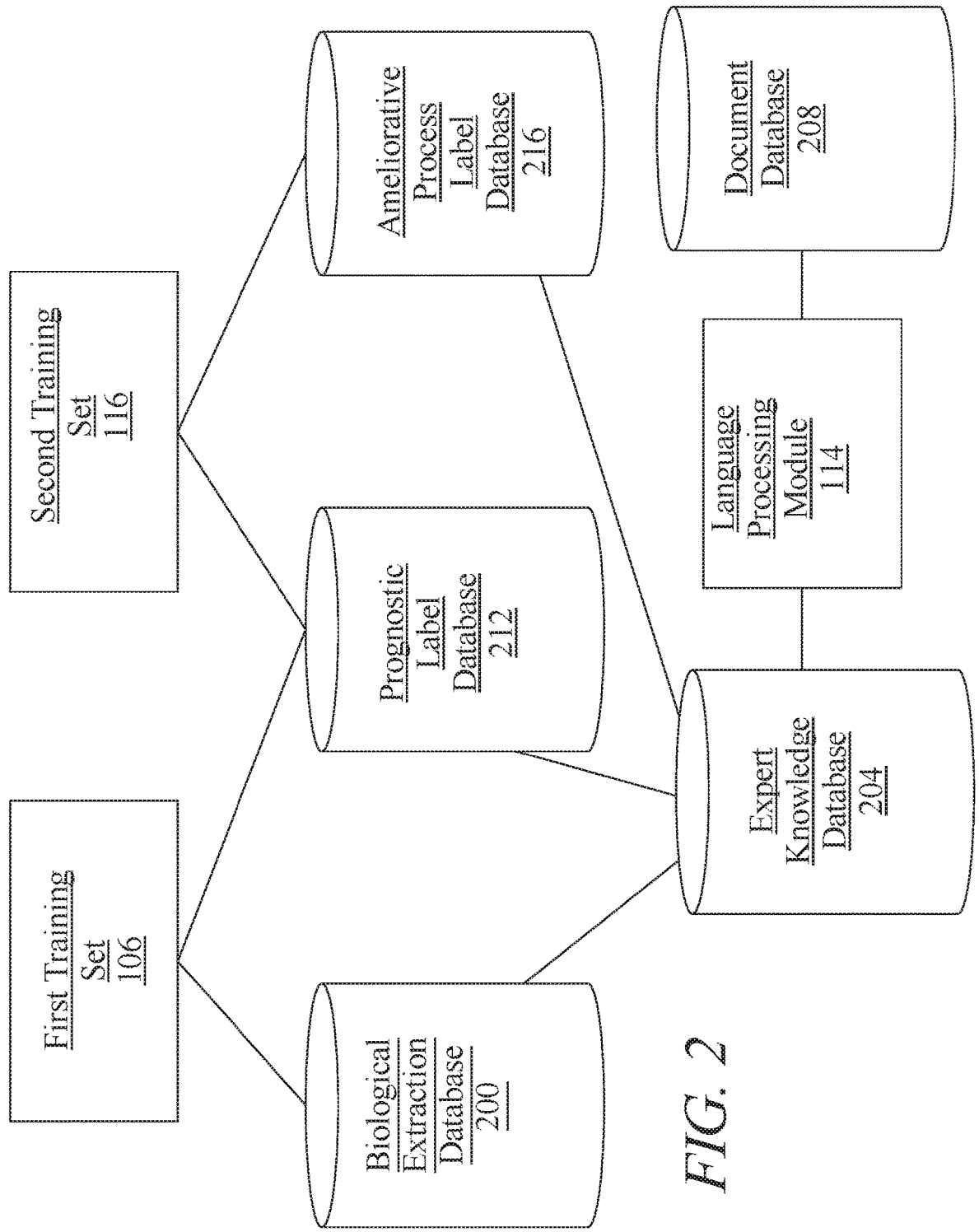
FIG. 2 is a block diagram illustrating embodiments of data storage facilities for use in disclosed systems and methods.

Referring now to FIG. 2, data incorporated in first training set 106 and/or second training set 116 may be incorporated in one or more databases. As a non-limiting example, one or elements of physiological state data may be stored in and/or retrieved from a biological extraction database 200. A biological extraction database 200 may include any data structure for ordered storage and retrieval of data, which may be implemented as a hardware or software module. A biological extraction database 200 may be implemented, without limitation, as a relational database, a key-value retrieval datastore such as a NOSQL database, or any other format or structure for use as a datastore that a person skilled in the art would recognize as suitable upon review of the entirety of this disclosure. A biological extraction database 200 may include a plurality of data entries and/or records corresponding to elements of physiological data as described above. Data entries and/or records may describe, without limitation, data concerning particular physiological samples that have been collected; entries may describe reasons for collection of samples, such as without limitation one or more conditions being tested for, which may be listed with related prognostic labels. Data entries may include prognostic labels and/or other descriptive entries describing results of evaluation of past physiological samples, including diagnoses that were associated with such samples, prognoses and/or conclusions regarding likelihood of future diagnoses that were associated with such samples, and/or other medical or diagnostic conclusions that were derived. Such conclusions may have been generated by system 100 in previous iterations of methods, with or without validation of correctness by medical professionals. Data entries in a biological extraction database 200 may be flagged with or linked to one or more additional elements of information, which may be reflected in data entry cells and/or in linked tables such as tables related by one or more indices in a relational database; one or more additional elements of information may include data associating a physiological sample and/or a person from whom a physiological sample was extracted or received with one or more cohorts, including demographic groupings such as ethnicity, sex, age, income, geographical region, or the like, one or more common diagnoses or physiological attributes shared with other persons having physiological samples reflected in other data entries, or the like. Additional elements of information may include one or more categories of physiological data as described above. Additional elements of information may include descriptions of particular methods used to obtain physiological samples, such as without limitation physical extraction of blood samples or the like, capture of data with one or more sensors, and/or any other information concerning provenance and/or history of data acquisition. Persons skilled in the art, upon reviewing the entirety of this disclosure, will be aware of various ways in which data entries in a biological extraction database 200 may reflect categories, cohorts, and/or populations of data consistently with this disclosure.

With continued reference to FIG. 2, diagnostic engine 104 may be configured to have a feedback mechanism. In an embodiment, diagnostic engine 104 may be configured to receive a first training set 200 and/or a second training set 220 generated by system 100. For example, data about a user that has been previously been analyzed by diagnostic engine 104 may be utilized in algorithms by first model 240 and/or second model 248. Such algorithms may be continuously updated as a function of such data. In yet another embodiment, data analyzed by language processing module 216 may be utilized as part of training data generating algorithms by first model 240 and/or second model 248 and/or any other machine learning process performed by diagnostic engine 104.

Figure 3:
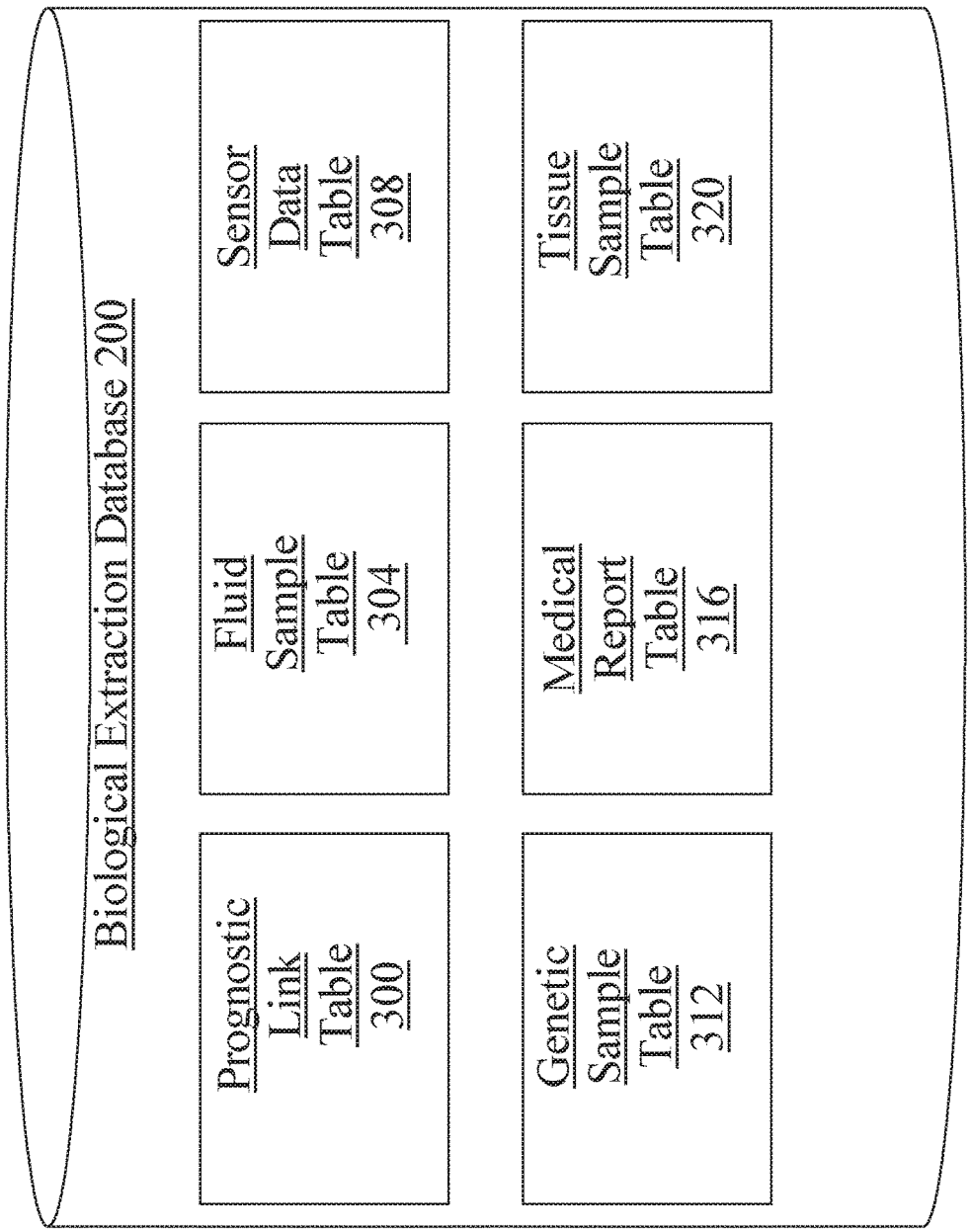
FIG. 3 is a block diagram illustrating an exemplary embodiment of a biological extraction database.

With continued reference to FIG. 3, biological extraction database 200 may include tables listing one or more samples according to sample source. For instance, and without limitation, biological extraction database 200 may include a fluid sample table 304 listing samples acquired from a person by extraction of fluids, such as without limitation blood, lymph cerebrospinal fluid, or the like. As another non-limiting example, biological extraction database 200 may include a sensor data table 308, which may list samples acquired using one or more sensors, for instance as described in further detail below. As a further non-limiting example, biological extraction database 200 may include a genetic sample table 312, which may list partial or entire sequences of genetic material. Genetic material may be extracted and amplified, as a non-limiting example, using polymerase chain reactions (PCR) or the like. As a further example, also non-limiting, biological extraction database 200 may include a medical report table 316, which may list textual descriptions of medical tests, including without limitation radiological tests or tests of strength and/or dexterity or the like. Data in medical report table may be sorted and/or categorized using a language processing module 312, for instance, translating a textual description into a numerical value and a label corresponding to a category of physiological data; this may be performed using any language processing algorithm or algorithms as referred to in this disclosure. As another non-limiting example, biological extraction database 200 may include a tissue sample table 320, which may record physiological samples obtained using tissue samples. Tables presented above are presented for exemplary purposes only; persons skilled in the art will be aware of various ways in which data may be organized in biological extraction database 200 consistently with this disclosure.

Referring again to FIG. 2, diagnostic engine 104 and/or another device in system 100 may populate one or more fields in biological extraction database 200 using expert information, which may be extracted or retrieved from an expert knowledge database 204. An expert knowledge database 204 may include any data structure and/or data store suitable for use as a biological extraction database 200 as described above. Expert knowledge database 204 may include data entries reflecting one or more expert submissions of data such as may have been submitted according to any process described above in reference to FIG. 1, including without limitation by using first graphical user interface 112 and/or second graphical user interface 140. Expert knowledge database may include one or more fields generated by language processing module 114, such as without limitation fields extracted from one or more documents as described above. For instance, and without limitation, one or more categories of physiological data and/or related prognostic labels and/or categories of prognostic labels associated with an element of physiological state data as described above may be stored in generalized from in an expert knowledge database 204 and linked to, entered in, or associated with entries in a biological extraction database 200. Documents may be stored and/or retrieved by diagnostic engine 104 and/or language processing module 114 in and/or from a document database 208; document database 208 may include any data structure and/or data store suitable for use as biological extraction database 200 as described above. Documents in document database 208 may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, date, or the like as consistent with this disclosure.

Figure 4:
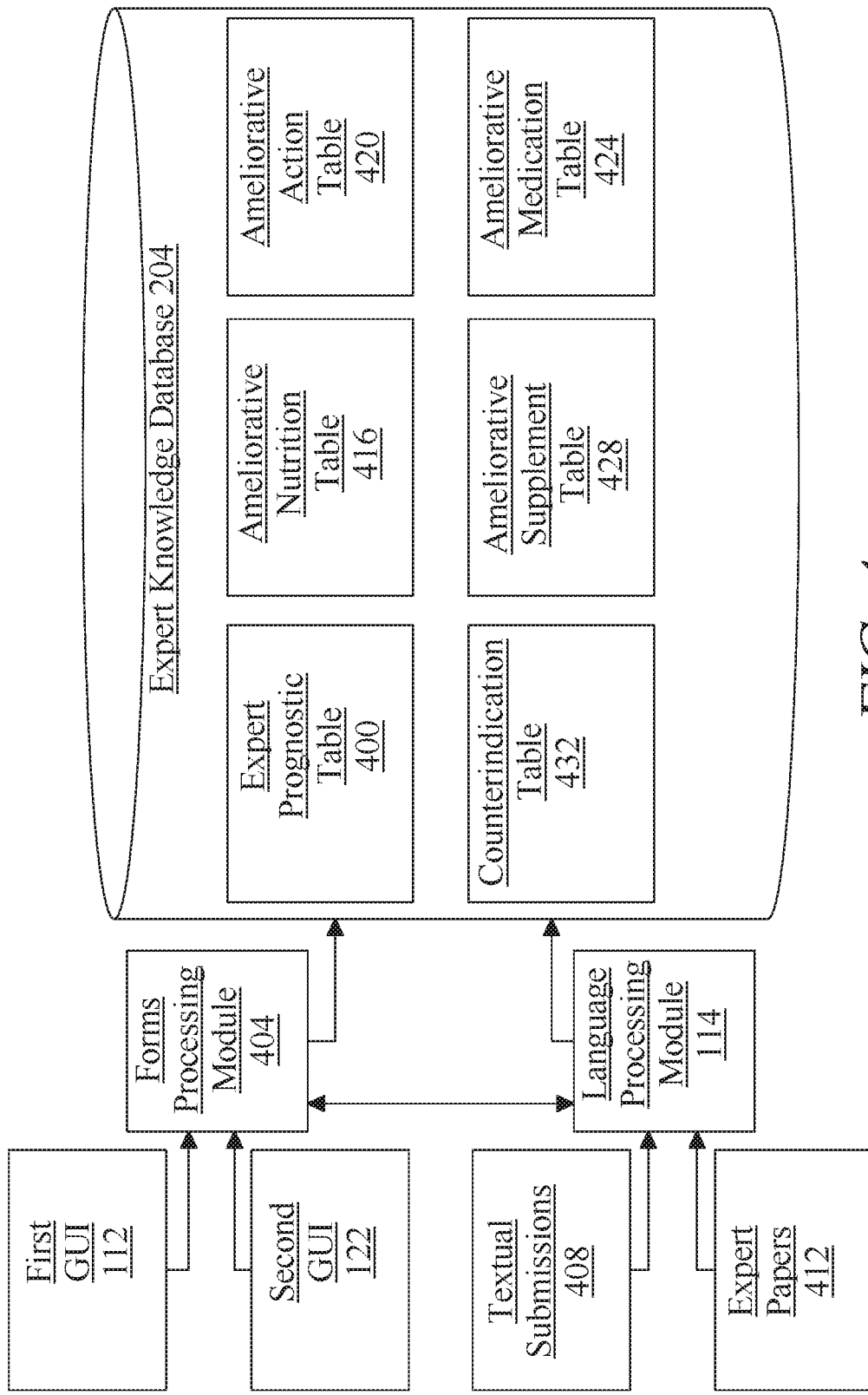
FIG. 4 is a block diagram illustrating an exemplary embodiment of an expert knowledge database.

Referring now to FIG. 4, an exemplary embodiment of an expert knowledge database 204 is illustrated. Expert knowledge database 204 may, as a non-limiting example, organize data stored in the expert knowledge database 204 according to one or more database tables. One or more database tables may be linked to one another by, for instance, common column values. For instance, a common column between two tables of expert knowledge database 200 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 4, one or more database tables in expert knowledge database 204 may include, as a non-limiting example, an expert prognostic table 400. Expert prognostic table 400 may be a table relating physiological sample data as described above to prognostic labels; for instance, where an expert has entered data relating a prognostic label to a category of physiological sample data and/or to an element of physiological sample data via first graphical user interface 120 as described above, one or more rows recording such an entry may be inserted in expert prognostic table 400. In an embodiment, a forms processing module 404 may sort data entered in a submission via first graphical user interface 120 by, for instance, sorting data from entries in the first graphical user interface 120 to related categories of data; for instance, data entered in an entry relating in the first graphical user interface 120 to a prognostic label may be sorted into variables and/or data structures for storage of prognostic labels, while data entered in an entry relating to a category of physiological data and/or an element thereof may be sorted into variables and/or data structures for the storage of, respectively, categories of physiological data or elements of physiological data. Where data is chosen by an expert from pre-selected entries such as drop-down lists, data may be stored directly; where data is entered in textual form, language processing module 114 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 408, such as accomplished by filling out a paper or PDF form and/or submitting narrative information, may likewise be processed using language processing module 114. Data may be extracted from expert papers 412, which may include without limitation publications in medical and/or scientific journals, by language processing module 114 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert prognostic table 400 may include a single table and/or a plurality of tables; plurality of tables may include tables for particular categories of prognostic labels such as a current diagnosis table, a future prognosis table, a genetic tendency table, a metabolic tendency table, and/or an endocrinal tendency table (not shown), to name a few non-limiting examples presented for illustrative purposes only.

With continued reference to FIG. 4, one or more database tables in expert knowledge database 204 may include, as a further non-limiting example tables listing one or more ameliorative process labels; expert data populating such tables may be provided, without limitation, using any process described above, including entry of data from second graphical user interface 140 via forms processing module 404 and/or language processing module 114, processing of textual submissions 408, or processing of expert papers 412. For instance, and without limitation, an ameliorative nutrition table 416 may list one or more ameliorative processes based on nutritional instructions, and/or links of such one or more ameliorative processes to prognostic labels, as provided by experts according to any method of processing and/or entering expert data as described above. As a further example an ameliorative action table 420 may list one or more ameliorative processes based on instructions for actions a user should take, including without limitation exercise, meditation, and/or cessation of harmful eating, substance abuse, or other habits, and/or links of such one or more ameliorative processes to prognostic labels, as provided by experts according to any method of processing and/or entering expert data as described above. As an additional example, an ameliorative supplement table 424 may list one or more ameliorative processes based on nutritional supplements, such as vitamin pills or the like, and/or links of such one or more ameliorative processes to prognostic labels, as provided by experts according to any method of processing and/or entering expert data as described above. As a further non-limiting example, an ameliorative medication table 428 may list one or more ameliorative processes based on medications, including without limitation over-the-counter and prescription pharmaceutical drugs, and/or links of such one or more ameliorative processes to prognostic labels, as provided by experts according to any method of processing and/or entering expert data as described above. As an additional example, a counterindication table 432 may list one or more counter-indications for one or more ameliorative processes; counterindications may include, without limitation allergies to one or more foods, medications, and/or supplements, side-effects of one or more medications and/or supplements, interactions between medications, foods, and/or supplements, exercises that should not be used given one or more medical conditions, injuries, disabilities, and/or demographic categories, or the like. Tables presented above are presented for exemplary purposes only; persons skilled in the art will be aware of various ways in which data may be organized in expert knowledge database 204 consistently with this disclosure.

Referring again to FIG. 2, a prognostic label database 212, which may be implemented in any manner suitable for implementation of biological extraction database 200, may be used to store prognostic labels used in system 100, including any prognostic labels correlated with elements of physiological data in first training set 106 as described above; prognostic labels may be linked to or refer to entries in biological extraction database 200 to which prognostic labels correspond. Linking may be performed by reference to historical data concerning physiological samples, such as diagnoses, prognoses, and/or other medical conclusions derived from physiological samples in the past; alternatively or additionally, a relationship between a prognostic label and a data entry in biological extraction database 200 may be determined by reference to a record in an expert knowledge database 204 linking a given prognostic label to a given category of physiological sample as described above. Entries in prognostic label database 212 may be associated with one or more categories of prognostic labels as described above, for instance using data stored in and/or extracted from an expert knowledge database 204.

Figure 5:
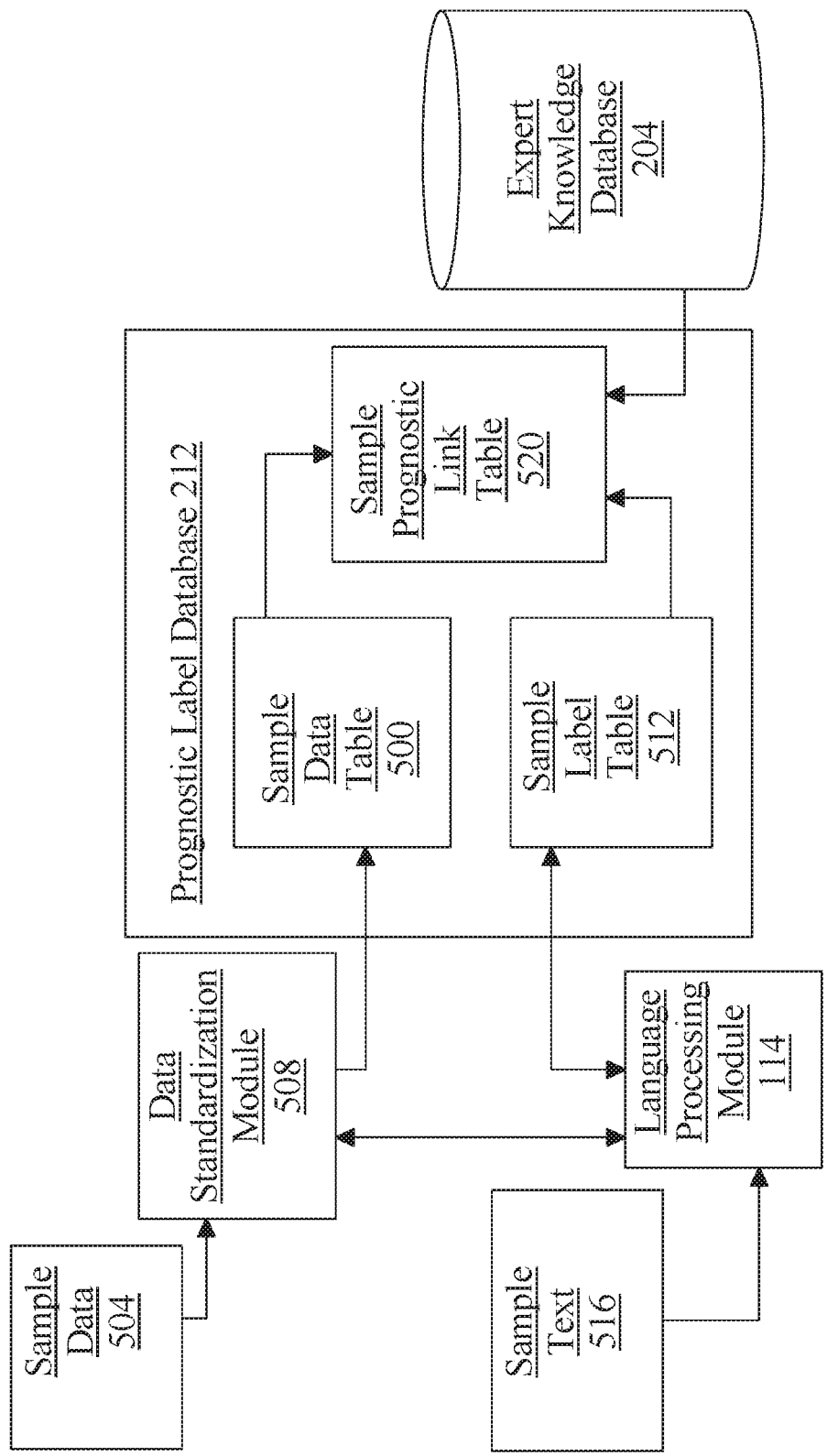
FIG. 5 is a block diagram illustrating an exemplary embodiment of a prognostic label database.

Referring now to FIG. 5, an exemplary embodiment of a prognostic label database 212 is illustrated. Prognostic label database 212 may, as a non-limiting example, organize data stored in the prognostic label database 212 according to one or more database tables. One or more database tables may be linked to one another by, for instance, common column values. For instance, a common column between two tables of prognostic label database 212 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 5, one or more database tables in prognostic label database 212 may include, as a non-limiting example, a sample data table 500. Sample data table 500 may be a table listing sample data, along with, for instance, one or more linking columns to link such data to other information stored in prognostic label database 212. In an embodiment, sample data 504 may be acquired, for instance from biological extraction database 200, in a raw or unsorted form, and may be translated into standard forms, such as standard units of measurement, labels associated with particular physiological data values, or the like; this may be accomplished using a data standardization module 508, which may perform unit conversions. Data standardization module 508 may alternatively or additionally map textual information, such as labels describing values tested for or the like, using language processing module 114 or equivalent components and/or algorithms thereto.

Continuing to refer to FIG. 5, prognostic label database 212 may include a sample label table 512; sample label table 512 may list prognostic labels received with and/or extracted from physiological samples, for instance as received in the form of sample text 516. A language processing module 114 may compare textual information so received to prognostic labels and/or form new prognostic labels according to any suitable process as described above. Sample prognostic link table may combine samples with prognostic labels, as acquired from sample label table and/or expert knowledge database 204; combination may be performed by listing together in rows or by relating indices or common columns of two or more tables to each other. Tables presented above are presented for exemplary purposes only; persons skilled in the art will be aware of various ways in which data may be organized in expert knowledge database 204 consistently with this disclosure.

Referring again to FIG. 2, first training set 106 may be populated by retrieval of one or more records from biological extraction database 200 and/or prognostic label database 212; in an embodiment, entries retrieved from biological extraction database 200 and/or prognostic label database 212 may be filtered and or select via query to match one or more additional elements of information as described above, so as to retrieve a first training set 106 including data belonging to a given cohort, demographic population, or other set, so as to generate outputs as described below that are tailored to a person or persons with regard to whom system 100 classifies physiological samples to prognostic labels as set forth in further detail below. Persons skilled in the art, upon reviewing the entirety of this disclosure, will be aware of various ways in which records may be retrieved from biological extraction database 200 and/or prognostic label database to generate a first training set to reflect individualized group data pertaining to a person of interest in operation of system and/or method, including without limitation a person with regard to whom at least a physiological sample is being evaluated as described in further detail below. Diagnostic engine 104 may alternatively or additionally receive a first training set 106 and store one or more entries in biological extraction database 200 and/or prognostic label database 212 as extracted from elements of first training set 106.

Still referring to FIG. 2, system 100 may include or communicate with an ameliorative process label database 216; an ameliorative process label database 216 may include any data structure and/or datastore suitable for use as a biological extraction database 200 as described above. An ameliorative process label database 216 may include one or more entries listing labels associated with one or more ameliorative processes as described above, including any ameliorative labels correlated with prognostic labels in second training set 116 as described above; ameliorative process labels may be linked to or refer to entries in prognostic label database 212 to which ameliorative process labels correspond. Linking may be performed by reference to historical data concerning prognostic labels, such as therapies, treatments, and/or lifestyle or dietary choices chosen to alleviate conditions associated with prognostic labels in the past; alternatively or additionally, a relationship between an ameliorative process label and a data entry in prognostic label database 212 may be determined by reference to a record in an expert knowledge database 204 linking a given ameliorative process label to a given category of prognostic label as described above. Entries in ameliorative process label database 212 may be associated with one or more categories of prognostic labels as described above, for instance using data stored in and/or extracted from an expert knowledge database 204.

Figure 6:
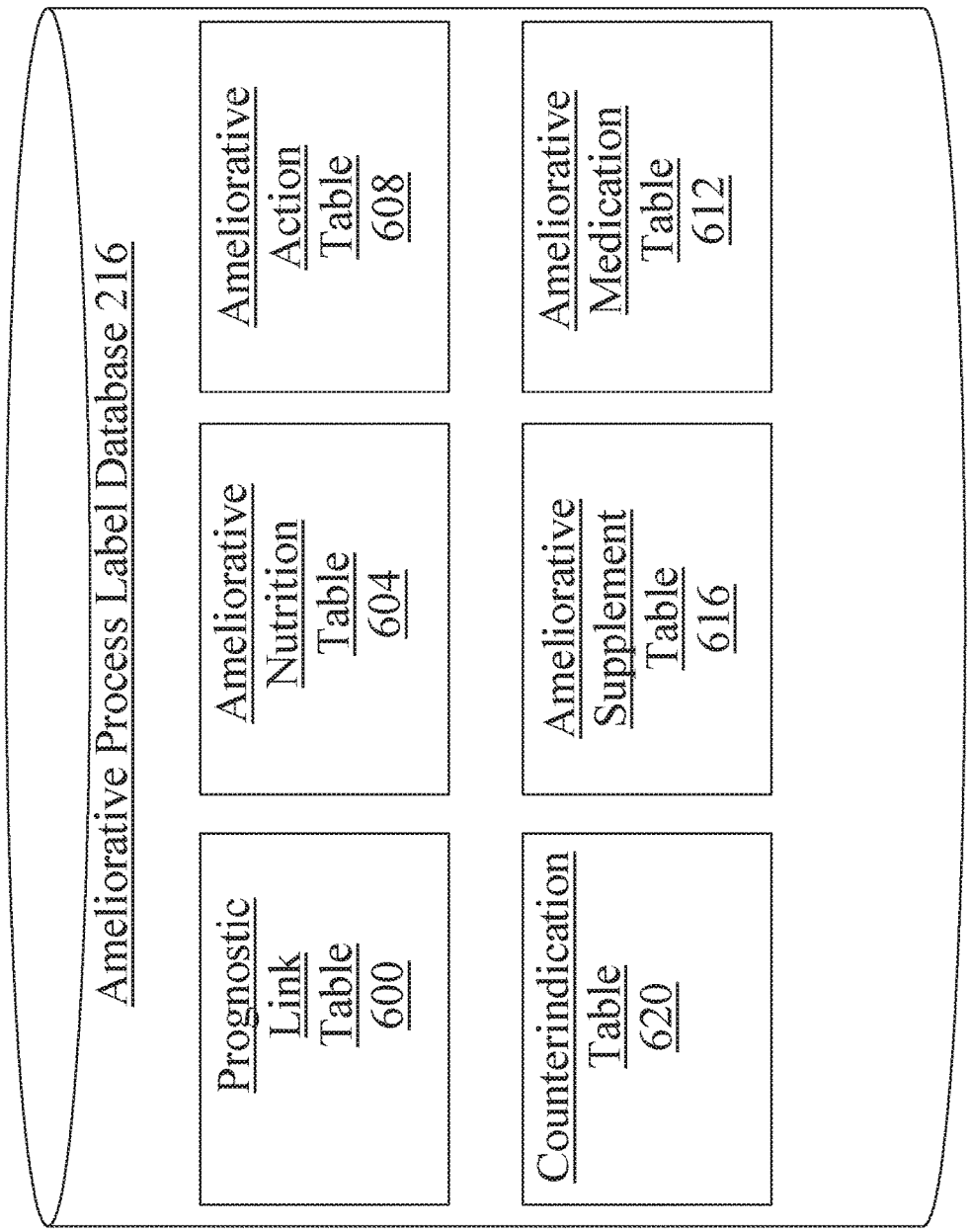
FIG. 6 is a block diagram illustrating an exemplary embodiment of an ameliorative process label database.

Referring now to FIG. 6, an exemplary embodiment of an ameliorative process label database 216 is illustrated. Ameliorative process label database 216 may, as a non-limiting example, organize data stored in the ameliorative process label database 216 according to one or more database tables. One or more database tables may be linked to one another by, for instance, common column values. For instance, a common column between two tables of ameliorative process label database 216 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 6, ameliorative process label database 216 may include a prognostic link table 600; prognostic link table may link ameliorative process data to prognostic label data, using any suitable method for linking data in two or more tables as described above. Ameliorative process label database 216 may include an ameliorative nutrition table 604, which may list one or more ameliorative processes based on nutritional instructions, and/or links of such one or more ameliorative processes to prognostic labels, for instance as provided by experts according to any method of processing and/or entering expert data as described above, and/or using one or more machine-learning processes as set forth in further detail below. As a further example an ameliorative action table 608 may list one or more ameliorative processes based on instructions for actions a user should take, including without limitation exercise, meditation, and/or cessation of harmful eating, substance abuse, or other habits, and/or links of such one or more ameliorative processes to prognostic labels, as provided by experts according to any method of processing and/or entering expert data as described above and/or using one or more machine-learning processes as set forth in further detail below. As an additional example, an ameliorative supplement table 612 may list one or more ameliorative processes based on nutritional supplements, such as vitamin pills or the like, and/or links of such one or more ameliorative processes to prognostic labels, as provided by experts according to any method of processing and/or entering expert data as described above and/or using one or more machine-learning processes as set forth in further detail below. As a further non-limiting example, an ameliorative medication table 616 may list one or more ameliorative processes based on medications, including without limitation over-the-counter and prescription pharmaceutical drugs, and/or links of such one or more ameliorative processes to prognostic labels, as provided by experts according to any method of processing and/or entering expert data as described above and/or using one or more machine-learning processes as set forth in further detail below. As an additional example, a counter-indication table 620 may list one or more counter-indications for one or more ameliorative processes; counterindications may include, without limitation allergies to one or more foods, medications, and/or supplements, side-effects of one or more medications and/or supplements, interactions between medications, foods, and/or supplements, exercises that should not be used given one or more medical conditions, injuries, disabilities, and/or demographic categories, or the like; this may be acquired using expert submission as described above and/or using one or more machine-learning processes as set forth in further detail below. Tables presented above are presented for exemplary purposes only; persons skilled in the art will be aware of various ways in which data may be organized in ameliorative process database 216 consistently with this disclosure Referring again to FIG. 2, second training set 116 may be populated by retrieval of one or more records from prognostic label database 212 and/or ameliorative process label database 216; in an embodiment, entries retrieved from prognostic label database 212 and/or ameliorative process label database 216 may be filtered and or select via query to match one or more additional elements of information as described above, so as to retrieve a second training set 116 including data belonging to a given cohort, demographic population, or other set, so as to generate outputs as described below that are tailored to a person or persons with regard to whom system 100 classifies prognostic labels to ameliorative process labels as set forth in further detail below. Persons skilled in the art, upon reviewing the entirety of this disclosure, will be aware of various ways in which records may be retrieved from prognostic label database 212 and/or ameliorative process label database 216 to generate a second training set 116 to reflect individualized group data pertaining to a person of interest in operation of system and/or method, including without limitation a person with regard to whom at least a physiological sample is being evaluated as described in further detail below. Diagnostic engine 104 may alternatively or additionally receive a second training set 116 and store one or more entries in prognostic label database 212 and/or ameliorative process label database 216 as extracted from elements of second training set 116.

With continued reference to FIG. 2, diagnostic engine 104 may receive an update to one or more elements of data represented in first training set 106 and/or second training set 116, and may perform one or more modifications to first training set 106 and/or second training set 116, or to biological extraction database 200, expert knowledge database 204, prognostic label database 212, and/or ameliorative process label database 216 as a result. For instance, a physiological sample may turn out to have been erroneously recorded; diagnostic engine 104 may remove it from first training set 106, second training set 116, biological extraction database 200, expert knowledge database 204, prognostic label database 212, and/or ameliorative process label database 216 as a result. As a further example, a medical and/or academic paper, or a study on which it was based, may be revoked; diagnostic engine 104 may remove it from first training set 106, second training set 116, biological extraction database 200, expert knowledge database 204, prognostic label database 212, and/or ameliorative process label database 216 as a result. Information provided by an expert may likewise be removed if the expert loses credentials or is revealed to have acted fraudulently.

Continuing to refer to FIG. 2, elements of data first training set 106, second training set 116, biological extraction database 200, expert knowledge database 204, prognostic label database 212, and/or ameliorative process label database 216 may have temporal attributes, such as timestamps; diagnostic engine 104 may order such elements according to recency, select only elements more recently entered for first training set 106 and/or second training set 116, or otherwise bias training sets, database entries, and/or machine-learning models as described in further detail below toward more recent or less recent entries. Persons skilled in the art, upon reviewing the entirety of this disclosure, will be aware of various ways in which temporal attributes of data entries may be used to affect results of methods and/or systems as described herein.

Figure 7:
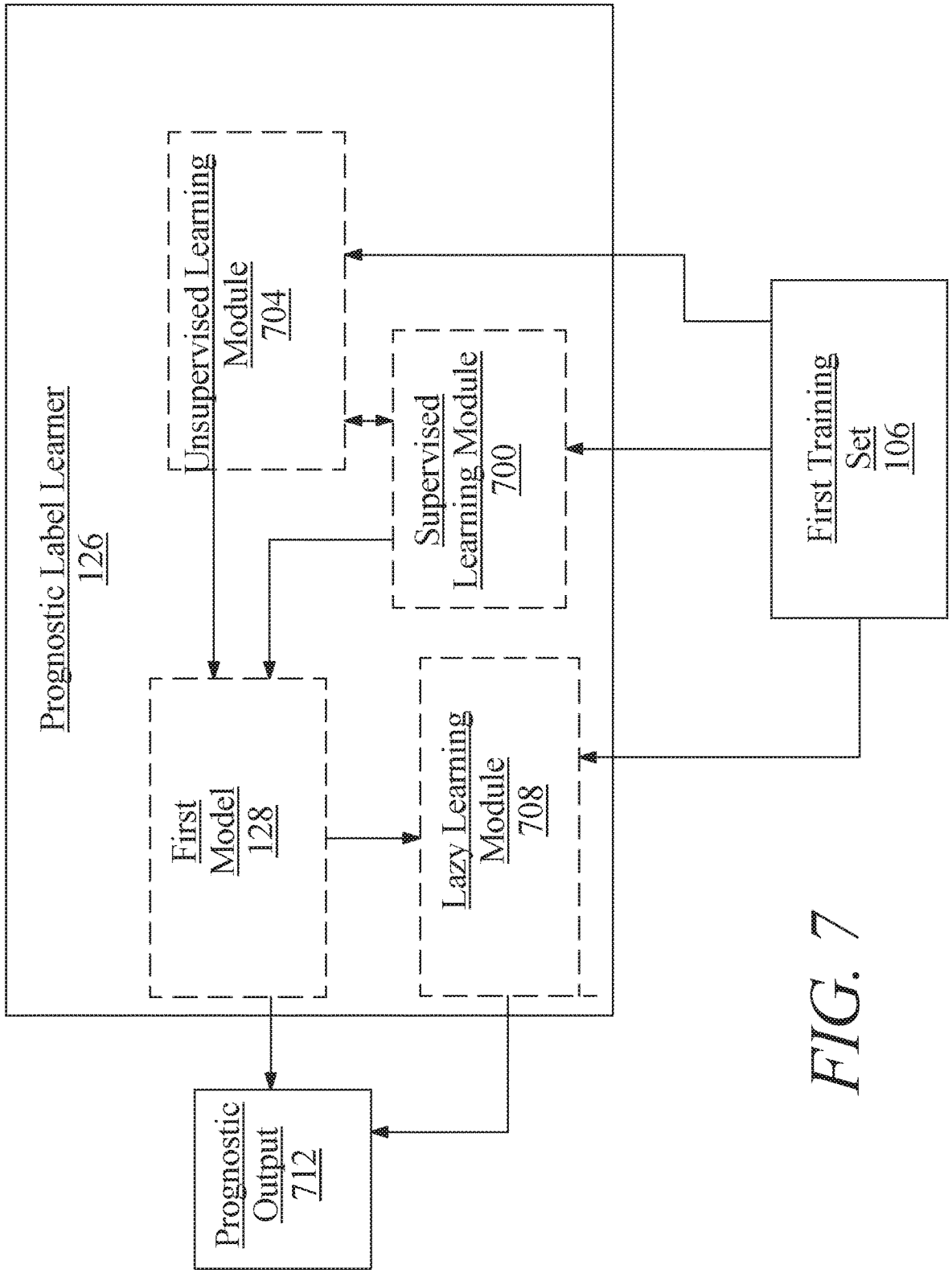
FIG. 7 is a block diagram illustrating an exemplary embodiment of a prognostic label learner and associated system elements.

Referring now to FIG. 7, machine-learning algorithms used by prognostic label learner 126 may include supervised machine-learning algorithms, which may, as a non-limiting example be executed using a supervised learning module 700 executing on diagnostic engine 104 and/or on another computing device in communication with diagnostic engine 104, which may include any hardware or software module. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of physiological data as inputs, prognostic labels as outputs, and a scoring function representing a desired form of relationship to be detected between elements of physiological data and prognostic labels; scoring function may, for instance, seek to maximize the probability that a given element of physiological state data 108 and/or combination of elements of physiological data is associated with a given prognostic label and/or combination of prognostic labels to minimize the probability that a given element of physiological state data 108 and/or combination of elements of physiological state data 108 is not associated with a given prognostic label and/or combination of prognostic labels. Scoring function may be expressed as a risk function representing an "expected loss" of an algorithm relating inputs to outputs, where loss is computed as an error function representing a degree to which a prediction generated by the relation is incorrect when compared to a given input-output pair provided in first training set 106. Persons skilled in the art, upon reviewing the entirety of this disclosure, will be aware of various possible variations of supervised machine learning algorithms that may be used to determine relation between elements of physiological data and prognostic labels. In an embodiment, one or more supervised machine-learning algorithms may be restricted to a particular domain for instance, a supervised machine-learning process may be performed with respect to a given set of parameters and/or categories of parameters that have been suspected to be related to a given set of prognostic labels, and/or are specified as linked to a medical specialty and/or field of medicine covering a particular set of prognostic labels. As a non-limiting example, a particular set of blood test biomarkers and/or sensor data may be typically used by cardiologists to diagnose or predict various cardiovascular conditions, and a supervised machine-learning process may be performed to relate those blood test biomarkers and/or sensor data to the various cardiovascular conditions; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate prognostic labels. Additional supervised learning processes may be performed without domain restrictions to detect, for instance, previously unknown and/or unsuspected relationships between physiological data and prognostic labels.

Figure 8:
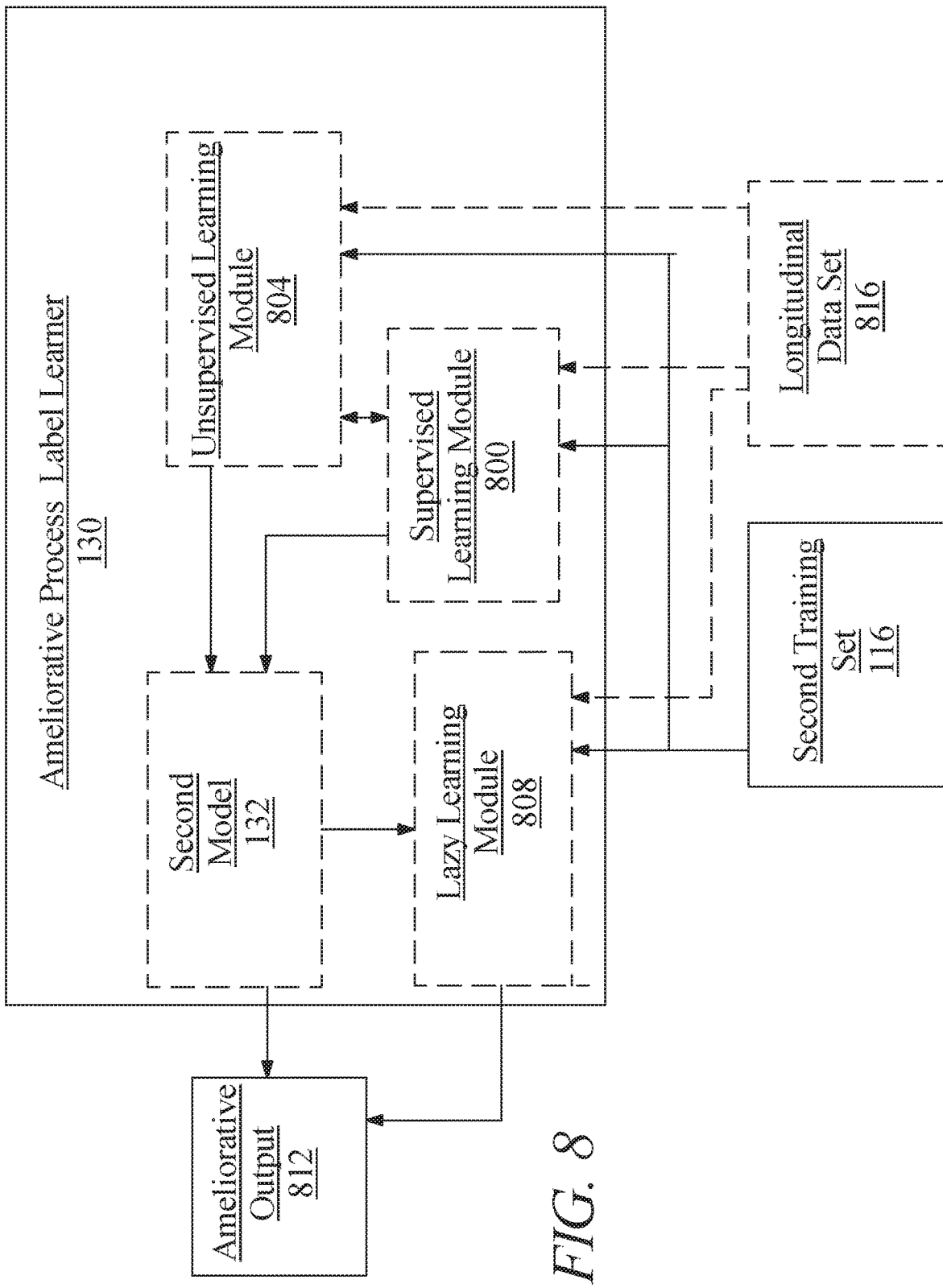
FIG. 8 is a block diagram illustrating an exemplary embodiment of an ameliorative process label learner and associated system elements.

Referring now to FIG. 8, ameliorative process label learner 130 may be configured to perform one or more supervised learning processes, as described above; supervised learning processes may be performed by a supervised learning module 800 executing on diagnostic engine 104 and/or on another computing device in communication with diagnostic engine 104, which may include any hardware or software module. For instance, a supervised learning algorithm may use prognostic labels as inputs, ameliorative labels as outputs, and a scoring function representing a desired form of relationship to be detected between prognostic labels and ameliorative labels; scoring function may, for instance, seek to maximize the probability that a given prognostic label and/or combination of prognostic labels is associated with a given ameliorative label and/or combination of ameliorative labels to minimize the probability that a given prognostic label and/or combination of prognostic labels is not associated with a given ameliorative label and/or combination of ameliorative labels. In an embodiment, one or more supervised machine-learning algorithms may be restricted to a particular domain; for instance, a supervised machine-learning process may be performed with respect to a given set of parameters and/or categories of prognostic labels that have been suspected to be related to a given set of ameliorative labels, for instance because the ameliorative processes corresponding to the set of ameliorative labels are hypothesized or suspected to have an ameliorative effect on conditions represented by the prognostic labels, and/or are specified as linked to a medical specialty and/or field of medicine covering a particular set of prognostic labels and/or ameliorative labels. As a non-limiting example, a particular set prognostic labels corresponding to a set of cardiovascular conditions may be typically treated by cardiologists, and a supervised machine-learning process may be performed to relate those prognostic labels to ameliorative labels associated with various treatment options, medications, and/or lifestyle changes.

With continued reference to FIG. 8, ameliorative process label learner 130 may perform one or more unsupervised machine-learning processes as described above; unsupervised processes may be performed by an unsupervised learning module 804 executing on diagnostic engine 104 and/or on another computing device in communication with diagnostic engine 104, which may include any hardware or software module. For instance, and without limitation, ameliorative process label learner 130 and/or diagnostic engine 104 may perform an unsupervised machine learning process on second training set 116, which may cluster data of second training set 116 according to detected relationships between elements of the second training set 116, including without limitation correlations of prognostic labels to each other and correlations of ameliorative labels to each other; such relations may then be combined with supervised machine learning results to add new criteria for ameliorative process label learner 130 to apply in relating prognostic labels to ameliorative labels. As a non-limiting, illustrative example, an unsupervised process may determine that a first prognostic label 110 correlates closely with a second prognostic label 118, where the first prognostic label 110 has been linked via supervised learning processes to a given ameliorative label, but the second has not; for instance, the second prognostic label 118 may not have been defined as an input for the supervised learning process, or may pertain to a domain outside of a domain limitation for the supervised learning process. Continuing the example, a close correlation between first prognostic label 110 and second prognostic label 118 may indicate that the second prognostic label 118 is also a good match for the ameliorative label; second prognostic label 118 may be included in a new supervised process to derive a relationship or may be used as a synonym or proxy for the first prognostic label 110 by ameliorative process label learner 130. Unsupervised processes performed by ameliorative process label learner 130 may be subjected to any domain limitations suitable for unsupervised processes performed by prognostic label learner 126 as described above.

Still referring to FIG. 8, diagnostic engine 104 and/or ameliorative process label learner 130 may detect further significant categories of prognostic labels, relationships of such categories to ameliorative labels, and/or categories of ameliorative labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to system 100, ameliorative process label learner 130 and/or diagnostic engine 104 may continuously or iteratively perform unsupervised machine-learning processes to detect relationships between different elements of the added and/or overall data; in an embodiment, this may enable system 100 to use detected relationships to discover new correlations between known biomarkers, prognostic labels, and/or ameliorative labels and one or more elements of data in large bodies of data, such as genomic, proteomic, and/or microbiome-related data, enabling future supervised learning and/or lazy learning processes to identify relationships between, e.g., particular clusters of genetic alleles and particular prognostic labels and/or suitable ameliorative labels. Use of unsupervised learning may greatly enhance the accuracy and detail with which system may detect prognostic labels and/or ameliorative labels.

With continued reference to FIG. 8, ameliorative labels may be generated based on classification of the at least a prognostic output. Classification as used herein includes pairing or grouping prognostic outputs as a function of some shared commonality. Prognostic outputs may be grouped with certain endocrine disorders such as diabetes, metabolic syndrome, and/or pre-diabetes which may generate an ameliorative label associated with a physical exercise recommendation that may include aerobic exercises such as running, brisk walking, cycling, and/or swimming in an attempt to reduce elevated blood sugar levels in patients with such endocrine disorders. Prognostic outputs grouped with certain alarm conditions such as chest pains, shortness of breath, cold sweat, and sudden dizziness may generate an ameliorative label associated with medical tests, diagnostics, and/or procedures for a suspected myocardial infarction such as an electrocardiogram (EKG), measurement of serum troponin levels, complete blood count (CBC), chest x-ray, echocardiogram, cardiac CT, cardiac MRI, and/or coronary catheterization. Ameliorative label may be generated based on groupings such as severity of prognostic output. For example, a user who presents with mild chest pain and some indigestion may be grouped to a category of prognostic labels that is serious but not alarming and may generate an ameliorative label that includes a blood test for troponin levels to rule out a potential myocardial infarction. A user who presents with crushing chest pain, tingling down one or both arms, shortness of breath, and cold and clammy skin may be grouped into a category of alarm so as to generate an ameliorative label that includes a cardiac CT or cardiac MRI to see if user is suffering from some type of coronary occlusion and may be a candidate for a possible coronary catheterization. In yet another non-limiting example, ameliorative label may be generated as a function of severity and/or progression of prognostic output. For example, a prognostic label that includes a diagnosis of hypothyroidism as evidenced by a thyroid stimulating level (TSH) of 6.0 (normal range is 1.4-5.5) may generate an ameliorative label that includes 150 mcg per day of iodine supplementation to lower TSH within normal limits due to mild TSH elevation and/or mild progression of hypothyroidism. A prognostic output that includes a diagnosis of hypothyroidism as evidenced by a TSH of 15.0 may generate an ameliorative label that includes 300 mcg per day of iodine supplementation as well as a prescription for a T-4 containing medication such as Synthroid and a T-3 containing medication such as Cytomel due to the more severe progression of hypothyroidism. Classification of at least a prognostic output may include staging of a prognostic label. Staging may include dividing a disease state or condition into categories on a spectrum of disease progression and symptomology. For example, a user with a prognostic output that indicates peri-menopause as evidenced by increasing prevalence of hot flashes may generate an ameliorative label that includes a recommendation for supplementation with black cohosh, while a user with a prognostic output that indicates progression to menopause as evidenced by persistent hot flashes, night sweats, absence of menstruation, dry hair, and fatigue may generate an ameliorative label that contains recommendations for supplementation with bio-identical hormone replacement therapy such as estrone (E1), estradiol (E2), estriol (E3), progesterone, testosterone, dehydroepiandrosterone (DHEA), and/or pregnenolone. In yet another non-limiting example, early stage of a disease such as Alzheimer's disease as demonstrated by mild cognitive impairment may generate an ameliorative label that includes no recommended medical treatment except for watchful waiting. However, advanced Alzheimer's disease may warrant an ameliorative label that includes medical intervention and may require a prescription medication. Ameliorative label may be generated by any of the methodologies as described below in reference to FIG. 19.

Continuing to view FIG. 8, ameliorative process label learner 130 may be configured to perform a lazy learning process as a function of the second training set 116 and the at least a prognostic output to produce the at least an ameliorative output; a lazy learning process may include any lazy learning process as described above regarding prognostic label learner 126. Lazy learning processes may be performed by a lazy learning module 808 executing on diagnostic engine 104 and/or on another computing device in communication with diagnostic engine 104, which may include any hardware or software module. Ameliorative output 812 may be provided to a user output device as described in further detail below.

In an embodiment, and still referring to FIG. 8, ameliorative process label learner 130 may generate a plurality of ameliorative labels having different implications for a particular person. For instance, where a prognostic label indicates that a person has a magnesium deficiency, various dietary choices may be generated as ameliorative labels associated with correcting the deficiency, such as ameliorative labels associated with consumption of almonds, spinach, and/or dark chocolate, as well as ameliorative labels associated with consumption of magnesium supplements. In such a situation, ameliorative process label learner 130 and/or diagnostic engine 104 may perform additional processes to resolve ambiguity. Processes may include presenting multiple possible results to a medical practitioner, informing the medical practitioner of various options that may be available, and/or that follow-up tests, procedures, or counseling may be required to select an appropriate choice. Alternatively or additionally, processes may include additional machine learning steps. For instance, ameliorative process label learner 130 may perform one or more lazy learning processes using a more comprehensive set of user data to identify a more probably correct result of the multiple results. Results may be presented and/or retained with rankings, for instance to advise a medical professional of the relative probabilities of various ameliorative labels being correct or ideal choices for a given person; alternatively or additionally, ameliorative labels associated with a probability of success or suitability below a given threshold and/or ameliorative labels contradicting results of the additional process, may be eliminated. As a non-limiting example, an additional process may reveal that a person is allergic to tree nuts, and consumption of almonds may be eliminated as an ameliorative label to be presented.

Continuing to refer to FIG. 8, ameliorative process label learner 130 may be designed and configured to generate further training data and/or to generate outputs using longitudinal data 816. As used herein, longitudinal data 816 may include a temporally ordered series of data concerning the same person, or the same cohort of persons; for instance, longitudinal data 816 may describe a series of blood samples taken one day or one month apart over the course of a year. Longitudinal data 816 may related to a series of samples tracking response of one or more elements of physiological data recorded regarding a person undergoing one or more ameliorative processes linked to one or more ameliorative process labels. Ameliorative process label learner 130 may track one or more elements of physiological data and fit, for instance, a linear, polynomial, and/or splined function to data points; linear, polynomial, or other regression across larger sets of longitudinal data, using, for instance, any regression process as described above, may be used to determine a best-fit graph or function for the effect of a given ameliorative process over time on a physiological parameter. Functions may be compared to each other to rank ameliorative processes; for instance, an ameliorative process associated with a steeper slope in curve representing improvement in a physiological data element, and/or a shallower slope in a curve representing a slower decline, may be ranked higher than an ameliorative process associated with a less steep slope for an improvement curve or a steeper slope for a curve marking a decline. Ameliorative processes associated with a curve and/or terminal data point representing a value that does not associate with a previously detected prognostic label may be ranked higher than one that is not so associated. Information obtained by analysis of longitudinal data 816 may be added to ameliorative process database and/or second training set.

Figure 9:
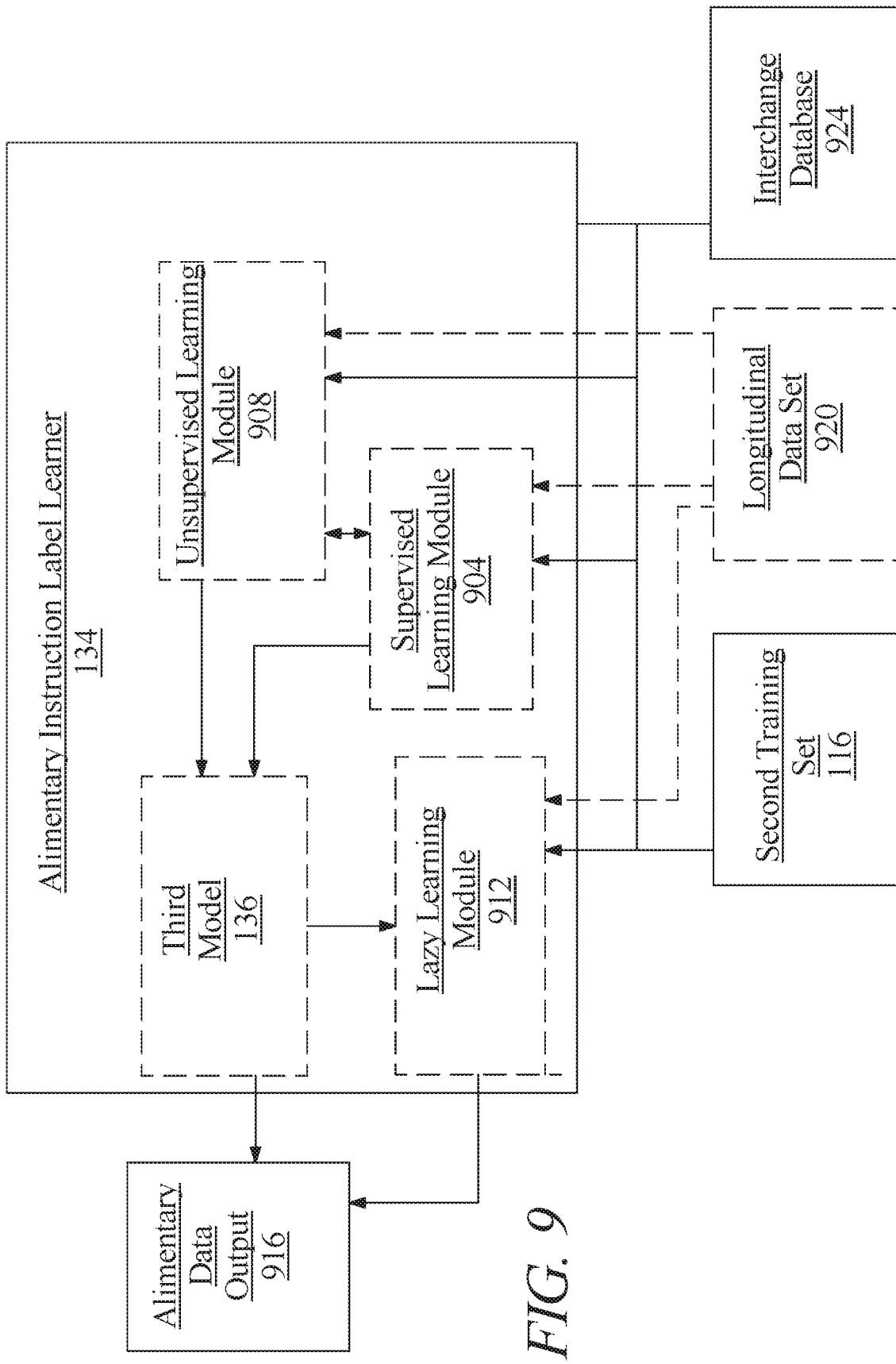
FIG. 9 is a block diagram illustrating an exemplary embodiment of an alimentary instruction label learner and associated system elements.

Referring now to FIG. 9, an exemplary embodiment of alimentary instruction label learner 134 is illustrated. alimentary instruction label learner 134 may be configured to perform one or more supervised learning processes, as described above; supervised learning processes may be performed by a supervised learning module 904 executing on diagnostic engine 104 and/or on another computing device in communication with diagnostic engine 104, which may include any hardware or software module. For instance, a supervised learning algorithm may use prognostic labels as inputs, alimentary labels as outputs, and a scoring function representing a desired form of relationship to be detected between prognostic labels and alimentary labels; scoring function may, for instance, seek to maximize the probability that a given prognostic label and/or combination of prognostic labels is associated with a given alimentary label and/or combination of alimentary labels to minimize the probability that a given prognostic label and/or combination of prognostic labels is not associated with a given alimentary label and/or combination of alimentary labels. In an embodiment, one or more supervised machine-learning algorithms may be restricted to a particular domain; for instance, a supervised machine-learning process may be performed with respect to a given set of parameters and/or categories of prognostic labels that have been suspected to be related to a given set of alimentary labels, for instance because the alimentary processes corresponding to the set of alimentary labels are hypothesized or suspected to have an ameliorative effect on conditions represented by the prognostic labels, and/or are specified as linked to a medical specialty and/or field of medicine covering a particular set of prognostic labels and/or alimentary labels. As a non-limiting example, a particular set prognostic labels corresponding to a set of cardiovascular conditions may be typically treated by cardiologists, and a supervised machine-learning process may be performed to relate those prognostic labels to alimentary labels associated with various alimentary options.

With continued reference to FIG. 9, alimentary instruction label learner 134 may perform one or more unsupervised machine-learning processes as described above; unsupervised processes may be performed by an unsupervised learning module 908 executing on diagnostic engine 104 and/or on another computing device in communication with diagnostic engine 104, which may include any hardware or software module. For instance, and without limitation, alimentary instruction label learner 134 and/or diagnostic engine 104 may perform an unsupervised machine learning process on second training set 116, which may cluster data of second training set 116 according to detected relationships between elements of the second training set 116, including without limitation correlations of prognostic labels to each other and correlations of alimentary labels to each other; such relations may then be combined with supervised machine learning results to add new criteria for alimentary instruction label learner 134 to apply in relating prognostic labels to alimentary labels. As a non-limiting, illustrative example, an unsupervised process may determine that a first prognostic label 110 correlates closely with a second prognostic label 118, where the first prognostic label 110 has been linked via supervised learning processes to a given alimentary label, but the second has not; for instance, the second prognostic label 118 may not have been defined as an input for the supervised learning process, or may pertain to a domain outside of a domain limitation for the supervised learning process. Continuing the example, a close correlation between first prognostic label 110 and second prognostic label 118 may indicate that the second prognostic label 118 is also a good match for the alimentary label; second prognostic label 118 may be included in a new supervised process to derive a relationship or may be used as a synonym or proxy for the first prognostic label 110 by alimentary instruction label learner 134. Unsupervised processes performed by alimentary instruction label learner 134 may be subjected to any domain limitations suitable for unsupervised processes performed by prognostic label learner 126 as described above.

With continued reference to FIG. 9, alimentary instruction label learner 134 may perform an unsupervised machine learning process on second training set 116, which may cluster data of second training set 116 according to detected relationships between elements of the second training set 116, including for example relationships between foods and/or supplements contained within alimentary instruction sets and diagnostic outputs and/or comprehensive instruction sets; such information may then be combined with supervised machine learning results to add new criteria for alimentary instruction label learner 134 to apply in relating alimentary instruction sets to diagnostic outputs and/or comprehensive instruction sets.

Still referring to FIG. 9, diagnostic engine 104 and/or alimentary instruction label learner 134 may detect further significant categories of prognostic labels, relationships of such categories to alimentary labels, and/or categories of alimentary labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to diagnostic engine 104, alimentary instruction label learner 134 and/or diagnostic engine 104 may continuously or iteratively perform unsupervised machine-learning processes to detect relationships between different elements of the added and/or overall data; in an embodiment, this may enable diagnostic engine 104 to use detected relationships to discover new correlations between known biomarkers, prognostic labels, and/or alimentary labels and one or more elements of data in large bodies of data, such as genomic, proteomic, and/or microbiome-related data, enabling future supervised learning and/or lazy learning processes to identify relationships between, e.g., particular clusters of genetic alleles and particular prognostic labels and/or suitable alimentary labels. Use of unsupervised learning may greatly enhance the accuracy and detail with which system may detect prognostic labels and/or alimentary labels.

Continuing to view FIG. 9, alimentary instruction label learner 134 may be configured to perform a lazy learning process as a function of the second training set 116 and the at least a prognostic output to produce the at least an alimentary output; a lazy learning process may include any lazy learning process as described above regarding prognostic label learner 126. Lazy learning processes may be performed by a lazy learning module 912 executing on diagnostic engine 104 and/or on another computing device in communication with diagnostic engine 104, which may include any hardware or software module. Alimentary output 916 may be provided to a user output device as described in further detail below. Alimentary output 916 may be utilized by plan generator module to generate alimentary instruction set 144.

With continued reference to FIG. 9, alimentary instruction label learner 134 may generate a plurality of alimentary labels having different implications for a particular person. For instance, where a prognostic label indicates that a person has a magnesium deficiency, various dietary choices may be generated as alimentary labels associated with correcting the deficiency, such as alimentary labels associated with consumption of almonds, spinach, and/or dark chocolate, as well as alimentary labels associated with consumption of magnesium supplements. In such a situation, alimentary instruction label learner 134 and/or diagnostic engine 104 may perform additional processes to resolve ambiguity. Processes may include presenting multiple possible results to a medical practitioner, informing the medical practitioner of various options that may be available, and/or that follow-up tests, procedures, or counseling may be required to select an appropriate choice. Alternatively or additionally, processes may include additional machine learning steps. For instance, alimentary instruction label learner 134 may perform one or more lazy learning processes using a more comprehensive set of user data to identify a more probably correct result of the multiple results. Results may be presented and/or retained with rankings, for instance to advise a medical professional of the relative probabilities of various alimentary labels being correct or ideal choices for a given person; alternatively or additionally, alimentary labels associated with a probability of success or suitability below a given threshold and/or alimentary labels contradicting results of the additional process, may be eliminated. As a non-limiting example, an additional process may reveal that a person is allergic to tree nuts, and consumption of almonds may be eliminated as an alimentary label to be presented.

With continued reference to FIG. 9, alimentary instruction label learner 134 may be configured to perform a lazy learning process as a function of first training set 106, and/or second training set 116 to examine relationships between biological extractions, diagnostic outputs and/or alimentary instruction sets. Lazy learning process may include any lazy learning process as described above regarding prognostic label learner 126. Lazy learning processes may be performed by a lazy learning module 912 operating on the at least a server 102 and/or on another computing device in communication with the at least a server 102, which may include any hardware or software module.

With continued reference to FIG. 9, alimentary instruction label learner 134 may generate supervised, unsupervised, and/or lazy learning process algorithms using data collected from users and/or experts. Alimentary instruction label leaner 134 may utilize user data inputs, which may include any of the user data as described above in reference to FIG. 1 such as alimentary quality standard 150 and/or alimentary allocation standard 152. This may include information describing for example dosage form preference, dosage frequency preference, and/or total price for a certain period of time that a user is willing to spend on nutrition and/or supplements. Alimentary instruction label learner 134 may utilize expert knowledge database 204, which may include any of the expert knowledge as described above in reference to FIG. 2. In an embodiment, alimentary instruction label learner 134 may utilize information obtained based on previous interactions with a user. In an embodiment, alimentary instruction label learner 134 may include a feedback mechanism, whereby new user data and/or new expert knowledge is utilized to update algorithms.

Continuing to refer to FIG. 9, alimentary instruction label learner 134 may be designed and configured to generate further training data and/or to generate outputs using longitudinal data 920. As used herein, longitudinal data 920 may include a temporally ordered series of data concerning the same person, or the same cohort of persons; for instance, longitudinal data 920 may describe a series of blood samples taken one day or one month apart over the course of a year. Longitudinal data 920 may relate to a series of samples tracking response of one or more elements of physiological data recorded regarding a person undergoing one or more alimentary processes linked to one or more alimentary process labels. Alimentary instruction label learner 134 may track one or more elements of physiological data and fit, for instance, a linear, polynomial, and/or splined function to data points; linear, polynomial, or other regression across larger sets of longitudinal data, using, for instance, any regression process as described above, may be used to determine a best-fit graph or function for the effect of a given alimentary process over time on a physiological parameter. Functions may be compared to each other to rank alimentary processes; for instance, an alimentary process associated with a steeper slope in curve representing improvement in a physiological data element, and/or a shallower slope in a curve representing a slower decline, may be ranked higher than an alimentary process associated with a less steep slope for an improvement curve or a steeper slope for a curve marking a decline. Alimentary processes associated with a curve and/or terminal data point representing a value that does not associate with a previously detected prognostic label may be ranked higher than one that is not so associated. Information obtained by analysis of longitudinal data 920 may be added to alimentary process database and/or second training set.

With continued reference to FIG. 9, embodiments of diagnostic engine 104 may furnish augmented intelligence systems that facilitate diagnostic, prognostic, curative, and/or therapeutic decisions by nutrition, diet, and wellness professionals such as nutritionists, dieticians, or applicable trainers/coaches/mentors. Diagnostic engine 104 may provide fully automated tools and resources for each applicable professional to handle, process, diagnosis, develop alimentary, diet, or wellness plans, facilitate and monitor all patient implementation, and record each patient status. Provision of expert system elements via expert inputs and document-driven language analysis may ensure that recommendations generated by diagnostic engine 104 are backed by the very best medical and alimentary knowledge and practices in the world. Models and/or learners with access to data in depth may enable generation of recommendations that are directly personalized for each patient, providing complete confidence, mitigated risk, and complete transparency. Access to well-organized and personalized knowledge in depth may greatly enhance efficiency of nutrition consultations; in embodiments, a comprehensive session may be completed in as little as 10 minutes. Recommendations may further suggest follow up testing, therapy, and/or delivery of substances, ensuring an effective ongoing treatment and prognostic plan.

With continued reference to FIG. 9, alimentary instruction label learner 134 may consult interchange database 924 when selecting and/or substituting ingredients contained within alimentary instruction set 144 such as substituting a supplement for a food or a food for a supplement, or substituting a different food or different supplement based on user input. For example, alimentary instruction label learner 134 may consult interchange database 924 when a user can no longer swallow a pill by mouth and would prefer to consume a food based form of the nutrient found within the pill instead. In such an instance, alimentary instruction label learner 134 may consult interchange database 924 so as to select a food form that may optimize a user's nutritional state and still continue to provide adequate nutrition as a function of diagnostic output, biological extraction, and/or comprehensive instruction set. In an embodiment, alimentary instruction label learner 134 may consult variables database as described below in more detail in reference to FIG. 19.

Figure 10:
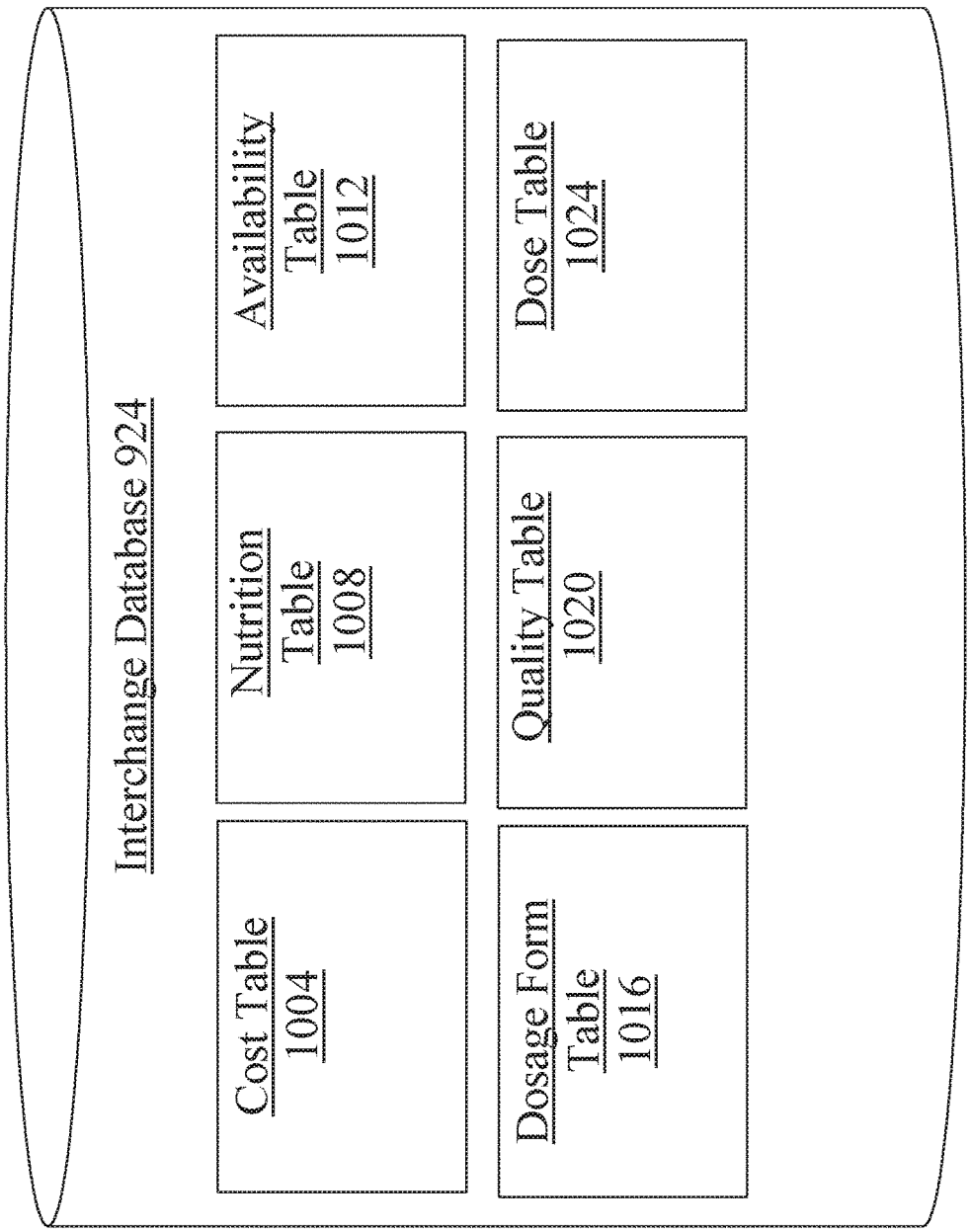
FIG. 10 is a block diagram illustrating an exemplary embodiment of an interchange database.

Referring now to FIG. 10, an exemplary embodiment of interchange database 924 is illustrated. Interchange database 924 may be implemented as any database and/or datastore suitable for use as described above. Interchange database 924 may contain information that may be utilized to generate recommendations for foods and/or supplements contained within alimentary instruction set 144 including information about interchanging foods with supplements and/or supplements with food. One or more database tables contained within interchange database 924 is cost table 1004; cost table 1004 may include any and all information pertaining to how substitution of a particular food and/or supplement within alimentary instruction set may affect cost and impact alimentary allocation standard 152. Cost table 1004 may include cost of a food and/or supplement and information pertaining to how substitution of supplements and/or foods may affect alimentary allocation standard 152. For example, cost table 1004 may be consulted such as when a user has been consuming a resveratrol supplement and user would prefer to consume one glass of red wine each day in lieu of swallowing a pill. In such an instance, cost table 1004 may be consulted to determine the cost of one glass of red wine each day versus one resveratrol pill each day and how that may impact alimentary allocation standard 152. One or more database tables contained within interchange database 924 is nutrition table 1008; nutrition table 1008 may include any and all information pertaining to how substitution of a particular food and/or supplement within alimentary instruction set may affect nutrition state of a user and/or equivalency in obtaining a specific nutrient through food versus supplementation. Nutrition table 1008 may be consulted to determine to determine how a different food and/or supplement may affect a prognostic label, ameliorative process label, and/or diagnostic output. For example, nutrition table 1008 may be consulted to determine how many oranges a user may need to consume each week to absorb enough antioxidants versus taking an antioxidant supplement. One or more database tables contained within interchange database 924 is availability table 1012; availability table 1012 may contain information pertaining to availability of a certain food and/or supplement for a particular user. For example, a user living in Hawaii may have access to fresh macadamia nuts year round while a user living in Nebraska may not be able to obtain macadamia nuts and may have take a supplement containing Vitamin E and selenium, two nutrients commonly found in macadamia nuts instead. One or more database tables contained within interchange database 924 is dosage form table 1016; dosage form table 1016 may contain information pertaining to dosage form of foods and/or supplements contained within alimentary instruction set 144. Dosage form table 1016 may be consulted to determine if a certain supplement comes in a certain dosage form such as for example a capsule or tablet versus a liquid form. Dosage form table 1016 may be consulted to determine if a certain food comes in a certain dosage form such as loose carrots versus carrot juice. One or more database tables contained within interchange database 924 is quality table 1020; quality table 1020 may contain information pertaining to quality of certain foods and/or supplements. Quality table 1020 may include information such as if a particular food was grown organically or was locally produced and if a certain supplement was manufactured under certain conditions. Quality table 1020 may be consulted to determine if a certain food and/or supplement may affect a user input such as alimentary quality standard 150. For example, a user may have an alimentary quality standard 150 that includes a preference for organic products. In such an instance, quality table 1020 may be consulted to determine if a particular supplement was organically produced so as to meet user input. One or more database tables contained within interchange database 924 is dose table 1024; dose table 1024 may contain information pertaining to specific quantities of a food that may need to be consumed to receive a certain dose of a nutrient contained as well as a certain dose of supplements that may need to be consumed to receive a certain dose of a nutrient contained within the supplement. For example, dose table 1024 may contain information such as how many almonds a user may need to consume in order to obtain 400 International Units of Vitamin E daily versus how many Vitamin E softgels a user may need to take in order to obtain 400 IU of Vitamin E daily while taking a specific brand of Vitamin E.

Figure 11:
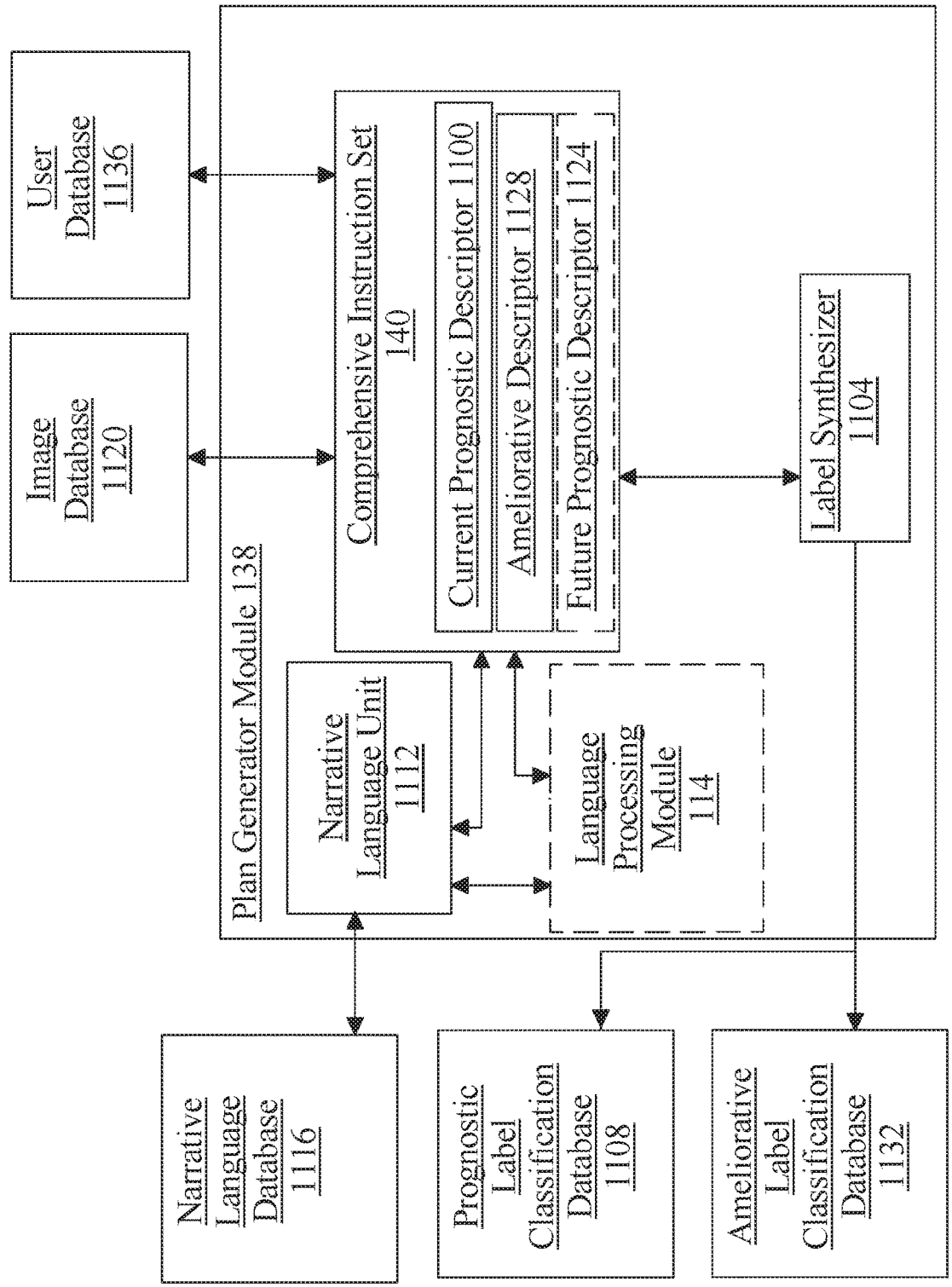
FIG. 11 is a block diagram illustrating an exemplary embodiment of a plan generator module and associated system elements.

Referring now to FIG. 11, an exemplary embodiment of a plan generator module 138 is illustrated. Comprehensive instruction set 140 includes at least a current prognostic descriptor 1100 which as used in this disclosure is an element of data describing a current prognostic status based on at least one prognostic output. Plan generator module 138 may produce at least a current prognostic descriptor 1100 using at least a prognostic output. In an embodiment, plan generator module 138 may include a label synthesizer 1104. Label synthesizer 1104 may include any suitable software or hardware module. In an embodiment, label synthesizer 1104 may be designed and configured to combine a plurality of labels in at least a prognostic output together to provide maximally efficient data presentation. Combination of labels together may include elimination of duplicate information. For instance, label synthesizer 1104 and/or at least a server 102 may be designed and configure to determine a first prognostic label of the at least a prognostic label is a duplicate of a second prognostic label of the at least a prognostic label and eliminate the first prognostic label. Determination that a first prognostic label is a duplicate of a second prognostic label may include determining that the first prognostic label is identical to the second prognostic label; for instance, a prognostic label generated from test data presented in one biological extraction of at least a biological extraction may be the same as a prognostic label generated from test data presented in a second biological extraction of at least a biological extraction. As a further non-limiting example, a first prognostic label may be synonymous with a second prognostic label, where detection of synonymous labels may be performed, without limitation, by a language processing module 114 as described above.

Continuing to refer to FIG. 11, label synthesizer 1104 may group prognostic labels according to one or more classification systems relating the prognostic labels to each other. For instance, plan generator module 138 and/or label synthesizer 1104 may be configured to determine that a first prognostic label of the at least a prognostic label and a second prognostic label of the at least a prognostic label belong to a shared category. A shared category may be a category of conditions or tendencies toward a future condition to which each of first prognostic label and second prognostic label belongs; as an example, lactose intolerance and gluten sensitivity may each be examples of digestive sensitivity, for instance, which may in turn share a category with food sensitivities, food allergies, digestive disorders such as celiac disease and diverticulitis, or the like. Shared category and/or categories may be associated with prognostic labels as well. A given prognostic label may belong to a plurality of overlapping categories. Plan generator module 138 may be configured to add a category label associated with a shared category to comprehensive instruction set 140, where addition of the label may include addition of the label and/or a datum linked to the label, such as a textual or narrative description. In an embodiment, relationships between prognostic labels and categories may be retrieved from a prognostic label classification database 1108, for instance by generating a query using one or more prognostic labels of at least a prognostic output, entering the query, and receiving one or more categories matching the query from the prognostic label classification database 1108.

Figure 12:
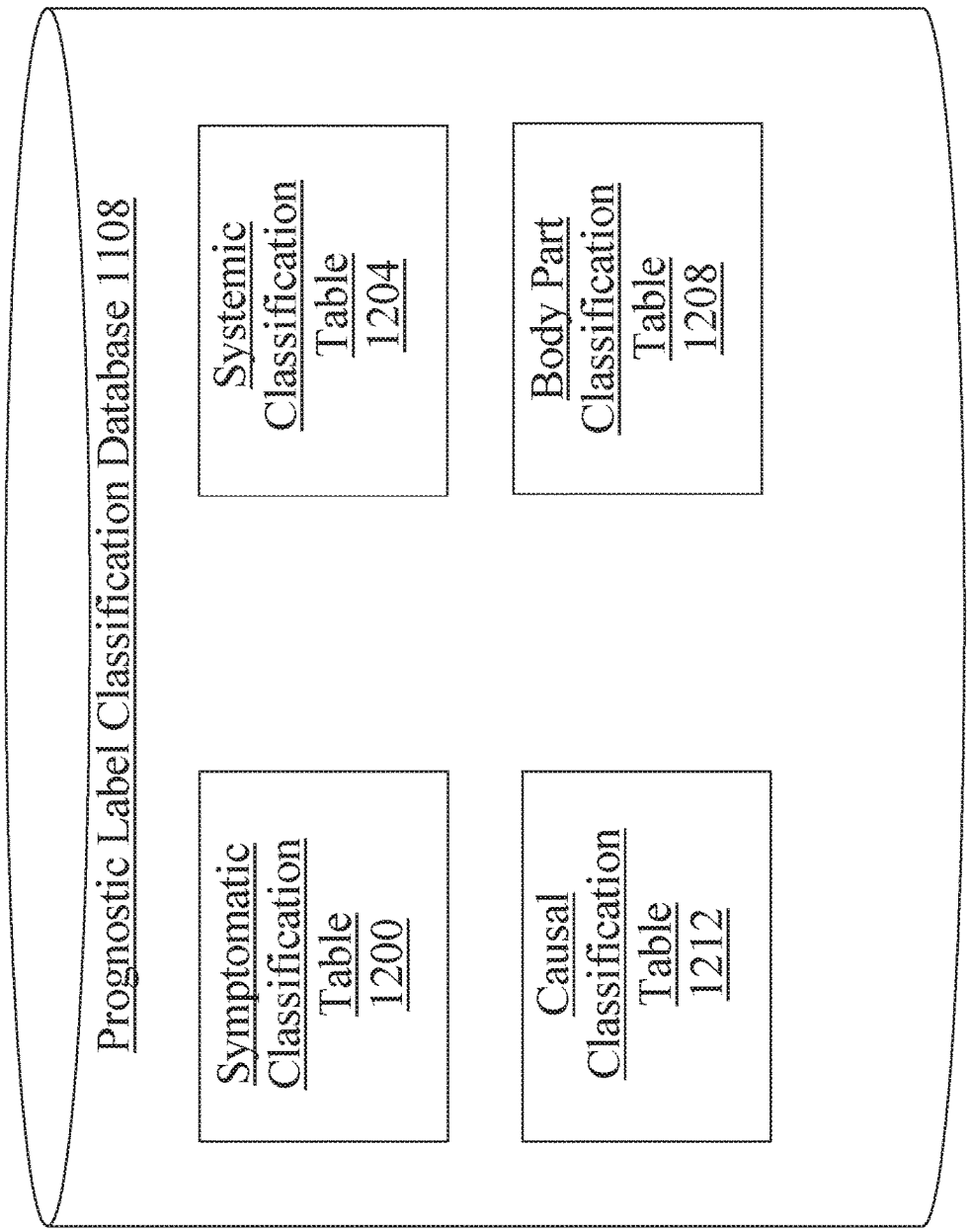
FIG. 12 is a block diagram illustrating an exemplary embodiment of a prognostic label classification database.

Referring now to FIG. 12, an exemplary embodiment of a prognostic label classification database 1108 is illustrated. Prognostic label classification database 1108 may be implemented as any database and/or datastore suitable for use as biological extraction database 200 as described above. One or more database tables in prognostic label classification database 1108 may include, without limitation, a symptomatic classification table 1200; symptomatic classification table 1200 may relate each prognostic label to one or more categories of symptoms associated with that prognostic label. As a non-limiting example, symptomatic classification table 1200 may include records indicating that each of lactose intolerance and gluten sensitivity results in symptoms including gas buildup, bloating, and abdominal pain. One or more database tables in prognostic label classification database 1108 may include, without limitation, a systemic classification table 1204; systemic classification table 1204 may relate each prognostic label to one or more systems associated with that prognostic label. As a non-limiting example, systemic classification table 1204 may include records indicating each of lactose intolerance and gluten sensitivity affects the digestive system; two digestive sensitivities linked to allergic or other immune responses may additionally be linked in systemic classification table 1204 to the immune system. One or more database tables in prognostic label classification database 1108 may include, without limitation, a body part classification table 1008; body part classification table 1208 may relate each prognostic label to one or more body parts associated with that prognostic label. As a non-limiting example, body part classification table 1208 may include records indicating each of psoriasis and rosacea affects the skin of a person. One or more database tables in prognostic label classification database 1108 may include, without limitation, a causal classification table 1212; causal classification table 1212 may relate each prognostic label to one or more causes associated with that prognostic label. As a non-limiting example, causal classification table 1212 may include records indicating each of type 2 diabetes and hypertension may have obesity as a cause. The above-described tables, and entries therein, are provided solely for exemplary purposes. Persons skilled in the art, upon reviewing the entirety of this disclosure, will be aware of various additional examples for tables and/or relationships that may be included or recorded in prognostic classification table consistently with this disclosure.

Referring again to FIG. 11, plan generator module 138 may be configured to generate current prognostic descriptor 1100 by converting one or more prognostic labels into narrative language. As a non-limiting example, plan generator module 138 may include a narrative language unit 1112, which may be configured to determine an element of narrative language associated with at least a prognostic label and include the element of narrative language in current prognostic label descriptor. Narrative language unit 1112 may implement this, without limitation, by using a language processing module 114 to detect one or more associations between prognostic labels, or lists of prognostic labels, and phrases and/or statements of narrative language. Alternatively or additionally, narrative language unit 1112 may retrieve one or more elements of narrative language from a narrative language database 1116, which may contain one or more tables associating prognostic labels and/or groups of prognostic labels with words, sentences, and/or phrases of narrative language. One or more elements of narrative language may be included in comprehensive instruction set 140, for instance for display to a user as text describing a current prognostic status of the user. Current prognostic descriptor 1100 may further include one or more images; one or more images may be retrieved by plan generator module 138 from an image database 1120, which may contain one or more tables associating prognostic labels, groups of prognostic labels, current prognostic descriptors 1100, or the like with one or more images.

With continued reference to FIG. 11, comprehensive instruction set 140 may include one or more follow-up suggestions, which may include, without limitation, suggestions for acquisition of an additional biological extraction; in an embodiment, additional biological extraction may be provided to diagnostic engine 104, which may trigger repetition of one or more processes as described above, including without limitation generation of prognostic output, refinement or elimination of ambiguous prognostic labels of prognostic output, generation of ameliorative output, and/or refinement or elimination of ambiguous ameliorative labels of ameliorative output. For instance, where a pegboard test result suggests possible diagnoses of Parkinson's disease, Huntington's disease, ALS, and MS as described above, follow-up suggestions may include suggestions to perform endocrinal tests, genetic tests, and/or electromyographic tests; results of such tests may eliminate one or more of the possible diagnoses, such that a subsequently displayed output only lists conditions that have not been eliminated by the follow-up test. Follow-up tests may include any receipt of any biological extraction as described above.

With continued reference to FIG. 11, comprehensive instruction set 140 may include one or more elements of contextual information, including without limitation any patient medical history such as current lab results, a current reason for visiting a medical professional, current status of one or more currently implemented treatment plans, biographical information concerning the patient, and the like. One or more elements of contextual information may include goals a patient wishes to achieve with a medical visit or session, and/or as result of interaction with diagnostic engine 104. Contextual information may include one or more questions a patient wishes to have answered in a medical visit and/or session, and/or as a result of interaction with diagnostic engine 104. Contextual information may include one or more questions to ask a patient. Persons skilled in the art, upon reviewing the entirety of this disclosure, will be aware of various forms of contextual information that may be included, consistently with this disclosure.

With continued reference to FIG. 11, comprehensive instruction set 140 may include at least a future prognostic descriptor 1124. As used herein, a future prognostic descriptor 1124 is an element of data describing a future prognostic status based on at least one prognostic output, which may include without limitation a desired further prognostic status. In an embodiment, future prognostic descriptor 1124 may include any element suitable for inclusion in current prognostic descriptor 1100. Future prognostic descriptor 1124 may be generated using any processes, modules, and/or components suitable for generation of current prognostic descriptor 1100 as described above.

Still referring to FIG. 11, comprehensive instruction set 140 includes at least an ameliorative process descriptor 1128, which as defined in this disclosure an element of data describing one or more ameliorative processes to be followed based on at least one ameliorative output; at least an ameliorative process descriptor 1128 may include descriptors for ameliorative processes usable to achieve future prognostic descriptor 1124. Plan generator module 138 may produce at least an ameliorative process descriptor 1128 using at least a prognostic output. In an embodiment, label synthesizer 1104 may be designed and configured to combine a plurality of labels in at least an ameliorative output together to provide maximally efficient data presentation. Combination of labels together may include elimination of duplicate information. For instance, label synthesizer 1104 and/or at least a server 102 may be designed and configure to determine a first ameliorative label of the at least an ameliorative label is a duplicate of a second ameliorative label of the at least an ameliorative label and eliminate the first ameliorative label. Determination that a first ameliorative label is a duplicate of a second ameliorative label may include determining that the first ameliorative label is identical to the second ameliorative label; for instance, a ameliorative label generated from test data presented in one biological extraction of at least a biological extraction may be the same as a ameliorative label generated from test data presented in a second biological extraction of at least a biological extraction. As a further non-limiting example, a first ameliorative label may be synonymous with a second ameliorative label, where detection of synonymous labels may be performed, without limitation, by a language processing module 114 as described above.

Continuing to refer to FIG. 11, label synthesizer 1104 may group ameliorative labels according to one or more classification systems relating the ameliorative labels to each other. For instance, plan generator module 138 and/or label synthesizer 1104 may be configured to determine that a first ameliorative label of the at least an ameliorative label and a second ameliorative label of the at least an ameliorative label belong to a shared category. A shared category may be a category of conditions or tendencies toward a future condition to which each of first ameliorative label and second ameliorative label belongs; as an example, lactose intolerance and gluten sensitivity may each be examples of digestive sensitivity, for instance, which may in turn share a category with food sensitivities, food allergies, digestive disorders such as celiac disease and diverticulitis, or the like. Shared category and/or categories may be associated with ameliorative labels as well. A given ameliorative label may belong to a plurality of overlapping categories. Plan generator module 138 may be configured to add a category label associated with a shared category to comprehensive instruction set 140, where addition of the label may include addition of the label and/or a datum linked to the label, such as a textual or narrative description. In an embodiment, relationships between ameliorative labels and categories may be retrieved from an ameliorative label classification database 1132, for instance by generating a query using one or more ameliorative labels of at least an ameliorative output, entering the query, and receiving one or more categories matching the query from the ameliorative label classification database 1132.

Figure 13:
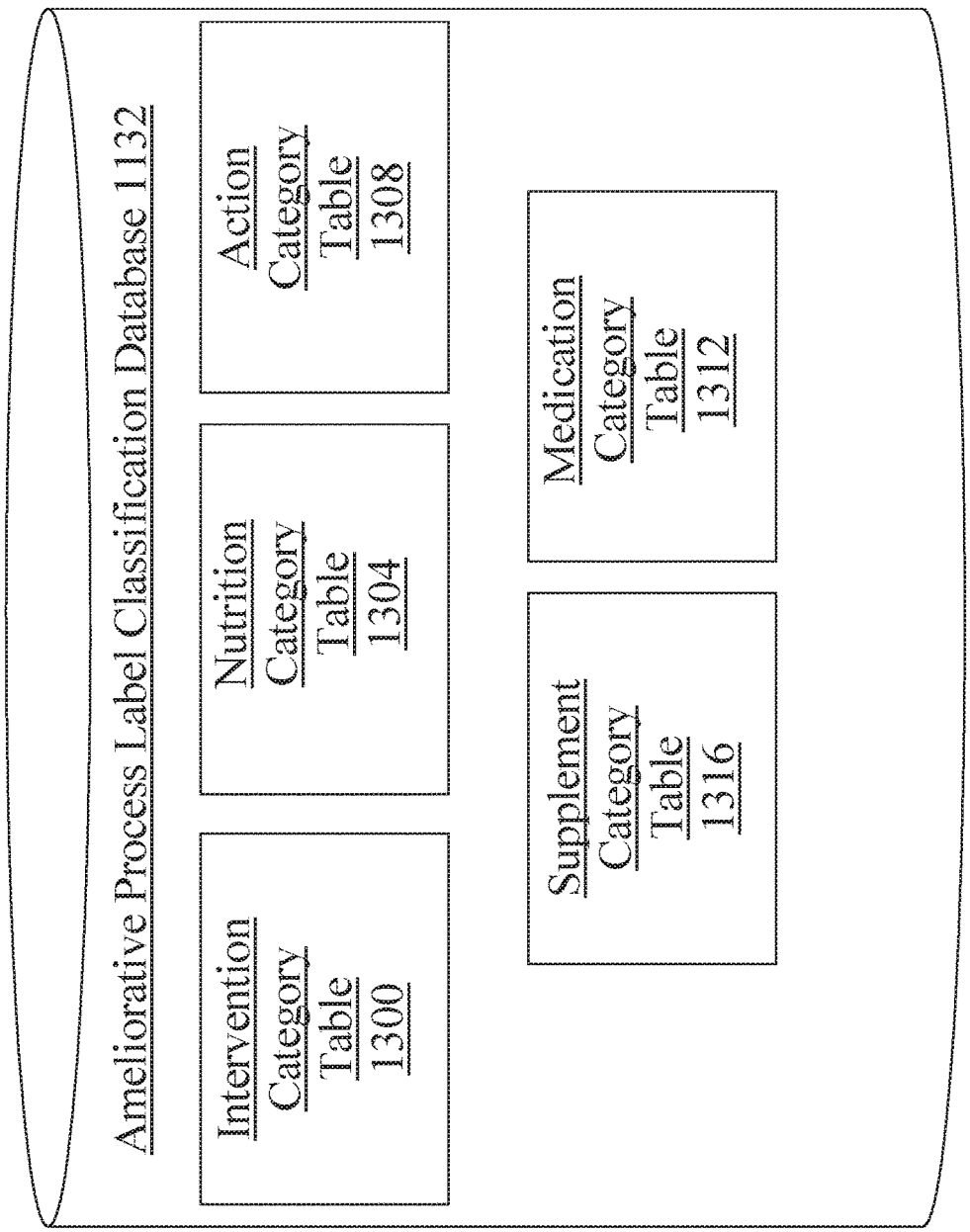
FIG. 13 is a block diagram illustrating an exemplary embodiment of an ameliorative process label classification database.

Referring now to FIG. 13, an exemplary embodiment of an ameliorative label classification database 1132 is illustrated. Ameliorative label classification database 1132 may be implemented as any database and/or datastore suitable for use as biological extraction database 200 as described above. One or more database tables in ameliorative label classification database 1132 may include, without limitation, an intervention category table 1300; intervention category table 1300 may relate each ameliorative label to one or more categories associated with that ameliorative label. As a non-limiting example, intervention category table 1300 may include records indicating that each of a plan to consume a given quantity of almonds and a plan to consume less meat maps to a category of nutritional instruction, while a plan to jog for 30 minutes per day maps to a category of activity. One or more database tables in ameliorative label classification database 1132 may include, without limitation, a nutrition category table 1304; nutrition category table 1304 may relate each ameliorative label pertaining to nutrition to one or more categories associated with that ameliorative label. As a non-limiting example, nutrition category table 1304 may include records indicating that each of a plan to consume more almonds and a plan to consume more walnuts qualifies as a plan to consume more nuts, as well as a plan to consume more protein. One or more database tables in ameliorative label classification database 1132 may include, without limitation, an action category table 1308; action category table 1308 may relate each ameliorative label pertaining to an action to one or more categories associated with that ameliorative label. As a non-limiting example, action category table 1308 may include records indicating that each of a plan jog for 30 minutes a day and a plan to perform a certain number of sit-ups per day qualifies as an exercise plan. One or more database tables in ameliorative label classification database 1132 may include, without limitation, a medication category table 1312; medication category table 1312 may relate each ameliorative label associated with a medication to one or more categories associated with that ameliorative label. As a non-limiting example, medication category table 1312 may include records indicating that each of a plan to take an antihistamine and a plan to take an anti-inflammatory steroid belongs to a category of allergy medications. One or more database tables in ameliorative label classification database 1132 may include, without limitation, a supplement category table 1316; supplement category table 1316 may relate each ameliorative label pertaining to a supplement to one or more categories associated with that ameliorative label. As a non-limiting example, supplement category table 1316 may include records indicating that each of a plan to consume a calcium supplement and a plan to consume a vitamin D supplement corresponds to a category of supplements to aid in bone density. Ameliorative labels may be mapped to each of nutrition category table 1304, action category table 1308, supplement category table 1316, and medication category table 1312 using intervention category table 1300. The above-described tables, and entries therein, are provided solely for exemplary purposes. Persons skilled in the art, upon reviewing the entirety of this disclosure, will be aware of various additional examples for tables and/or relationships that may be included or recorded in ameliorative classification table consistently with this disclosure.

Referring again to FIG. 11, plan generator module 138 may be configured to generate ameliorative process descriptor 1128 by converting one or more ameliorative labels into narrative language. As a non-limiting example, plan generator module 138 may include a narrative language unit 1112, which may be configured to determine an element of narrative language associated with at least an ameliorative label and include the element of narrative language in current ameliorative label descriptor. Narrative language unit 1112 may implement this, without limitation, by using a language processing module 114 to detect one or more associations between ameliorative labels, or lists of ameliorative labels, and phrases and/or statements of narrative language. Alternatively or additionally, narrative language unit 1112 may retrieve one or more elements of narrative language from narrative language database 1116, which may contain one or more tables associating ameliorative labels and/or groups of ameliorative labels with words, sentences, and/or phrases of narrative language. One or more elements of narrative language may be included in comprehensive instruction set 140, for instance for display to a user as text describing a current ameliorative status of the user. Ameliorative process descriptor 1128 may further include one or more images; one or more images may be retrieved by plan generator module 138 from an image database 1120, which may contain one or more tables associating ameliorative labels, groups of ameliorative labels, ameliorative process descriptors 1028, or the like with one or more images.

Figure 14:
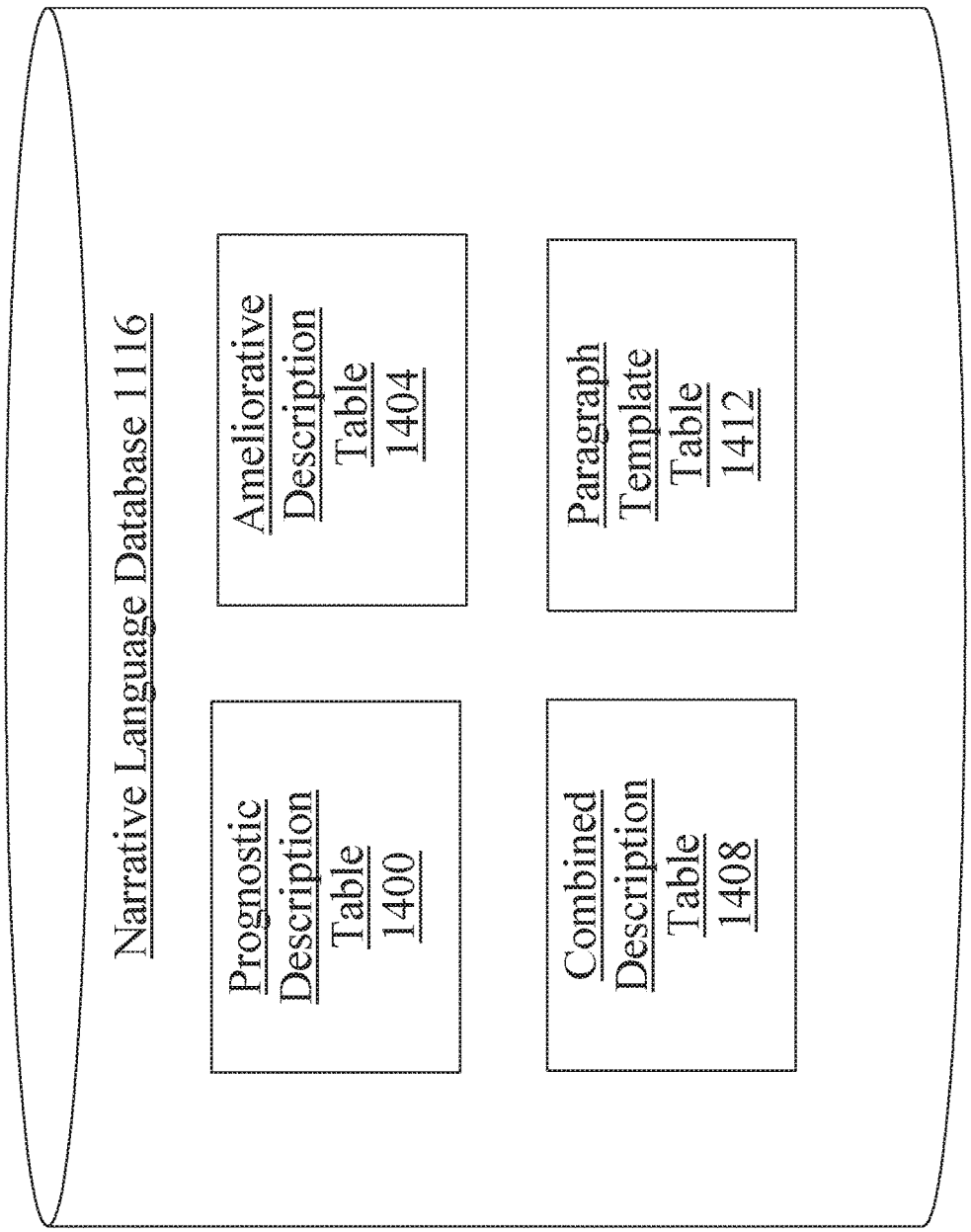
FIG. 14 is a block diagram illustrating an exemplary embodiment of a narrative language database.

Referring now to FIG. 14, and exemplary embodiment of a narrative language database 1116 is illustrated. Narrative language database 1116 may be implemented as any database and/or datastore suitable for use as biological extraction database 200 as described above. One or more database tables in narrative language database 1116 may include, without limitation, a prognostic description table 1400, which may link prognostic labels to narrative descriptions associated with prognostic labels. One or more database tables in narrative language database 1116 may include, without limitation, an ameliorative description table 1404, which may link ameliorative process labels to narrative descriptions associated with ameliorative process labels. One or more database tables in narrative language database 1116 may include, without limitation, a combined description table 1408, which may link combinations of prognostic labels and ameliorative labels to narrative descriptions associated with the combinations. One or more database tables in narrative language database 1116 may include, without limitation, a paragraph template table 1412, which may contain one or more templates of paragraphs, pages, reports, or the like into which images and text, such as images obtained from image database 1120 and text obtained from prognostic description table 1400, ameliorative description table 1404, and combined description table 1408 may be inserted. Tables in narrative language database 1116 may be populated, as a non-limiting example, using submissions from experts, which may be collected according to any processes described above. Persons skilled in the art, upon reviewing the entirety of this disclosure, will be aware of various way sin which entries in narrative language database 1116 may be categorized and/or organized.

Figure 15:
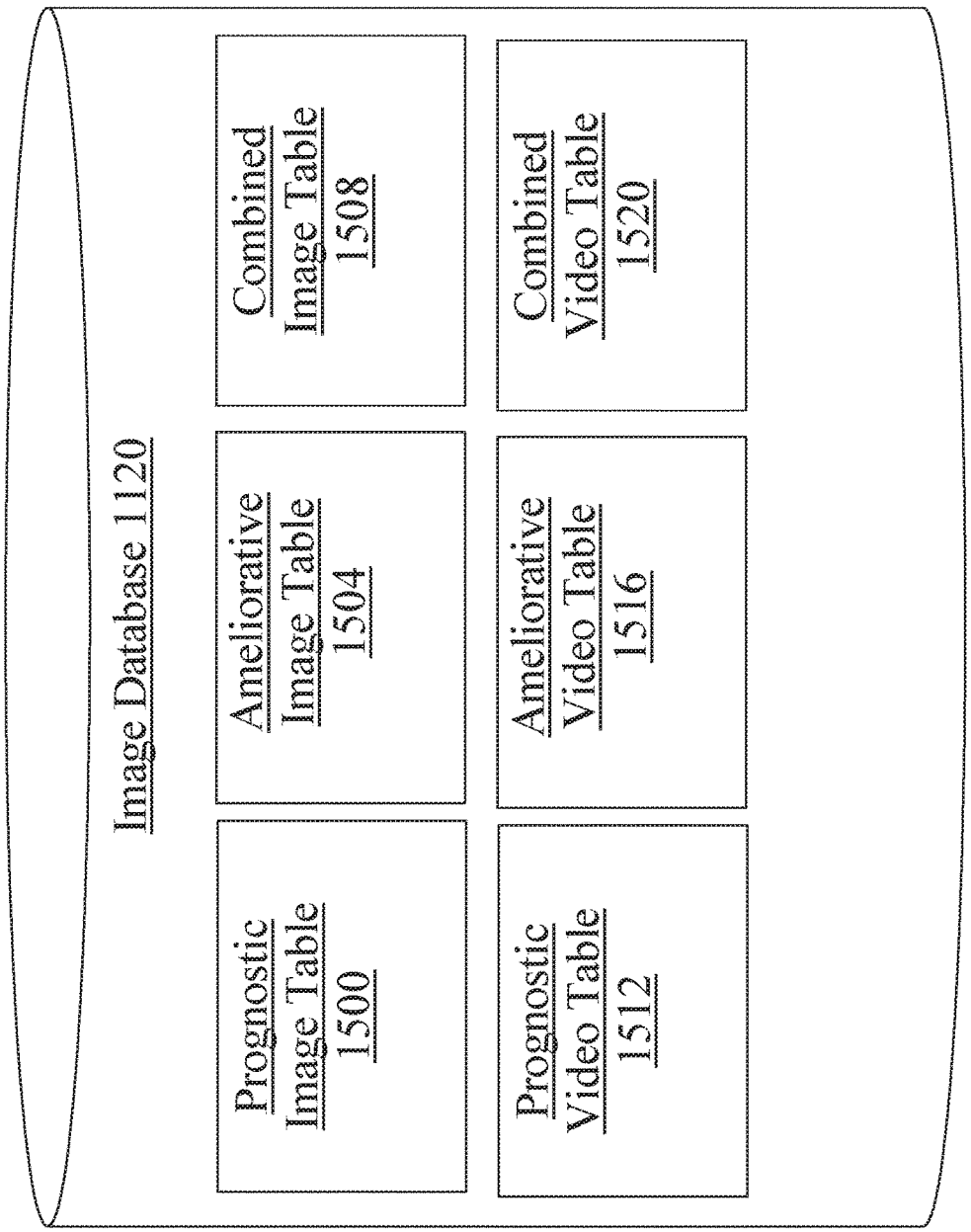
FIG. 15 is a block diagram illustrating an exemplary embodiment of an image database.

Referring now to FIG. 15, an exemplary embodiment of an image database 1120 is illustrated. Image database 1120 may be implemented as any database and/or datastore suitable for use as biological extraction database 200 as described above. One or more database tables in image database 102 may include, without limitation, a prognostic image table 1500, which may link prognostic labels to images associated with prognostic labels. One or more database tables in image database 1120 may include, without limitation, an ameliorative image table 1504, which may link ameliorative process labels to images associated with ameliorative process labels. One or more database tables in image database 1120 may include, without limitation, a combined description table 1508, which may link combinations of prognostic labels and ameliorative labels to images associated with the combinations. One or more database tables in image database 102 may include, without limitation, a prognostic video table 1512, which may link prognostic labels to videos associated with prognostic labels. One or more database tables in image database 1120 may include, without limitation, an ameliorative video table 1516, which may link ameliorative process labels to videos associated with ameliorative process labels. One or more database tables in image database 1120 may include, without limitation, a combined video table 1520, which may link combinations of prognostic labels and ameliorative labels to videos associated with the combinations. Tables in image database 1120 may be populated, without limitation, by submissions by experts, which may be provided according to any process or process steps described in this disclosure for collection of expert submissions.

Figure 16:
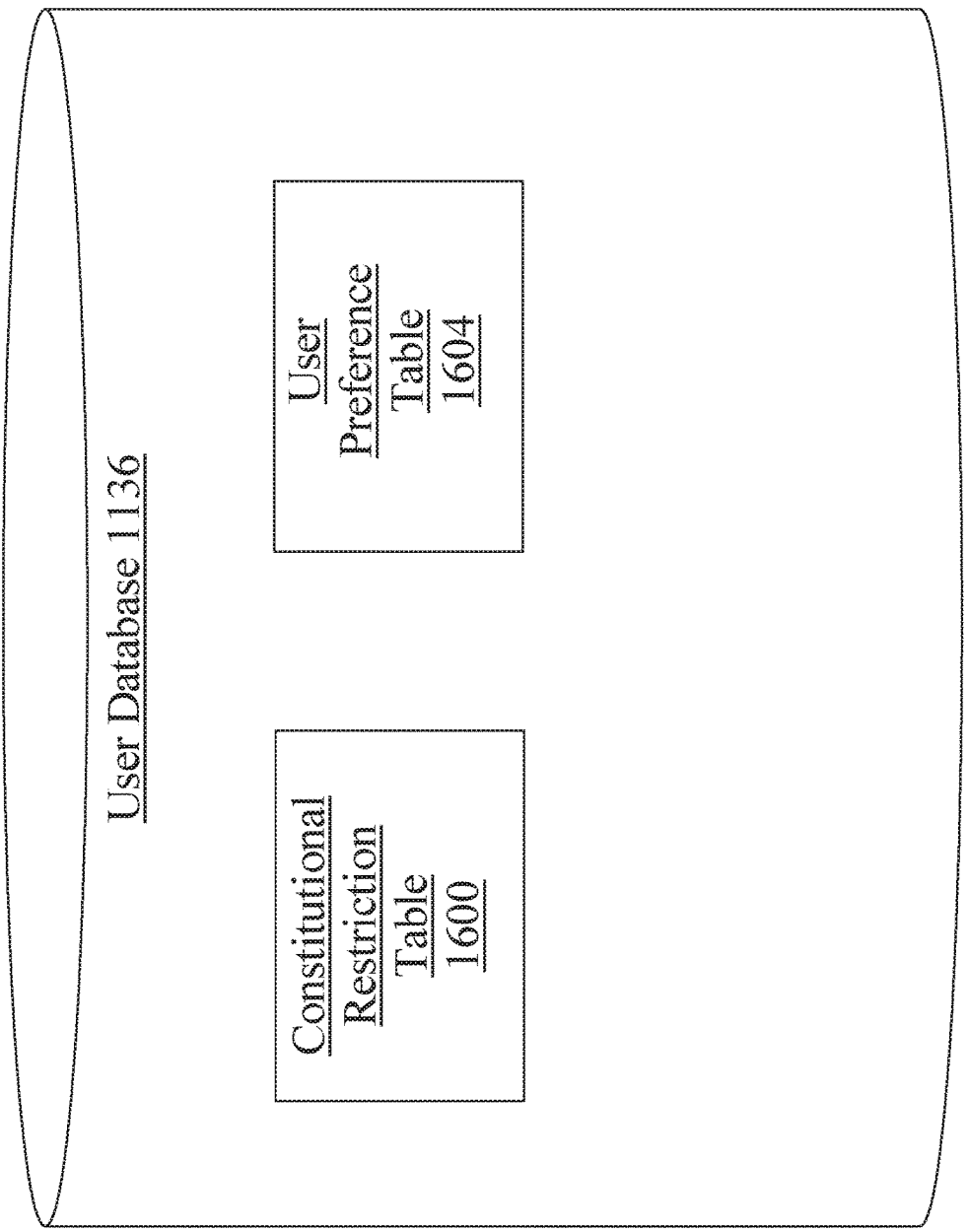
FIG. 16 is a block diagram illustrating an exemplary embodiment of a user database.

Referring to FIG. 16, an exemplary embodiment of a user database 1136 is illustrated. User database 1136 may be implemented as any database and/or datastore suitable for use as described above. One or more database tables in user database 1136 may include, without limitation, a constitution restriction table 1600; at least a constitutional restriction may be linked to a given user and/or user identifier in a constitutional restriction table 1600. One or more database tables in user database 1136 may include, without limitation, a user preference table 1604; at least a user preference may be linked to a given user and/or user identifier in a user preference table 1604.

Figure 17:
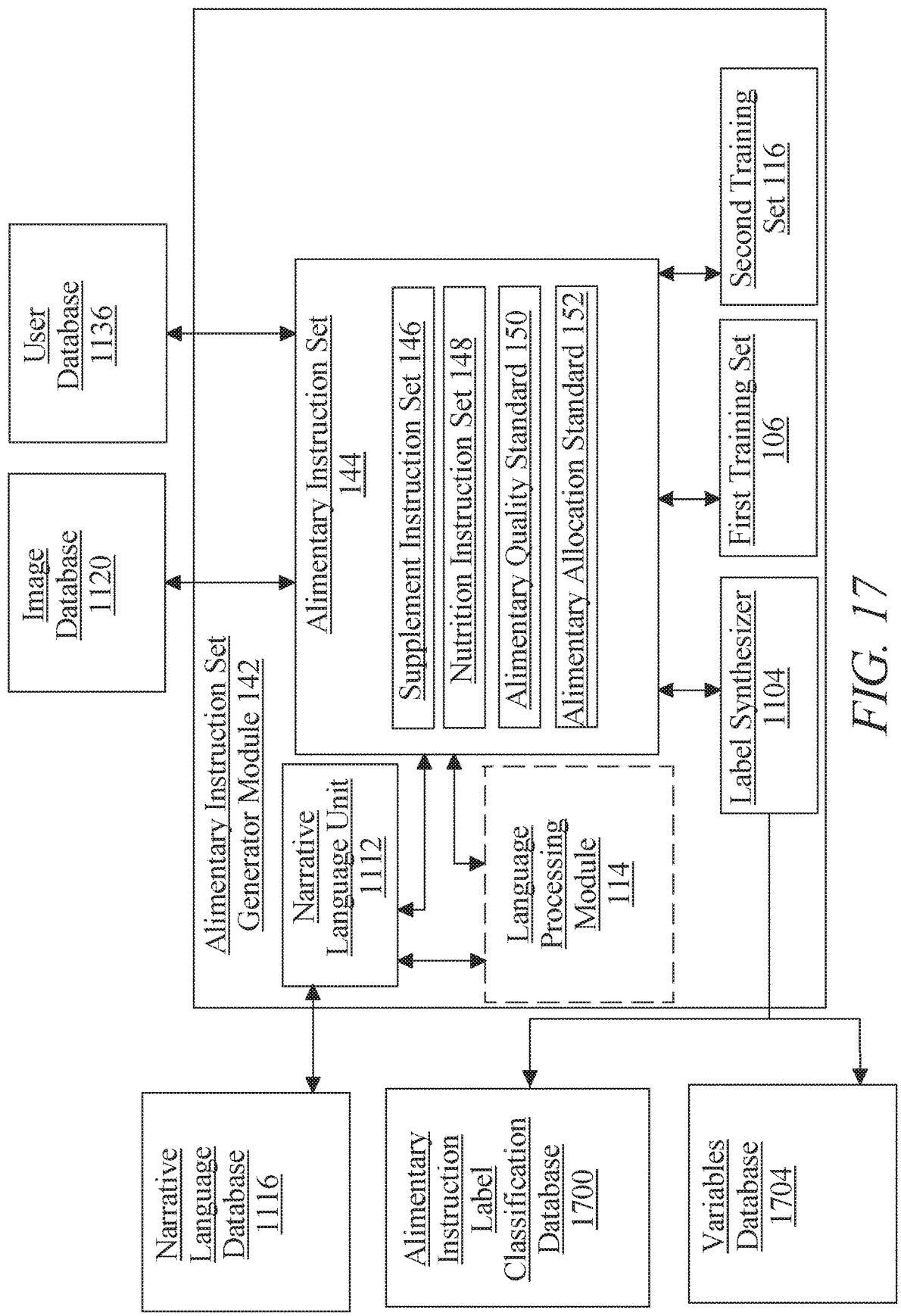
FIG. 17 is a block diagram illustrating an exemplary embodiment of an alimentary instruction set module and associated system elements.

Referring now to FIG. 17, an exemplary embodiment of alimentary instruction set module 142 is illustrated. In one embodiment, the alimentary instruction set generator module 142 may be configured to receive at least a user input and generate at least an alimentary instruction set comprising a plurality of information reflecting a comprehensive list of meals, supplements, and processes aimed towards resolving any identified issues, suggestions, or deficiencies as a function of the comprehensive instruction set 140. In an embodiment, alimentary instruction set generator module may include a label synthesizer 1104 as described above.

Continuing to refer to FIG. 17, alimentary instruction set generator module 142 is designed and configured to an alimentary instruction set 144 based on comprehensive instruction set 140. In an embodiment, alimentary instruction set generator module 142 may generate alimentary instruction set 144 based on the integration of data associated with comprehensive instruction set 140, and at least a user input. Generation of alimentary instruction set 144 may include identification of one or more alimentary instructions in comprehensive instruction set, and insertion of the one or more alimentary instructions in the alimentary instruction set 144; for instance, alimentary instruction set 144 may be formed, wholly or partially, by aggregating alimentary instructions from comprehensive instruction set 140 and combining the aggregated alimentary instructions using narrative language module, narrative language database, image database, or the like, according to any process suitable for generation of comprehensive instruction set as described above.

With continued reference to FIG. 17, alimentary instruction set generator module 142 may generate alimentary instruction set 144 based on alimentary data and non-alimentary data in order to facilitate both medicinal and holistic components in alimentary instruction set 144 specifics to a user. In one embodiment, alimentary data may be identified and aggregated into a subset of applicable alimentary data based on at least a biological extraction and comprehensive instruction set 140. In application, alimentary instruction set 144 may comprise a plurality of alimentary data specific to user that is able to be used by machine learning and artificial intelligence systems in order to continuously update or modify training sets, and ultimately comprehensive instruction set 140 and alimentary instruction set 144 based on updated or progressions associated with implementation of alimentary instruction set 144 by user. Alimentary data and non-alimentary data may include compilations of instruction sets received over a period of time, the compilations may account for improvements or modifications associated with user. Alimentary instruction set 144 may further include instructions over time, in which the alimentary instructions may change in response to changes in a user's data and/or prognosis. Alternatively or additionally, system 100 may periodically iterate through one or more processes as described in this disclosure, such that repeated reevaluations may modify alimentary instruction set 144 as information concerning user and/or biological extractions obtained from the user change over time.

With continued reference to FIG. 17, alimentary instruction set 144 may be generated by alimentary instruction set generator module 142 utilizing at least a user input. User input may include any of the user inputs as described above in reference to FIG. 1. This may include for example, an input as to alimentary quality standard, alimentary allocation standard, and the like. In an embodiment, alimentary instruction set generator module 142 may utilize machine learning and artificial intelligence systems in order to generate alimentary instruction sets as a function of user inputs. Alimentary instruction set generator module 142 may utilize training sets that includes a first training set that includes a first data entry including any item contained within an alimentary instruction set such as a food, ingredient, supplement, and the like and a correlated effect on one's health. Alimentary instruction set generator module 142 may utilize a second training set that includes a second data entry including any item contained within an alimentary instruction set such as a food, ingredient, supplement, and a correlated price and/or effect on alimentary allocation standard.

With continued reference to FIG. 17, alimentary instruction set generator module 142 may identify a non-alimentary instruction within comprehensive instruction set 140, determine an alimentary analog to the non-alimentary instruction and introduce the alimentary analog into the alimentary instruction set and/or use the alimentary analog to update the self-fulfillment instruction set. An alimentary analog, as used herein, is an alimentary process or instruction that achieves a similar purpose to a non-alimentary process and/or instruction. As a non-limiting example, certain foods such as grapefruit may act to lower blood sugar; where the impact of consuming a particular quantity of such foods is similar to or the same as an impact of consuming a blood sugar medication, the former may be an alimentary analog of the latter. In one embodiment, non-alimentary data within comprehensive instruction set 140 may be subsequently substituted in alimentary instruction set 144 with alimentary data configured to provide user with holistic solutions to issues that were initially treated with non-holistic approaches. For example, if initially diagnostic output indicates that the blood sugar of user is abnormally high then comprehensive instruction set 140 may recommend that user take applicable medications classified as non-alimentary in order to lower the blood sugar immediately. However, alimentary instruction set 144 may subsequently or concurrently provide one or more sets of instructions to remedy the improved blood sugar of user via an alimentary solution such as increased consumption of grapefruits, configured to be executed by a user. As a further example, a supplement initially presented in comprehensive instruction set 140 may be subsequently replaced, in alimentary instruction set 144, by a specific food categorized as alimentary in order to remedy the issues in which the initial supplement sought to address. In another example, alimentary data and alimentary solutions may be incorporated into alimentary instruction set 144 upon one or more determinations that the alimentary data and implementations of the alimentary solution are more efficient than non-alimentary solutions initially included in alimentary instruction set 144. Alimentary data and alimentary solutions may also be substituted for less efficient alimentary solutions. For example, if user, based on comprehensive instruction set 140, is deemed to need a boost in HDL, then a secondary alimentary solution of eating certain foods may be determined more efficient than a primary alimentary solution of increasing cardio activity.

Still referring to FIG. 17, alimentary instruction set generator module 142 may generate alimentary instruction set 144, at least in part, by identifying at least a negative effect associated with an ameliorative instruction of comprehensive instruction set 140; at least a negative effect may include a "side-effect" of an ameliorative process, such as a side effect of a medication, an increase risk of a type of injury associated with an exercise program, or the like. Alimentary instruction set generator module 142 may determine an alimentary instruction that alleviates the at least a negative effect; for instance, a side-effect of a medication may be alleviated and/or prevented by consumption of an alimentary element tending to alleviate the side-effect. As a non-limiting example, a medication that may cause fluid retention and edema may be provided in comprehensive instruction set 140; alimentary instruction set generator module 142 may determine that consumption of an alimentary element having a diuretic effect, such as a food or drink containing caffeine, may act to prevent or alleviate fluid retention. As a further non-limiting example, comprehensive instruction set 140 may include an instruction for a user to increase his or her exercise regimen, or to begin a new regimen of regular exercise; a counterindication and/or other element of data may indicate an elevated risk of joint injury and/or inflammation as a result of the increased exercise, which may be alleviated or prevented by a lower-calorie diet, consumption of foods containing glucosamine or some other ingredient associated with a reduced risk of joint pain.

With continued reference to FIG. 17, alimentary instruction set generator module 142 may generate alimentary instruction set 144 at least in part by identifying at least a negative effect associated with an ameliorative instruction of comprehensive instruction set 140 and analyzing alimentary quality standard 150. For example, a user consuming a supplement containing vitamin C who complains of a "side effect" of upset stomach may be switched to consume dietary sources of Vitamin C based on alimentary allocation standard. For example, if dietary sources of Vitamin C cause the user to exceed the alimentary allocation standard then the user may be instructed to consume Vitamin C with food to minimize upset stomach if possible. In yet another non-limiting example, a user who consumes a paleo diet and who develops gallstones may be switched to a different diet such as a low fat plant based diet as a function of alimentary allocation standard. In such an instance, alimentary allocation standard may determine percentage of fresh versus frozen vegetables a user may be able to purchase and consume, quantity of plant products a user may be able to purchase and consume that are organic, as well as lean sources of protein that fit within user's alimentary allocation standard including for example, tofu, black beans, and lentils. In yet another non-limiting example, a user consuming a supplement or food that experiences a negative "side effect" may be switched to another brand of a supplement or food to see if user still experiences negative symptoms. In such an instance, brand that a user may be switched to may be selection as a function of alimentary allocation standard. In an embodiment if user continues to experience negative symptoms then supplement or food may be stopped altogether.

Continuing to refer to FIG. 17, alimentary instruction set generator module 142 may determine an alimentary instruction that alleviates the at least a negative effect using machine-learning processes and/or modules as described above; for instance, and without limitation, alimentary instruction set generator module 142 may provide at least a negative effect to ameliorative process label learner and/or alimentary instruction set label leaner in the form of at least a prognostic label; ameliorative process label learner and/or alimentary instruction set label leaner may generate one or more ameliorative labels associated with an alimentary process for alleviating the at least a negative effect.

Continuing to refer to FIG. 17, label synthesizer 1104 may group alimentary labels according to one or more classification systems relating the alimentary labels to each other. For instance, plan generator module 138 and/or label synthesizer 1104 may be configured to determine that a first alimentary label of the at least an alimentary label and a second alimentary label of the at least an alimentary label belong to a shared category. A shared category may be a category of alimentary elements to which each of first alimentary label and second alimentary label belongs; for instance, a first alimentary label associated with tofu and a second alimentary label associated with nuts may each be grouped as a protein source. A given alimentary label may belong to a plurality of overlapping categories. In an embodiment, alimentary labels may be categorized as to how they may fit into an alimentary allocation standard. For example, an alimentary label may have a high impact on an alimentary allocation standard when it may contain organic ingredients, pure supplements and/or locally produced products which may account for a larger portion of the total alimentary allocation standard. In yet another non-limiting example, alimentary label may have a low impact on an alimentary allocation standard such as when it may contain frozen vegetables or homegrown vegetables and may account for a smaller portion of the total alimentary allocation standard. In yet another non-limiting example, alimentary label may an impact on alimentary allocation standard as a function of user geo-location. For example, an alimentary label that contains a recommendation for hazelnuts may have a low impact on an alimentary allocation standard for a user located in the Pacific Northwest, while hazelnuts hay have a high impact on an alimentary allocation standard for a user located in New Jersey. Similarly, fresh lobster may have a low impact on an alimentary allocation standard for a user located in Maine, while fresh lobster may have a high impact on an alimentary allocation standard for a user located in Oklahoma. Plan generator module 138 may be configured to add a category label associated with a shared category to alimentary instruction set 144, where addition of the label may include addition of the label and/or a datum linked to the label, such as a textual or narrative description.

With continued reference to FIG. 17, label synthesizer 1104 may be designed and configured to combine a plurality of labels in at least the alimentary instruction set output together to provide maximally efficient data presentation. Combination of labels together may include elimination of duplicate information. For instance, label synthesizer 1104 and/or at least a server 102 may be designed and configure to determine a first alimentary instruction set label of the at least an alimentary instruction set label is a duplicate of a second alimentary instruction set label of the at least a alimentary instruction set label and eliminate the first alimentary instruction set label. Determination that a first alimentary instruction set label is a duplicate of a second alimentary instruction set label may include determining that the first alimentary instruction set label is identical to the second alimentary instruction set label; for instance, a alimentary instruction set label generated from test data presented in one biological extraction of at least a biological extraction may be the same as a alimentary instruction set label generated from test data presented in a second biological extraction of at least a biological extraction. As a further non-limiting example, a first alimentary instruction set label may be synonymous with a second alimentary instruction set label, where detection of synonymous labels may be performed, without limitation, by a language processing module 114 as described above.

In one embodiment, and still referring to FIG. 17, label synthesizer 1104 may group alimentary instruction set labels according to one or more classification systems relating the alimentary instruction set labels to each other. For instance, plan generator module 138 and/or label synthesizer 1104 may be configured to determine that a first alimentary instruction set label of the at least an alimentary instruction set label and a second alimentary instruction set label of the at least an alimentary instruction set label belong to a shared category. A shared category may be a category of conditions or tendencies toward a future condition to which each of first alimentary instruction set label and second alimentary instruction set label belongs; as an example, lactose intolerance and gluten sensitivity may each be examples of digestive sensitivity, for instance, which may in turn share a category with food sensitivities, food allergies, digestive disorders such as celiac disease and diverticulitis, or the like. Shared category and/or categories may be associated with alimentary instruction set labels as well. A given alimentary instruction set label may belong to a plurality of overlapping categories. Plan generator module 138 may be configured to add a category label associated with a shared category to comprehensive instruction set 140, where addition of the label may include addition of the label and/or a datum linked to the label, such as a textual or narrative description. In an embodiment, relationships between alimentary instruction set labels and categories may be retrieved from an alimentary instruction set label classification database 1600, for instance by generating a query using one or more alimentary instruction set labels of at least a alimentary instruction set output, entering the query, and receiving one or more categories matching the query from the alimentary instruction set label classification database 1600. In one embodiment, the alimentary instruction set label classification database 1600 is configured to generate queries based on preferences of user. Preferences may be based upon religious, dietary (vegan/gluten-free), lifestyle, or any other applicable factor associated with user that is able to be manifested in the alimentary instruction set.

With continued reference to FIG. 17, in one embodiment, alimentary instruction set generator module 142 may be configured to generate alimentary instruction set 144 by converting one or more alimentary instruction set labels into narrative language. As a non-limiting example, plan generator module 138 may include and/or communicate with narrative language unit 1112, which may be configured to determine an element of narrative language associated with at least an alimentary instruction set label and include the element of narrative language in current alimentary instruction set label descriptor. Narrative language unit 1112 may implement this, without limitation, by using a language processing module 114 to detect one or more associations between alimentary instruction set labels, or lists of alimentary instruction set labels, and phrases and/or statements of narrative language. Alternatively or additionally, narrative language unit 1112 may retrieve one or more elements of narrative language from narrative language database 1116, which may contain one or more tables associating alimentary instruction set labels and/or groups of alimentary instruction set labels with words, sentences, and/or phrases of narrative language. One or more elements of narrative language may be included in alimentary instruction set, for instance for display to a user as text describing a current alimentary instruction set status of the user. Alimentary instruction set 144 may further include one or more images; one or more images may be retrieved by plan generator module 138 from an image database 1120, which may contain one or more tables associating alimentary instruction sets, groups of alimentary instruction set labels, or the like with one or more images.

With continued reference to FIG. 17, in an embodiment, relationships between alimentary labels and categories may be retrieved from an alimentary instruction label classification database 1700, for instance by generating a query using one or more alimentary labels of at least an alimentary output, entering the query, and receiving one or more categories matching the query from the alimentary instruction label classification database 1700.

Figure 18:
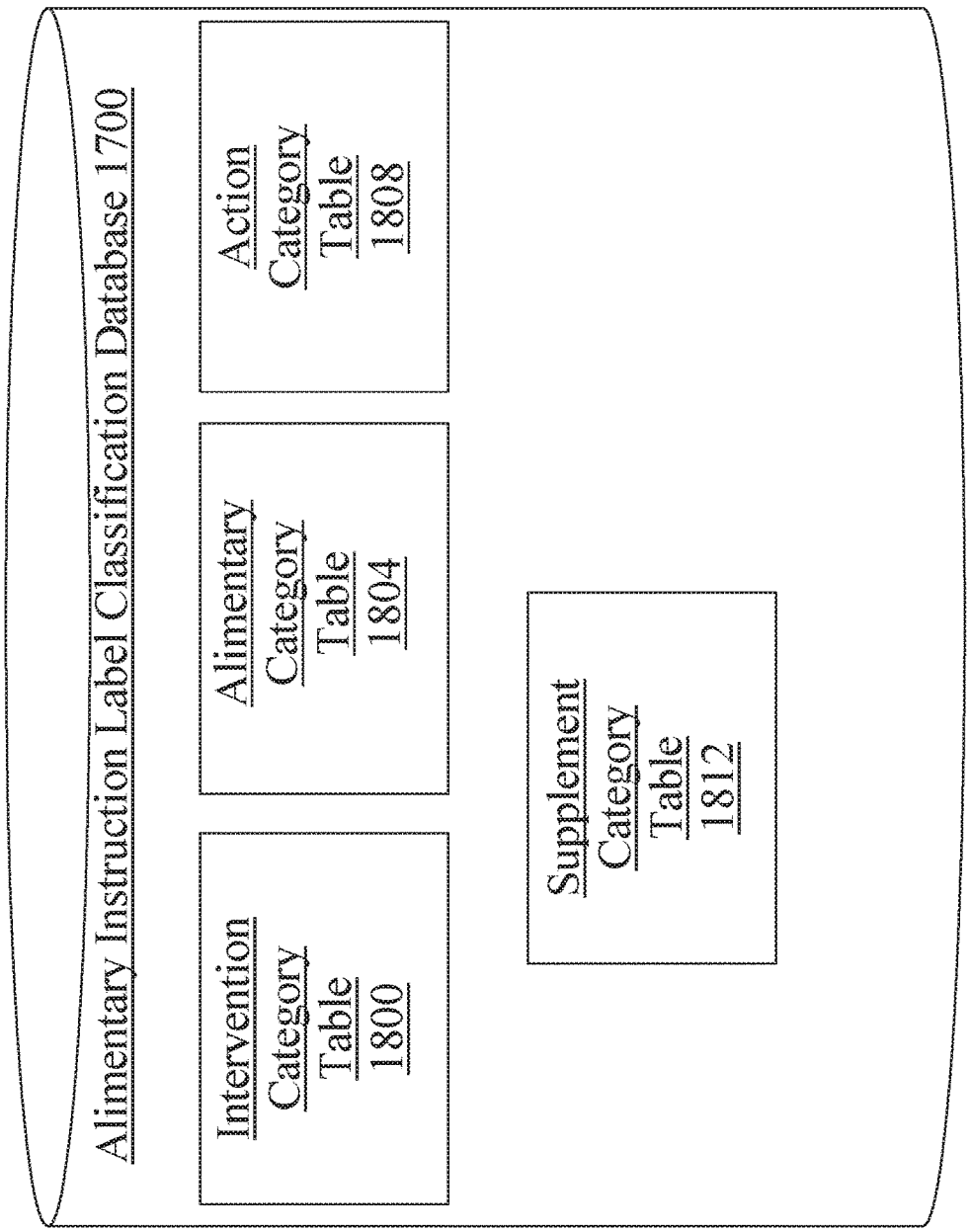
FIG. 18 is a block diagram illustrating an exemplary embodiment of an alimentary instruction label classification database.

Referring now to FIG. 18, an exemplary embodiment of an alimentary instruction label classification database 1700 is illustrated. Alimentary instruction label classification database 1700 may operate on the diagnostic engine 104. Alimentary instruction label classification database 1700 may be implemented as any database and/or datastore suitable for use as a database. One or more database tables in alimentary instruction label classification database 1700 may include, without limitation, an intervention category table 1800; an intervention may relate each alimentary label to one or more categories of conditions to be addressed by an alimentary instruction associated with that alimentary label, such as a nutritional imbalance to be corrected or the like. One or more database tables in alimentary instruction label classification database 1700 may include, without limitation, an alimentary category table 1804; which may associate an alimentary instruction label with one or more categories of nutritional properties, foodstuffs, or the like. One or more database tables in alimentary instruction label classification database 1700 may include, without limitation, an action category table 1808, which may describe one or more categories of actions, such as calorie reduction, sugar intake reduction, or the like, to which a given alimentary instruction may belong. One or more database tables in alimentary instruction label classification database 1700 may include, without limitation, a supplement table 1812, which may describe a supplement that relates to a nutritional need filled by an alimentary instruction.

Referring back now to FIG. 17, alimentary instruction set generator module 142 may be configured to generate a loss function of at least a user specific variable and diminish the loss function. Loss function may include any of the loss function approaches as described above. Alimentary instruction set generator module 142 may perform algorithms that may include weighted variables that may be customized to a user. Loss function algorithms may include any of the loss function algorithms as described above in reference to FIG. 1. Loss function algorithms may minimize distance between variables and may seek to diminish the loss function. Loss function algorithms may utilize weighted variables that are customized to a user. For example, user entries that contain trends and patterns as to alimentary instruction sets may be utilized to generate alimentary instruction sets based on previous user trends and patterns. Variables may be contained within a database 1704 as described in more detail below in reference to FIG. 19.

Figure 19:
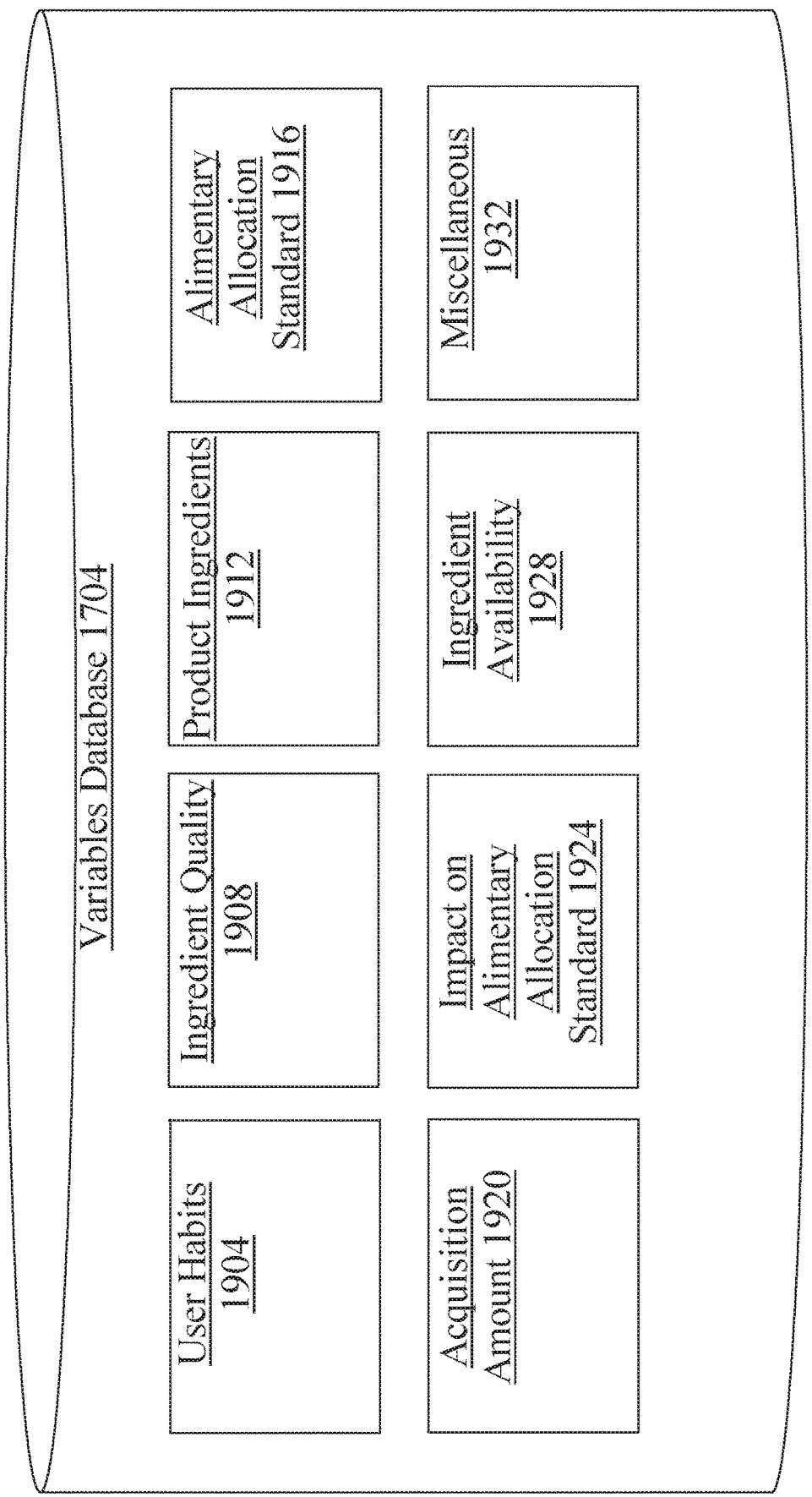
FIG. 19 is a block diagram illustrating an exemplary embodiment of a variables database.

Referring now to FIG. 19, an exemplary embodiment of variables database 1704 is illustrated. Variables database 1704 may be implemented as any database and/or datastore suitable for use as described above. One or more database tables in variables database 1704 may include, without limitation, a user habits table 1904; user habits table 1904 may contain information pertaining to habits associated with recommendations such as nutrition and supplements included within an alimentary instruction set. User habits table 1904 may include information such as what types of ingredients user cooks with, what user's views are surrounding conventional versus free range meats and dairy, what types of brands user shops for, if user purchases nutrition and/or supplements in bulk or one at a time and the like. For example, user habits table 1904 may include information about a local brand of honey user purchases or a particular supplement brand user may purchase. One or more database tables in variables database 1704 may include, without limitation, an ingredient quality table 1908; ingredient quality table 1908 may contain information pertaining to quality and/or standard of ingredients including both nutrition based ingredients such as food and supplement ingredients. Ingredient quality table 1908 may include information such as a preference for grass fed meat or dairy products that do not contain synthetic growth hormones. Ingredient quality table 1908 may include information such as a preference for non-genetically modified organisms (GMO) such as crops produced with non-GMO seeds. Ingredient quality table 1908 may include information such as a preference for pharmaceutical grade supplements or supplements that do not contain a specific filler or binder such as magnesium stearate or talc. One or more database tables in variables database 1704 may include products ingredients table 1912; product ingredients table 1912 may include information such as chemicals and/or fillers a user does not want contained within either nutrition or supplements. Product ingredients table 1912 may include information such as presence or absence of certain fillers and binders that may be found in supplements such as carrageenan, and lanolin. Product ingredients table 1912 may include information such as a user's preference to not consume foods that contain certain dyes such as Red 40 or food that contains high-fructose corn syrup or additives such as bisphenol a (BPA) or perfluoroalkyl chemicals (PFCs). One or more database tables in variables database 1704 may include alimentary allocation standard table 1916; alimentary allocation standard table 1916 may include information pertaining to user's alimentary allocation standard. Alimentary allocation standard table 1916 may include detailed information such as a user's alimentary allocation for a particular food, supplement, and/or ingredient. For example, alimentary allocation standard table 1916 may include information such as how much of total alimentary allocation standard a user may be willing to allocate to nutrition and how much of total alimentary allocation standard a user may be willing to allocate to supplements. For example, a user may wish to allocate twenty five percent of alimentary allocation standard to supplements and seventy five percent to nutrition. Alimentary allocation standard table 1916 may include further breakdowns of alimentary allocation standard such as what percentage of the twenty five percent a user allocates to supplements a user may allocate to any one particular supplement and what percentage of the seventy give percent a user allocates to nutrition a user may allocate to a particular ingredient or meal. One or more database tables in variables database 1704 may include acquisition amount table 1920; acquisition amount table 1920 may include information such as what percentage of total alimentary allocation standard a user may wish to devote to acquiring ingredients contained within an alimentary instruction set including supplement instruction set 146 and nutrition instruction set 148. For example, a user may wish to spend only so much money on gas to drive to a store twenty miles away that contains a particular supplement versus ordering the same supplement online with free shipping. Acquisition amount 1920 may also include information such as maximum amount of alimentary allocation standard a user may seek to spend to have groceries delivered, pay for shipping from online retailers, and/or cook ingredients at home versus purchasing takeout. One or more database tables in variables database 1704 may include impact on alimentary allocation standard 1924; impact on alimentary allocation standard table 1924 may include information pertaining to how any one particular ingredient including a nutrition item such as food or a supplement may impact alimentary allocation standard. For example, a pharmaceutical grade supplement produced under common good manufacturing practices (cGMP) may have a large impact on alimentary allocation standard versus a conventionally grown apple that may have a low impact on alimentary allocation standard. Similarly, a food grade supplement may have a low impact on alimentary allocation standard while an organically grown locally produced apple may have a higher impact on alimentary allocation standard. One or more database tables in variables database 1704 may include ingredient availability table 1928; ingredient availability table 1928 may include information pertaining to availability of ingredients including both nutrition ingredients and supplement ingredients and impact on alimentary allocation standard. For example, an orange grown and consumed by a user in Florida may have a lower impact on alimentary allocation standard than an orange grown in Florida and consumed by a user in Oregon. In yet another non-limiting example, Alaskan Salmon may have a low impact on alimentary allocation standard in Alaska and the Pacific Northwest while Alaskan Salmon may have a high impact on alimentary allocation standard in New England. One or more database tables in variables database 1704 may include miscellaneous table 1932; miscellaneous table 1932 may include other variables that may be utilized but have not been discussed above.

Figure 20:
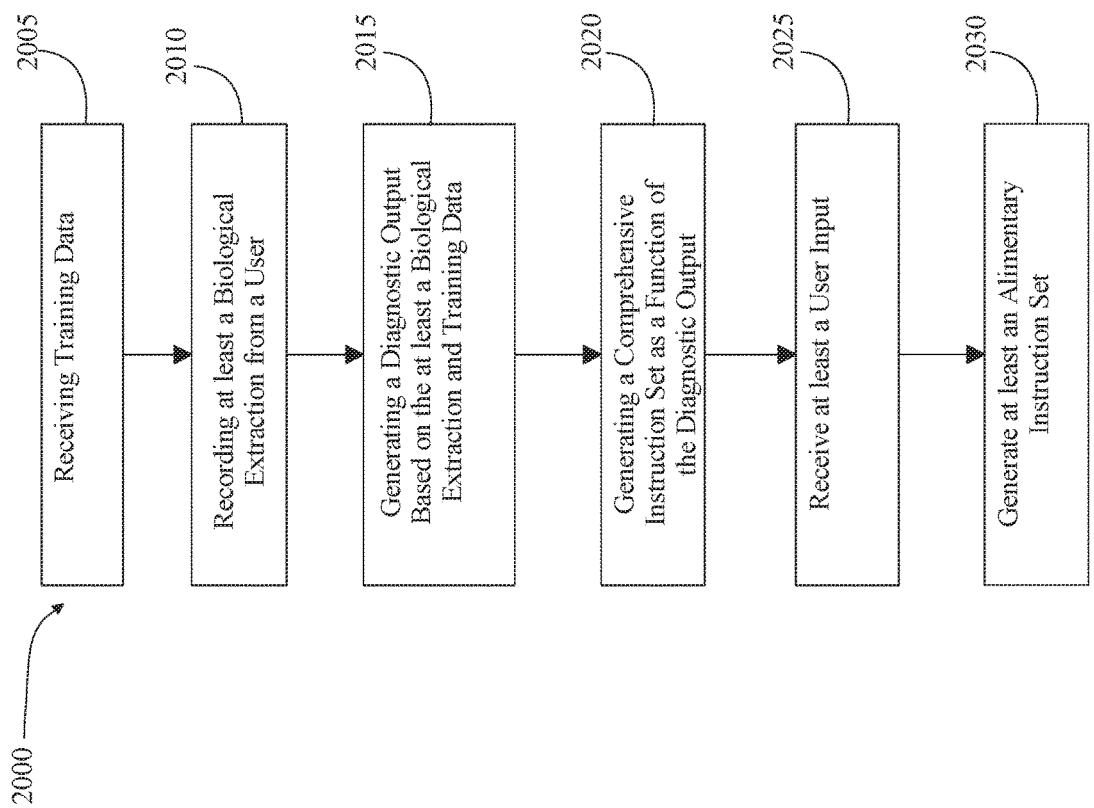
FIG. 20 is a flow diagram illustrating an exemplary embodiment of a method of achieving vibrant constitution based on user inputs.

Referring now to FIG. 20, an exemplary embodiment of a method 2000 of achieving vibrant constitution based on user inputs is illustrated. At step 2005 at least a server receives training data. Receiving training data may include receiving a first training set including a plurality of first data entries, each first data entry of the plurality of first data entries including at least an element of physiological state data and at least a correlated first prognostic label. Receiving training data includes receiving a second training set including a plurality of second data entries, each second data entry of the plurality of second data entries including at least a second prognostic label and at least a correlated ameliorative process label. Receiving training data may be performed by any of the methodologies as described in reference to FIGS. 1-19.

With continued reference to FIG. 20, at step 2010 the at least a server records a biological extraction from a user. Biological extraction may include any of the biological extractions as described above in FIGS. 1-19. Recording biological extraction may be performed by any of the methodologies as described above in reference to FIGS. 1-19.

With continued reference to FIG. 20, at step 2015 the at least a server generates a diagnostic output based on the at least a biological extraction and training data. Generating the diagnostic output may include performing at least a machine-learning algorithm as a function of the training data and the at least a biological extraction. Machine-learning algorithm may include any of the machine-learning algorithms as described above in reference to FIGS. 1-19.

With continued reference to FIG. 20, at step 2020 the at least a server generates a comprehensive instruction set as a function of the diagnostic output. Comprehensive instruction set may include any of the comprehensive instruction sets as described above in reference to FIGS. 1-19. Comprehensive instruction set may be generated utilizing any of the methodologies as described above in reference to FIGS. 1-19.

With continued reference to FIG. 20, at step 2025 the at least a server receives a user input. User input may include any of the user inputs as described above in reference to FIGS. 1-19. User input may include an alimentary quality standard. Alimentary quality standard may include any of the alimentary quality standards as described above in reference to FIGS. 1-19. Alimentary quality standard may include a user's preference for a particular quality of food, meals, and/or ingredients contained within an alimentary instruction set such as a preference for organic produce, or free range poultry. Alimentary quality standard may include for example, a user's preference for pharmaceutical grade supplements and organic produce. User input may include an alimentary allocation standard. Alimentary allocation standard may include any of the alimentary allocation standards as described above in reference to FIGS. 1-19. Alimentary allocation standard may include for example, a total amount of resources that a user is willing to devote to an alimentary instruction set. Alimentary allocation standard may include a total budget or monetary amount that a user is willing to spend over a certain amount of time such as in a month on nutrition and/or supplements. For example, a user may be willing to spend a certain percentage of user's take home earnings on alimentary allocation standard.

With continued reference to FIG. 20, at step 2030 the at least a server generates at least an alimentary instruction set as a function of the comprehensive instruction set and the at least a user input. Generating the at least an alimentary instruction set as a function of the comprehensive instruction set and the at least a user input may be done using any of the methodologies as described above in reference to FIGS. 1-19. In an embodiment the at least an alimentary instruction set may be generated to include at least a supplement instruction set 146 and at least a nutrition instruction set 148 as a function of the alimentary allocation standard and the comprehensive instruction set. This may be done using any of the methodologies as described above in reference to FIGS. 1-19. For example, an ingredient may be evaluated as against the alimentary allocation standard to determine whether it may be added to nutrition instruction set 148 or supplement instruction set. For example, a user with a Vitamin D deficiency may need Vitamin D. In such an instance, alimentary allocation standard may be used to evaluate dietary sources of Vitamin D including fatty fish, beef liver, cheese, and egg yolks versus alimentary allocation standard to supplementation with Vitamin D capsules. A user with a larger alimentary allocation standard may obtain Vitamin D through more expensive dietary sources while a user with a smaller alimentary allocation standard may obtain Vitamin D through a less expensive supplement. In an embodiment, the server may generate a supplement instruction set 146 as a function of the nutrition instruction set 148 such as by consulting interchange database 924 and/or variables database 1704. This may be done utilizing any of the methodologies as described above in reference to FIGS. 1-19. For example, a user may prioritize consumption of more expensive locally grown food sources, and as such supplement instruction set 146 generated as a function of the nutrition instruction set 148 containing locally grown ingredients may not include pharmaceutical grade supplements but rather may include less expensive food grade supplements. In an embodiment, the server may generate a nutrition instruction set 148 as a function of the supplement instruction set. This may be done utilizing any of the methodologies as described above in reference to FIGS. 1-18. For example, a user with multiple chronic health conditions may require a larger percentage of alimentary allocation standard to be allocated to supplement instruction set 146 and as such, user may have a nutrition instruction set 148 that includes organic produce but includes non-organic dairy. This may be performed by consulting interchange database 924 and/or variables database 1704. In an embodiment, nutritional instruction set may be optimized to achieve optimal nutritional value for a user as a function of alimentary allocation standard. For example, where a user prefers not to consume organic items or cannot allocate all or a portion of alimentary allocation standard towards organic items, conventional items may be substituted and optimized based on nutritional value. For example, a conventional cantaloupe can be consumed in lieu of a more expensive organic cantaloupe as long as user avoids consuming cantaloupe rind or seeds where pesticides reside. Similarly, conventionally grown lettuce or salad may be consumed in lieu of a more expensive organic lettuce or salad as long as user thoroughly washes and dries lettuce or salad to remove residual pesticides.

With continued reference to FIG. 20, generating the at least an alimentary instruction set may include generating a loss function of at least a user variable and diminishing the loss function. Loss function may include any of the loss functions as described above in reference to FIGS. 1-19. Generating a loss function may be performed utilizing any of the methodologies as described above in reference to FIGS. 1-19. User specific variables may include any of the variables as described above in reference to FIG. 19. In an embodiment, variable may include for example an ingredient quality variable as described above in more detail in reference to FIG. 19. In an embodiment, variable may include for example a product ingredient variable as described above in more detail in reference to FIG. 19. In an embodiment, variable may include for example an impact on alimentary allocation standard variable as described above in more detail in reference to FIG. 19.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 21:
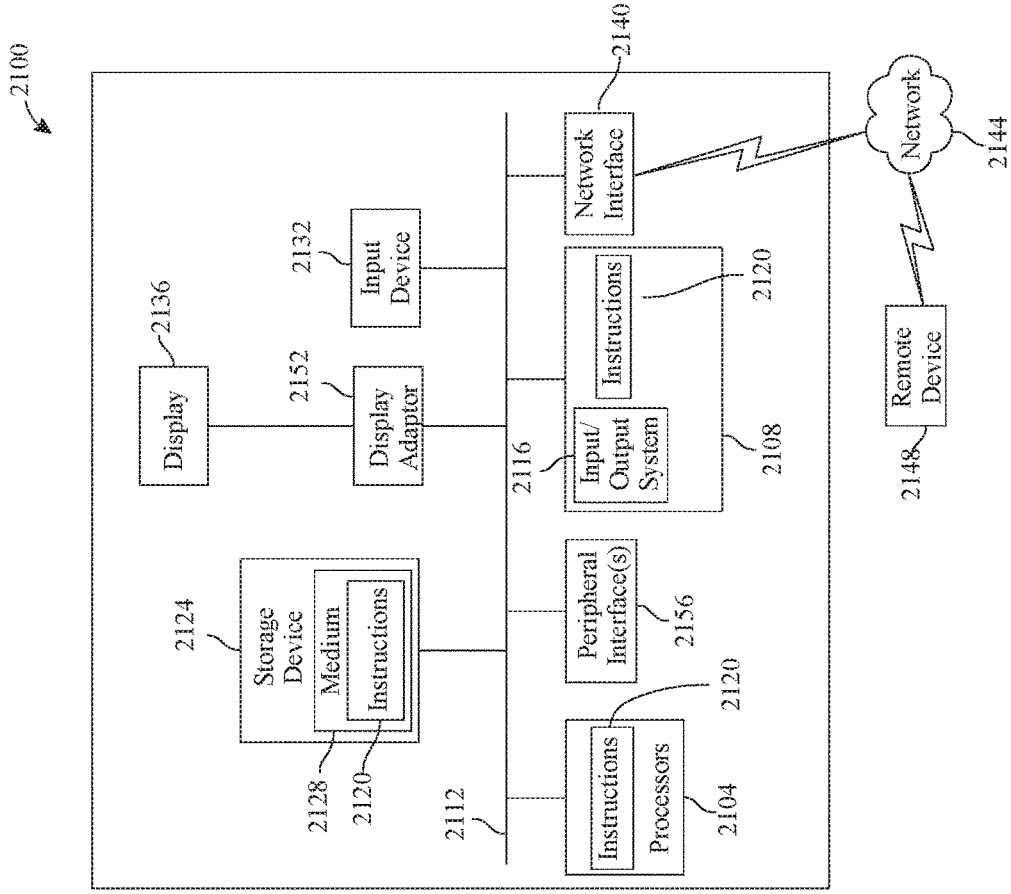
FIG. 21 is a block diagram of a computing system that can be used to implement any one or more of the methodologies disclosed herein and any one or more portions thereof.

FIG. 21 shows a diagrammatic representation of one embodiment of a computing device in the exemplary form of a computer system 2100 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 2100 includes a processor 2104 and a memory 2108 that communicate with each other, and with other components, via a bus 2112. Bus 2112 may include any of several types of bus structures including, but not limited to, a memory bus, a memory controller, a peripheral bus, a local bus, and any combinations thereof, using any of a variety of bus architectures.

Memory 2108 may include various components (e.g., machine-readable media) including, but not limited to, a random access memory component, a read only component, and any combinations thereof. In one example, a basic input/output system 2116 (BIOS), including basic routines that help to transfer information between elements within computer system 2100, such as during start-up, may be stored in memory 2108. Memory 2108 may also include (e.g., stored on one or more machine-readable media) instructions (e.g., software) 2120 embodying any one or more of the aspects and/or methodologies of the present disclosure. In another example, memory 2108 may further include any number of program modules including, but not limited to, an operating system, one or more application programs, other program modules, program data, and any combinations thereof.

Computer system 2100 may also include a storage device 2124. Examples of a storage device (e.g., storage device 2124) include, but are not limited to, a hard disk drive, a magnetic disk drive, an optical disc drive in combination with an optical medium, a solid-state memory device, and any combinations thereof. Storage device 2124 may be connected to bus 2112 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 2124 (or one or more components thereof) may be removably interfaced with computer system 2100 (e.g., via an external port connector (not shown)). Particularly, storage device 2124 and an associated machine-readable medium 2128 may provide nonvolatile and/or volatile storage of machine-readable instructions, data structures, program modules, and/or other data for computer system 2100. In one example, software 2120 may reside, completely or partially, within machine-readable medium 2128. In another example, software 2120 may reside, completely or partially, within processor 2104.

Computer system 2100 may also include an input device 2132. In one example, a user of computer system 2100 may enter commands and/or other information into computer system 2100 via input device 2132. Examples of an input device 2132 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 2132 may be interfaced to bus 2112 via any of a variety of interfaces (not shown) including, but not limited to, a serial interface, a parallel interface, a game port, a USB interface, a FIREWIRE interface, a direct interface to bus 2112, and any combinations thereof. Input device 2132 may include a touch screen interface that may be a part of or separate from display 2136, discussed further below. Input device 2132 may be utilized as a user selection device for selecting one or more graphical representations in a graphical interface as described above.

A user may also input commands and/or other information to computer system 2100 via storage device 2124 (e.g., a removable disk drive, a flash drive, etc.) and/or network interface device 2140. A network interface device, such as network interface device 2140, may be utilized for connecting computer system 2100 to one or more of a variety of networks, such as network 2144, and one or more remote devices 2148 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 2144, may employ a wired and/or a wireless mode of communication. In general, any network topology may be used. Information (e.g., data, software 2120, etc.) may be communicated to and/or from computer system 2100 via network interface device 2140.

Computer system 2100 may further include a video display adapter 2152 for communicating a displayable image to a display device, such as display device 2136. Examples of a display device include, but are not limited to, a liquid crystal display (LCD), a cathode ray tube (CRT), a plasma display, a light emitting diode (LED) display, and any combinations thereof. Display adapter 2152 and display device 2136 may be utilized in combination with processor 2104 to provide graphical representations of aspects of the present disclosure. In addition to a display device, computer system 2100 may include one or more other peripheral output devices including, but not limited to, an audio speaker, a printer, and any combinations thereof. Such peripheral output devices may be connected to bus 2112 via a peripheral interface 2156. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for achieving vibrant constitution based on user inputs,
the system comprising:
at least a sensor;
at least a server comprising at least a processor and a memory, wherein the memory is communicatively connected to the at least a processor, and wherein the memory contains instructions configuring the at least a processor to:
receive training data which comprises:
receiving a first training set including a plurality of first data entries, each first data entry of the plurality of first data entries including at least an element of physiological state data and at least a correlated first prognostic label, wherein the element of physiological state data comprises genomic data, and wherein the physiological state data is received from the at least a sensor; and
receiving a second training set including a plurality of second data entries, each second data entry of the plurality of second data entries including at least a second prognostic label and at least a correlated ameliorative process label;
a diagnostic engine operating on the at least a server wherein the diagnostic engine is configured to:
record at least a biological extraction from a user; and
generate a diagnostic output based on the at least a biological extraction and the training data;
a plan generator module operating on the at least a server designed and configured to:
generate a comprehensive instruction set associated with the user as a function of the diagnostic output; and
an alimentary instruction set generator module operating on the at least a server, the alimentary instruction set generator module designed and configured to:
receive at least a user input, wherein the at least a user input further comprises an alimentary quality standard, and wherein the alimentary quality standard further comprises at least a user preference associated with at least a particular quality of produce; and
generate at least an alimentary instruction set as a function of the comprehensive instruction set and the at least a user input, wherein the at least a user input comprises an alimentary allocation standard, wherein the alimentary allocation standard includes an amount of resources that the user is willing to devote to an alimentary instruction set, wherein the at least an alimentary instruction set comprises at least a supplement instruction set and at least a nutrition instruction set, wherein the at least a nutrition set is generated from the at least a supplement instruction set based on geographic product availability, the amount of resources comprising a first percentage of the alimentary allocation standard for the at least a supplement instruction set and a second percentage of the alimentary allocation standard for the at least a nutrition instruction set.

2. The system of claim 1, wherein generating the diagnostic output further comprises performing at least a machine-learning algorithm as a function of the training data and the at least a biological extraction.

3. The system of claim 1, wherein the user preference further specifies avoiding at least a second produce as a function of the user input.

4. The system of claim 1, wherein the alimentary instruction set generator module is further configured to generate at least an alimentary instruction by:
generating a loss function of at least a user variable; and
minimizing the loss function.

5. The system of claim 4, wherein the at least a user variable comprises an impact on an alimentary allocation standard variable.

6. The system of claim 1, wherein the amount of resources includes a budget amount or dollar amount that the user is willing to devote to the alimentary instruction set for a specific period of time.

7. A method of achieving vibrant constitution based on user inputs, the method comprising:
receiving, by at least a server, training data which comprises:
receiving a first training set including a plurality of first data entries, each first data entry of the plurality of first data entries including at least an element of physiological state data and at least a correlated first prognostic label, wherein the element of physiological state data comprises genomic data; and
receiving a second training set including a plurality of second data entries, each second data entry of the plurality of second data entries including at least a second prognostic label and at least a correlated ameliorative process label;
recording, by a diagnostic engine operating on the at least a server, at least a biological extraction from a user;
generating, by the diagnostic engine, a diagnostic output based on the at least a biological extraction and the training data;
generating, by a plan generator module operating on the at least a server, a comprehensive instruction set associated with the user as a function of the diagnostic output;
receiving, by an alimentary instruction set generator module operating on the at least a server, at least a user input, wherein the at least a user input further comprises an alimentary quality standard, and wherein the alimentary quality standard further comprises at least a user preference associated with at least a particular quality of produce; and
generating, by the alimentary instruction set generator, at least an alimentary instruction set as a function of the comprehensive instruction set and the at least a user input, wherein the at least a user input comprises an alimentary allocation standard, wherein the alimentary allocation standard includes an amount of resources that the user is willing to devote to an alimentary instruction set, wherein the at least an alimentary instruction set comprises at least a supplement instruction set and at least a nutrition instruction set, wherein the at least a nutrition set is generated from the at least a supplement instruction set based on geographic product availability, the amount of resources comprising a first percentage of the alimentary allocation standard for the at least a supplement instruction set and a second percentage of the alimentary allocation standard for the at least a nutrition instruction set.

8. The method of claim 7, wherein generating the diagnostic output further comprises performing at least a machine-learning algorithm as a function of the training data and the at least a biological extraction.

9. The method of claim 7, wherein the user preference further specifies avoiding at least a second produce as a function of the user input.

10. The method of claim 7, wherein generating the at least an alimentary instruction set further comprises:
generating a loss function of at least a user variable; and
minimizing the loss function.

11. The method of claim 10, wherein the at least a user variable comprises an impact on an alimentary allocation standard variable.

12. The method of claim 7, wherein the amount of resources includes a budget amount or dollar amount that the user is willing to devote to the alimentary instruction set for a specific period of time.

* * * * *